United States Patent
Pennebaker, III

(10) Patent No.: US 10,068,467 B1
(45) Date of Patent: Sep. 4, 2018

(54) SYSTEM AND METHOD FOR FIELD MONITORING OF STATIONARY ASSETS

(71) Applicant: E. Strode Pennebaker, III, Houston, TX (US)

(72) Inventor: E. Strode Pennebaker, III, Houston, TX (US)

(*) Notice: Subject to any disclaimer, the term of this patent is extended or adjusted under 35 U.S.C. 154(b) by 0 days.

(21) Appl. No.: 15/612,424

(22) Filed: Jun. 2, 2017

Related U.S. Application Data

(63) Continuation of application No. 13/866,672, filed on Apr. 19, 2013, now Pat. No. 9,711,038, which is a continuation of application No. 13/839,377, filed on Mar. 15, 2013, which is a continuation-in-part of application No. 13/601,083, filed on Aug. 31, 2012.

(60) Provisional application No. 61/529,757, filed on Aug. 31, 2011.

(51) Int. Cl.
| | |
|---|---|
| *G08C 17/02* | (2006.01) |
| *G01F 23/296* | (2006.01) |
| *G01F 25/00* | (2006.01) |
| *G01N 29/024* | (2006.01) |
| *G01N 29/14* | (2006.01) |
| *G01N 29/50* | (2006.01) |
| *G01F 23/28* | (2006.01) |
| *G01F 23/00* | (2006.01) |
| *G01N 29/07* | (2006.01) |

(52) U.S. Cl.
CPC .............. *G08C 17/02* (2013.01); *G01F 23/00* (2013.01); *G01F 23/28* (2013.01); *G01F 23/296* (2013.01); *G01F 23/2962* (2013.01); *G01F 25/0061* (2013.01); *G01N 29/024* (2013.01); *G01N 29/07* (2013.01); *G01N 29/14* (2013.01); *G01N 29/50* (2013.01); *G01N 2291/02836* (2013.01)

(58) Field of Classification Search
CPC ......... G08C 17/02; G01F 23/00; G01F 23/28; G01F 23/296; G01F 23/2962; G01F 25/0061; G01N 29/024; G01N 29/07; G01N 29/14; G01N 29/50; G01N 2291/02836
See application file for complete search history.

(56) References Cited

U.S. PATENT DOCUMENTS

| | | | | |
|---|---|---|---|---|
| 5,456,114 A | * | 10/1995 | Liu ........................ | B64D 15/20 73/290 V |
| 2010/0017152 A1 | * | 1/2010 | Potter ................. | G01F 23/2962 702/54 |

* cited by examiner

*Primary Examiner* — Hai Phan
*Assistant Examiner* — Franklin Balseca
(74) *Attorney, Agent, or Firm* — Osha Liang LLP

(57) ABSTRACT

A wireless sensor network including a number of wireless modules for monitoring sensors associated with stationary assets. Additionally, the wireless module includes a wireless transceiver, a processor, a location acquisition unit, which are configured to acquire a location item for identifying a location of the wireless module, and a memory.

8 Claims, 40 Drawing Sheets

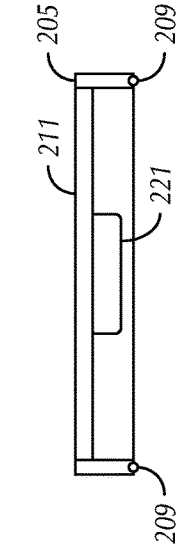
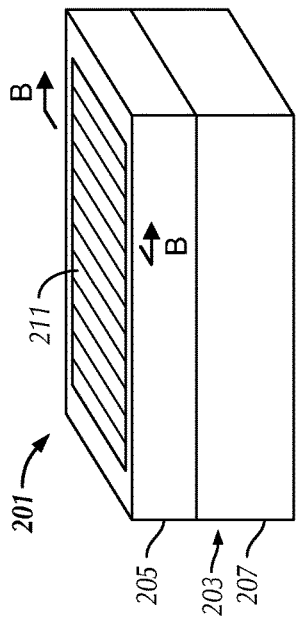
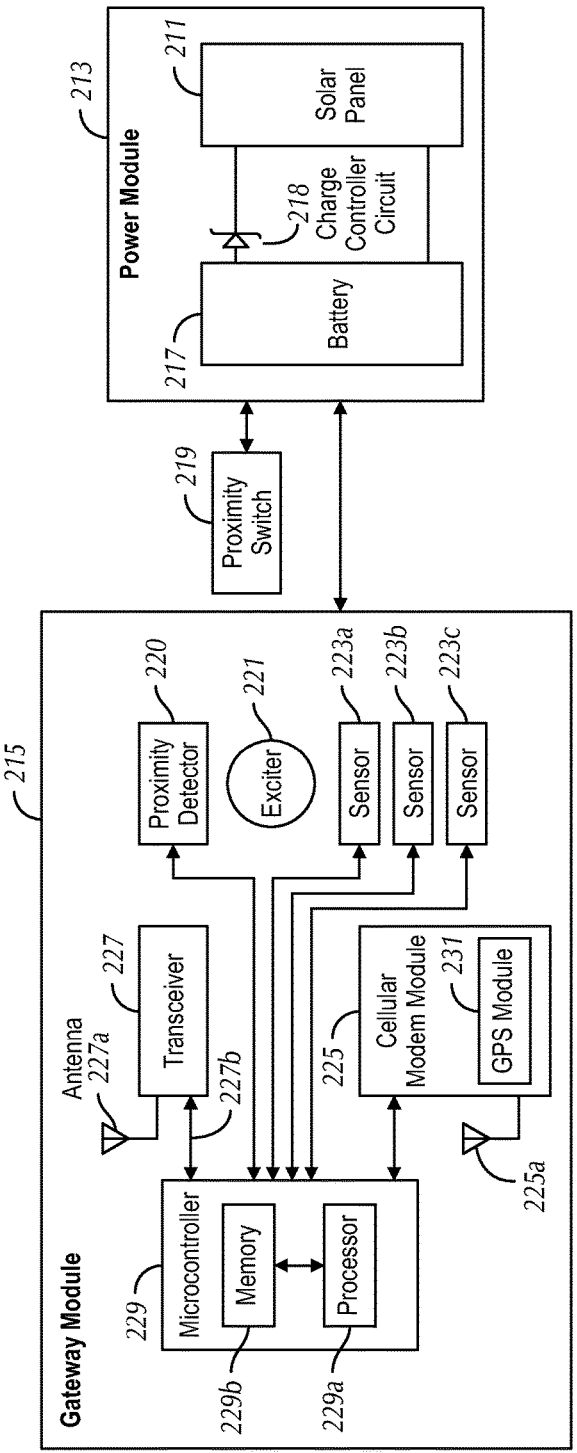

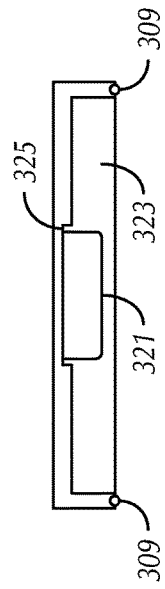
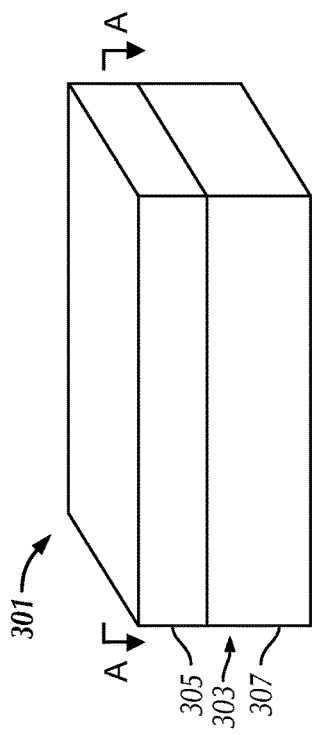
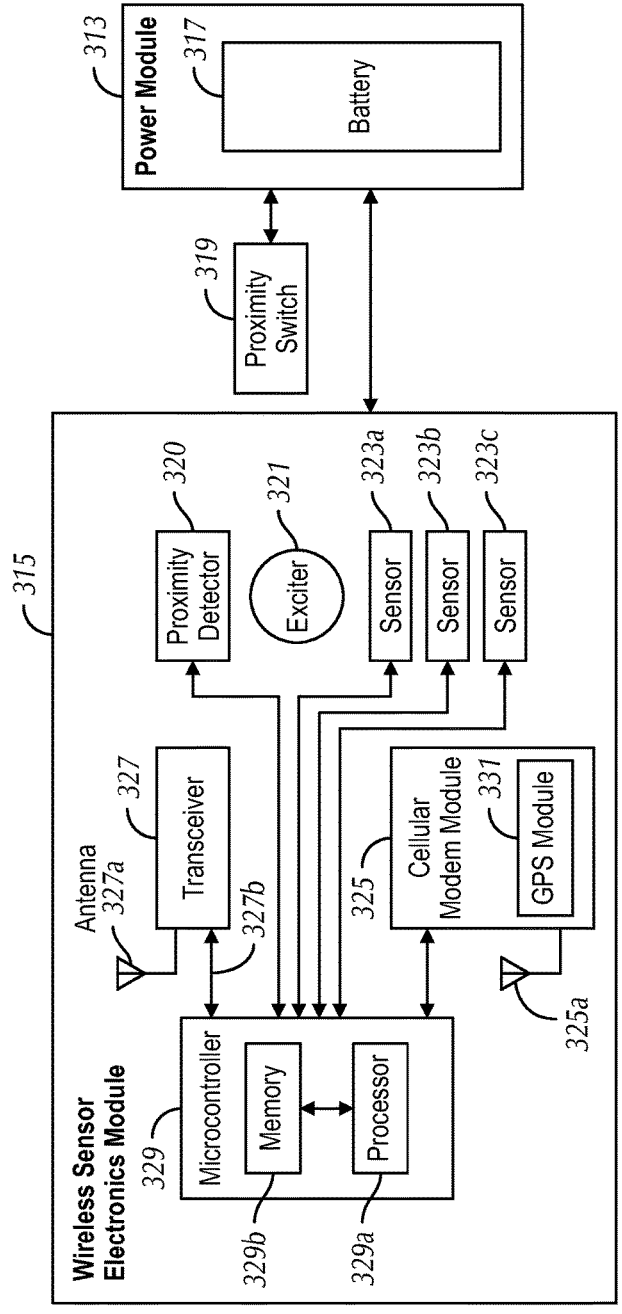

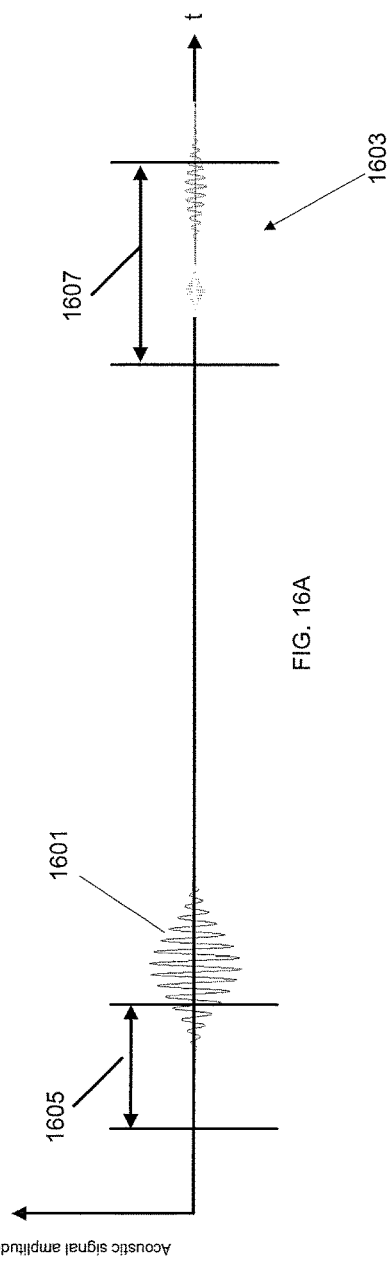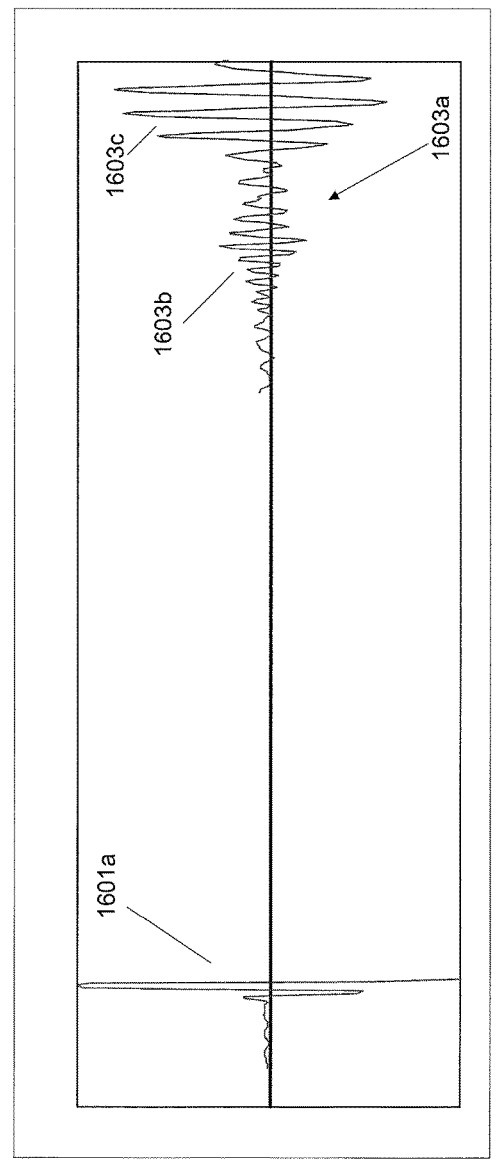

SYSTEM AND METHOD FOR FIELD MONITORING OF STATIONARY ASSETS

CROSS-REFERENCE TO RELATED APPLICATIONS

This application claims benefit under 35 U.S.C. § 120 to U.S. patent application Ser. No. 13/866,672, filed on Apr. 19, 2013, which claims priority under 35 U.S.C. § 119(e) to which U.S. patent application Ser. No. 13/839,377, filed on Mar. 15, 2013, which claims priority under 35 U.S.C. § 119(e) to which U.S. patent application Ser. No. 13/601,083, filed on Aug. 31, 2012, which claims priority under 35 U.S.C. § 119(e) to U.S. Provisional Patent Application Ser. No. 61/529,757, filed on Aug. 31, 2011. All of these applications are incorporated by reference herein in their entirety.

BACKGROUND

In the field of stationary asset monitoring, networks of wireless sensors are often used to monitor the status of sets of stationary assets co-located at one or more sites. For example, sensors that are part of an industrial site sensing network can monitor one or more conditions associated with equipment deployed in an industrial complex. For example, the data originates from a collection of wireless/wired sensors that may be monitoring stationary assets, e.g., tanks, piping systems, processing systems, fluid and gas systems, and electrical systems.

Furthermore, for a site such as an oilfield, various sensors may be deployed in order to monitor any number of oilfield-related assets. For example, known sensor types include fluid level detectors that are often deployed for monitoring the amount of oil or condensate within holding tanks. In many situations, determination of fluid level inside of a vessel is accomplished by installing a sensor device inside the vessel with wiring connected to a collection point outside of the vessel from which the data are often forwarded to a local or remote monitoring system. The sensors can be based on many phenomena, such as position of floats on top of the fluid level interface(s), measurement of fluid pressure which can be converted to level height, ultrasonic travel time measurement to the fluid level, microwave, optical travel time sensors or time delay reflectometry techniques. In addition, flow meters are commonly deployed on pipelines and compressor monitors are deployed to monitor the status and health of compressors. In addition, various sensors can be deployed at the wellhead for monitoring tubing, casing, or surface flowline pressure or to monitor and control valves.

Typically, for field health and data notifications, daily updates are generally acceptable. Oilfield custom is to provide a 6:00 AM, report to engineers and supervisors when they arrive in the office. For a non-automated location, a simple 24-hour summary of production and current system status (pressure, tank levels) is normally sufficient. Even for typical automated onshore locations it is unusual to expect a morning report of provide more than hourly data.

Likewise, for site monitoring in the agriculture industry, stationary assets, such as water or fuel tanks may be remotely monitored and configured to alert service personnel when refill becomes necessary. Furthermore, geofences, or the like, may be continuously monitored to alert supervisors of the presence of trespassers, and/or field personnel.

Fields that include a large number and diversity of stationary assets may be distributed over vast tracts of land and are often distributed in extremely dangerous or inhospitable environments. Thus, modern asset monitoring networks deploy complex and costly wireless sensors and/or SCADA control elements that may be integrated into a wide area networks (WANs) or even the internet/worldwide web. Often, due to the complexity of these systems highly-trained service personnel are needed for installation, diagnosis and repair of the on-site sensors and power systems. Furthermore, present systems require bulky and cumbersome mounting systems in addition to large area solar panels in order to provide a suitable source of power.

SUMMARY

In general, in one aspect, one or more embodiments of the invention are directed to a method for monitoring a field comprising a stationary asset and a co-located stationary wireless module (WM). The method includes receiving, by a server and from the WM, a location item identifying a location of the stationary asset and the WM. The method further includes accessing, by the server, a data structure identifying field coordinates corresponding to assets and determining a location of the WM by comparing the location item with the plurality of field coordinates.

In general, in one aspect, one or more embodiments of the invention are directed to a wireless module for monitoring sensors associated with stationary assets. The wireless module includes a wireless transceiver, a processor, a location acquisition unit, configured to acquire a location item identifying a location of the wireless module, and a memory. The memory includes computer readable instructions that when executed by the processor in response to a power enable signal cause the location acquisition unit to automatically acquire the location item and cause the wireless module to transmit the location item, via the first wireless transceiver, to a remote server.

In general, in one aspect, one or more embodiments of the invention are directed to a method for remote calibration of a wireless sensor. The method includes receiving, by a server and from a wireless device, a first calibration item identifying a first conversion factor to convert raw sensor output to calibrated sensor measurement. The method further includes receiving, by a server and from a wireless device, a second calibration item identifying a second conversion factor to convert raw sensor output to calibrated sensor measurement. The method further includes computing, by the server, a calibration curve based on the first and second conversion factors and calibrating a set of raw sensor data based on the computed calibration curve.

In general, in one aspect, one or more embodiments of the invention are directed to an acoustic impulse generator. The acoustic impulse generator includes an enclosure, a processor, a wireless transceiver, a striking mechanism rotationally mounted within the enclosure and attached to a rotary actuator. The striking mechanism includes an elongated member, wherein a first end of the elongated member is attached to a rotor of the rotary actuator and a second end of the elongated member is free to move in response to a rotation of the rotor. The striking mechanism further includes a striker disposed proximate to the second end of the elongated member, wherein, in response to the rotation of the rotor, the striker is configured to strike an inner surface of the enclosure thereby generating an acoustic impulse.

In general, in one aspect, one or more embodiments of the invention are directed to a method for determining a fill level of a container. The method includes acquiring first impulse data, and reformatting the acquired first impulse data into a first subset of the acquired first impulse data. The first subset includes a plurality of subset times, wherein the first subset includes fewer data points than the first impulse data. The method further, acquiring second impulse data, and reformatting the acquired second impulse data into a second subset of the acquired second impulse data. The second subset includes a plurality of second subset times, wherein the second subset includes less data points than the second impulse data. The method further includes computing the fill level based on the first and the second impulse data subsets.

In general, in one aspect, one or more embodiments of the invention are directed to a system for monitoring the pumping condition of a rod pump. The system includes a beam, pivotably mounted to a mounting post and a wireless sensor module mounted to the beam. The wireless sensor module includes an accelerometer configured to acquire angular position data based on of an angular position of the beam relative to the direction of gravity and a wireless transceiver configured to receive the angular position data, and to wirelessly transmit the angular position data to a wireless module.

In general, in one aspect, one or more embodiments of the invention are directed to a system for monitoring a level controller. The system includes a displacement shaft having a first end and a second end, wherein the first end is connected to a torque shaft and the second end is extends to a liquid displacement member configured to transmit a vertical force responsive to a change in a liquid level as a force tending to rotate the torque shaft. The system further includes a torque bar connected to the torque shaft so that a movement of the torque shaft is transmitted to the torque bar. The system further includes a wireless sensor module mounted to torque bar, wherein the wireless sensor module comprises an accelerometer configured to acquire angular position data based on an angular position of the torque bar relative to the direction of gravity and a wireless transceiver configured to receive the angular position data, and to wirelessly transmit the angular position data to a wireless module.

Other aspects and advantages of the invention will be apparent from the following description and the appended claims.

BRIEF DESCRIPTION OF DRAWINGS

FIGS. 2A-2C show an example of a wireless gateway for use in a system for field monitoring of stationary assets in accordance with one or more embodiments of the invention.

FIGS. 3A-C show an example of a remote wireless sensor module for use in a system for remote stationary asset monitoring in accordance with one or more embodiments of the invention.

FIGS. 16A-16B show an example of acoustic impulse data acquired by an acoustic impulse generator and acoustic impulse data acquired by an acoustic impulse receiver in accordance with one or more embodiments of the invention.

DETAILED DESCRIPTION

Figure 1:
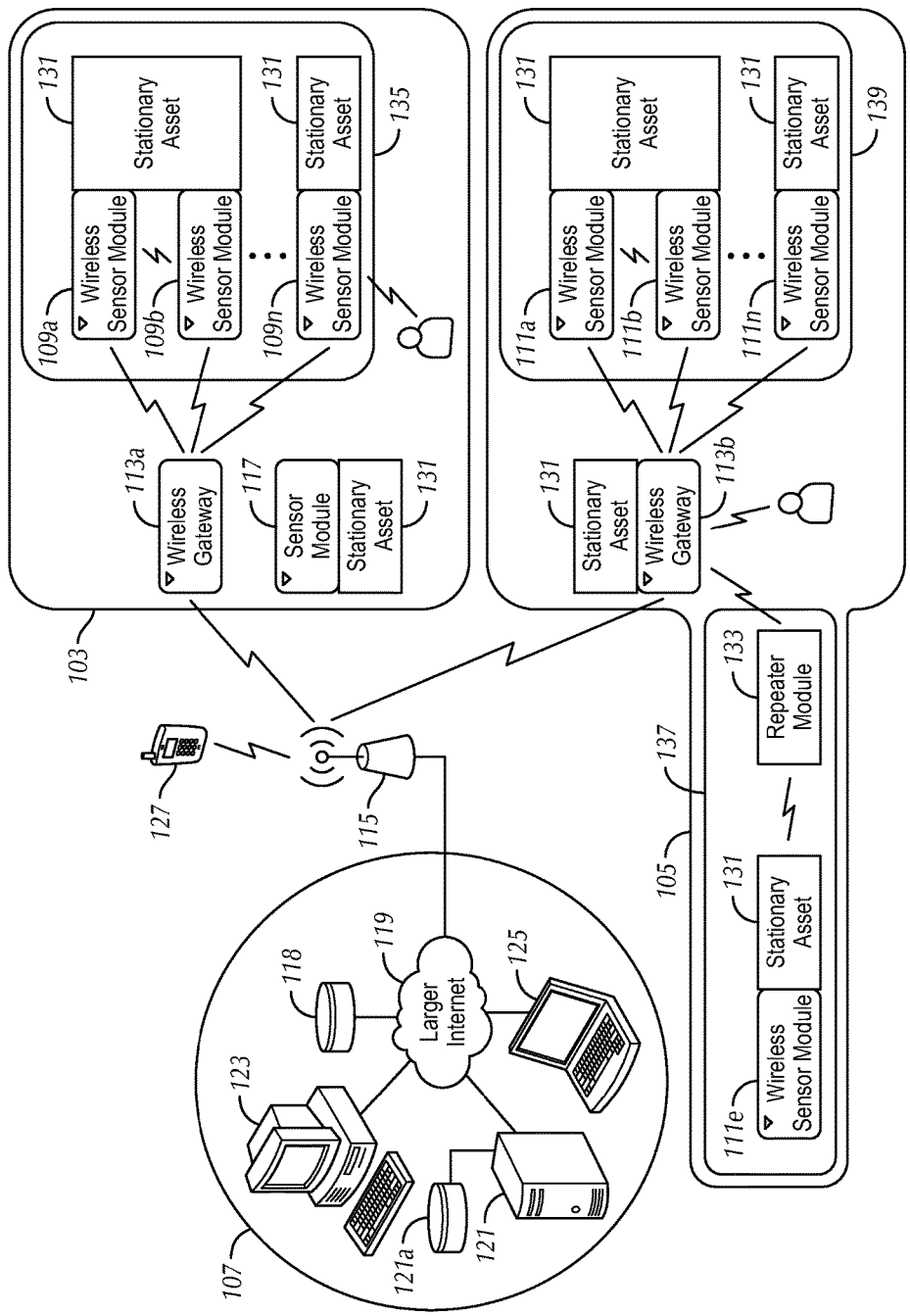
FIG. 1 shows an example of a system for field monitoring of stationary assets in accordance with one or more embodiments of the invention.

Specific embodiments of a system and method for field monitoring of stationary assets is described in detail with reference to the accompanying figures. Like elements in the various figures (also referred to as Figs.) are denoted by like reference numerals for consistency.

In the following detailed description of embodiments, numerous specific details are set forth in order to provide a more thorough understanding of the system and method for field monitoring of stationary assets. However, it will be apparent to one of ordinary skill in the art that these embodiments may be practiced without these specific details. In other instances, well-known features have not been described in detail to avoid unnecessarily complicating the description.

Certain embodiments of the methods disclosed herein in accordance with one or more embodiments of the invention may be implemented on virtually any type of computer or mobile device regardless of the platform being used. For example, a computer system or mobile device includes one or more processor(s), associated memory (e.g., random access memory (RAM), cache memory, flash memory, etc.), a storage device (e.g., a hard disk, an optical drive such as a compact disk drive or digital video disk (DVD) drive, a flash memory, etc.), and numerous other elements and functionalities typical of today's computers and mobile devices. As used herein, a computer system further includes those systems that employ system of a chip (SoC) architectures, application specific integrated circuits (ASIC), field programmable gate arrays (FPGA), microcontrollers, or the like. The computer system or mobile device may also include input means, such as a keyboard, a mouse, microphone, proximity sensor, or touch sensor/screen. Further, the computer may include output means, such as a monitor (e.g., a liquid crystal display (LCD), a plasma display, or cathode ray tube (CRT) monitor). The computer system may be connected to a network (e.g., a local area network (LAN), a wide area network (WAN) such as the Internet, or any other similar type of network) via a network interface connection. Those skilled in the art will appreciate that many different types of computer and mobile device systems exist, and the aforementioned input and output means may take other forms generally known in the art. Generally speaking, the computer system includes at least the minimal processing, input, and/or output means necessary to practice embodiments of the invention.

Further, software instructions to perform methods discloses herein in accordance with one or more embodiments of the invention may be stored on any non-transitory computer readable medium such as a compact disc (CD), a diskette, a tape, a hard drive, or any type of read only memory such as EPROM, flash ROM, or any other computer readable storage device.

In general, embodiments of the invention relate to a system and method for field monitoring of stationary assets. More specifically, embodiments of the invention relate to a wireless sensor network of extremely small, lightweight, low maintenance and low cost modules for monitoring, for example, oilfield assets and/or agricultural assets. As used herein, a stationary asset refers to an asset having a fixed geographical location. Furthermore, as referred to herein, a field may be any outdoor region, site, or area including at least one stationary fixed asset to be monitored. The modules may include, for example, wireless sensor modules that are attached to the stationary assets, wireless gateway units, and wireless repeater units, at least one of which is located on-site and/or attached to one or more stationary assets. The wireless sensor modules and gateways are configured to automatically associate with one another and to automatically log on, register, and/or report data to, a remote server with minimal or no user input. The modules may be location aware, e.g., may include GPS receivers/chipsets, and may be further configured for straightforward field serviceability, maintenance, and initial configuration, as described in more detail below.

FIG. 1 shows an example of a system for field monitoring of stationary assets in accordance with one or more embodiments of the invention. In the example shown, the system includes two sensor sub-networks 103 and 105, each sub-network in wireless communication with remote server network 107. More specifically, sensor sub-network 103 includes a wireless gateway 113a and a number of wireless sensor modules 109a-109n and sensor sub-network 105 includes a wireless gateway 113b and a number of wireless sensor modules 111a-111n. In accordance with one or more embodiments, wireless sensor modules 109a-109n and 111a-111n are disposed near, or attached to, stationary assets 131 to be monitored. For example, in the case of oil-field monitoring, sensor modules 109a-109n may be attached to storage tanks, pipelines, compressors, beam pumps, etc. Accordingly, the sensor modules themselves may be of several different types, each sensor module being adapted for a particular purpose, e.g., liquid level sensing, flow metering, proximity sensing, noise and vibration sensing, environmental sensing, photo or video capturing, acceleration sensing, vehicle sensing, or any other type of sensor that may find applicability in the field or further described below.

Each sub-network includes a site that is being monitored; and each site being monitored may include a number of stationary assets, e.g., cites 135, 137 and 139 shown in FIG. 1. Furthermore, as used herein, a field refers to a collection of sites and/or a collection of stationary assets. Each one of the group of sensor modules within a site communicates with a wireless gateway or wireless repeater. Furthermore, in accordance with one or more embodiments, the sensors modules may communicate between themselves, wirelessly or wired, as is shown between the pairs of sensor modules 109a, 109b and 111a, 111b. Furthermore, in accordance with one or more embodiments, a wireless sensor module 111e mounted to a stationary asset 131 that is located in a field having a geographically large area may communicate with one or more repeater modules 133. Repeater modules 133 are configured to relay (store and forward) to wireless gateway 113b data-packets from any geographically remote sensor modules that are outside the range of the wireless gateway unit 113b but within the range of the repeater module 133. In addition, for wireless gateways 113a, 113b within range of any sensor modules, the wireless gateways 113a, 113b relay data from the sensor modules 109a-109n and/or 111a-111n, respectively, to the remote server network 107 by way of one or more cellular base stations 115 connected to a wide area network (not shown). Each and every sensor module of the wireless sensor network need not wirelessly communicate with the wireless gateway module or repeater module, but may, in certain circumstances, communicate by wired connection, e.g., as shown by sensor module 117 within sensor sub-network 103.

In accordance with one or more embodiments, a wireless gateway and/or sensor module may be equipped with a global positioning system (GPS) module including a GPS receiver and chipset configured to geolocate the wireless gateway/sensor module, e.g., by computing the latitude and longitude coordinates of the wireless gateway/sensor module. As used herein, wireless gateway and/or sensor modules that are configured to acquire their own location information is termed "location awareness."

In accordance with one or more embodiments, a wireless sensor module is configured to acquire and/or store sensor data in local memory located within the wireless sensor module, as described in more detail below. Once acquired, the sensor data is transmitted to one or more wireless gateways. The wireless gateways may encode and transmit this data in an appropriate form and under the appropriate set of protocols for transmission over a cellular network. For example, any known wireless communication method may be used by the wireless gateway, e.g., GSM, CDMA, OFDMA, etc. One of ordinary skill will appreciate that cellular networks are generally known in the art and, thus, for the sake of clarity and compactness, the details of the numerous known communication schemes will not be discussed in detail here. However, one of ordinary skill will appreciate that the wireless gateway may communicate by way of the cellular network under protocols defined within the various telecommunication standards, including but not limited to 3G, WiMAX, 4G-LTE, or the like.

One of ordinary skill will also appreciate that access to the cellular network infrastructure also integrates each sensor sub-network with the larger Internet 119. Accordingly, each wireless gateway may communicate through the cellular network-internet infrastructure in order to exchange data with the remote server network 107. In accordance with one or more embodiments, the remote server network 107 includes one or more remote data storage facilities 118, remote data server 121 that may itself include a local data storage facility 121a. In addition, the remote data storage facility 118 and remote data server 121 may be accessed by way of terminal 123, personal computer 125, or mobile computing device 127, e.g., a cellular phone, smart phone, tablet PC, or the like. As used herein, a data storage facility includes a cloud based remote data center, or any other system that includes network accessible memory locations. Accordingly, the data acquired by the wireless sensor modules may be easily accessible anywhere where internet access or cellular service is available. One of ordinary skill will appreciate that the system may also be deployed within smaller scale local area networks (LANs) or wide area networks (WANs) without departing from the scope of the present disclosure.

FIG. 2A shows an example of a wireless gateway for use in a system for field monitoring of stationary assets in accordance with one or more embodiments of the invention. The wireless gateway 201 includes an environmentally isolating enclosure 203. In accordance with one or more embodiments, the enclosure 203 is fabricated from a durable material that is able to withstand prolonged exposure to UV light, rain or snow, in addition to extreme temperature swings. In accordance with one or more embodiments, the enclosure 203 is fabricated from acrylonitrile butadiene styrene (ABS), polycarbonate, or any other similarly durable material. In addition, the enclosure 203 may further include a lid 205 and a body 207. The lid 205 and body 207 may be securely joined by any method known in the art, e.g., by way of screws (not shown), hinges, tongue and groove, attachments tabs/clips, ultrasonic welding, or the like. In accordance with one or more embodiments, the lid 205 and body 207 are sealed together by way of a silicone rubber gasket 209, or the like, as shown in cross the sectional view of FIG. 2B. In accordance with one or more embodiments, the enclosure 203 may have a NEMA 4 rating that conforms with Class I, Division II general oilfield use.

Furthermore, as shown in FIG. 2A, one or more embodiments of the wireless gateway may include a solar panel 211, integrated into a top surface of the lid 205 or side of the enclosure. The solar panel 211 may be attached within an access profile formed within a central portion of the lid or side of the enclosure, as shown in FIG. 2B. In another embodiment (not shown), the solar panel may fit into a recess milled within the top surface of the lid 205 or side of the enclosure. One of ordinary skill will appreciate that many different methods of mounting the solar panel within the enclosure are possible without departing from the scope of the present disclosure. One of ordinary skill will also appreciate that the size and shape of the enclosure may vary depending on the particular application. For example, higher power budgets may require a solar cell of relatively large surface area thereby requiring a large enclosure. In other embodiments that require less demanding power budgets, relatively small solar panels and, consequently, relatively small enclosures may be employed. In accordance with one or more embodiments, the power draw of the internal circuitry of the gateway module 215 is optimized to require a solar panel with a low power output.

FIG. 2C shows a block diagram of the internal hardware associated with a wireless gateway in accordance with one or more embodiments of the present invention. In this example, the wireless gateway includes power module 213 and gateway module 215. Power module 213 includes the solar panel 211 and a battery 217 for providing power to gateway module 215. Furthermore, in accordance with one or more embodiments, the power module 215 is configured to provide power to the gateway module 215 by way of battery 217 and to charge battery 217 by way of solar panel 211. In accordance with one or more embodiments, the battery 217 is charged without the need for a charge controller circuit 218.

In accordance with one or more embodiments, the battery 217 may be of the any suitable type, including, e.g., nickel metal hydride (NiMH) type, nickel cadmium, lithium ion, lithium ion phosphate type (lipo), and lithium thionyl type. The battery may be either a primary or secondary version that is, e.g., capable of continuous trickle charging via solar cell. For the sake of clarity, the power connections required to provide power from the power module 213 to the individual components of the gateway module 215 are not shown. However, one or ordinary skill will appreciate that each element of gateway module 215 is powered by power module 213 or from a suitable regulated power supply (not shown) within the gateway module 215 that itself is powered from power module 213.

In accordance with one or more embodiments, the output of the power module 213 is enabled or disabled by way of a proximity switch 219. In accordance with one or more embodiments, the proximity switch 219 is a magnetic reed switch that is configured in a normally open configuration. When placed in close proximity to a magnetic material, the proximity switch 219 forms a closed contact and activates the power output to the gateway module 215. Herein, the term magnetic material is used generally and refers to a material that produces a magnetic field in response to an applied magnetic field, e.g., various ferromagnetic materials. Accordingly, the wireless gateway 201 may power up automatically (i.e., without user input) when placed in the field, e.g., when mounted to an asset in the field made of a magnetic material. In one example, the gateway 201 may be affixed to a tank or vessel in the field, whose walls are formed of a magnetic material. Accordingly, the gateway 201 powers up immediately after the enclosure is affixed to the wall of the tank or vessel. Once power is established to the unit, a boot-up sequence begins and a connection procedure is initiated to automatically install the gateway into the network, as described in more detail below. No external power switch or user input is necessary to install the gateway 201 in the field and, thus, installation and replacement are greatly simplified as compared to existing devices.

In accordance with one or more embodiments, on an occasion when the gateway 201 is to be mounted to an asset formed from a non-magnetic material, e.g., a fiberglass tank, or the like, a magnetic token or plug may be affixed near the magnetic reed switch to induce the switching of the magnetic reed switch. Alternative, a capacitive, or other non-magnetic, proximity switch may be used to trigger the power up/boot sequence.

In accordance with one or more embodiments, a proximity sensor may be used to trigger an interrupt pin of the module's internal microcontroller (MCU), described in more detail below. In this embodiment, the gateway may be shipped to the end user in a deep power hibernation mode. If the proximity sensor is a magnetic reed switch, it may be configured to toggle the MCU into and out of full operation mode as the unit is placed in proximity of a ferromagnetic material such as a steel tank or structure. The unit will remain operating until the power is toggled again by touching it on a ferromagnetic object. This simplifies the installation on a non-magnetic material such as a fiberglass tank because it eliminates the requirement of attaching a magnetic token to the unit. It also allows the creation of a specialized computer algorithm to prevent accidental toggling on-or-off by requiring a certain timed interval to place the module in contact with the magnetic object to toggle the power. In accordance with one or more embodiments, the proximity sensor may be magnetic, capacitive, accelerometer, acoustic or any other type of sensor.

In order to simplify the installation of the gateway 201 even further, the enclosure may be affixed to the asset by way of a suitable high-bond double-sided tape, e.g., any tape having a durable, specialized multi-purpose adhesive. Due to the lightweight design of the modules themselves, such a tape may advantageously provide a durable and long-lasting attachment to the asset, even in the presence of foul weather, heat, and age. The size and weight of the gateway in accordance with one or more embodiments is dramatically lower than existing modules known in the art, which require complicated mounting stands and/or brackets for support and thus are not amenable to long-term or permanent mounting by this method. Of course, one of ordinary skill will appreciate that many different types of methods may be employed for mounting the enclosure and, accordingly, the present invention is not limited to any particular method disclosed herein.

FIG. 2C further shows that the gateway module 215 includes a proximity detector 220, an optional exciter 221, sensors 223a, 223b, . . . , 223n, cellular modem module 225, transceiver 227, microcontroller 229, which itself includes a processor 229a and memory 229b, as well as various analog and digital input and output lines as described in more detail below. In accordance with one or more embodiments, the cellular modem module 225 may further include a GPS module 231. The GPS module includes additional standard hardware, e.g., a GPS chipset, for geospatially locating the wireless gateway module 215. While shown as integrated into the cellular modem module 225, alternative embodiments may deploy a stand-alone GPS module.

The cellular modem module 225 may be of any type known in the art, and, in accordance with one or more embodiments may be a module optimized for use in machine-to-machine wireless networks (m2m). As used herein, the term cellular is not limited to modem modules that transfer data over the cellular band of 869 MHz-894 MHz. Rather, the term "cellular" also includes modules that may operate in any known band or set of bands, including, e.g., the 800 band, PCS band, 700 MHz band, 1.4 GHz band, AWS band, ISM bands or the BRS/EBS band. Accordingly, the cellular module 225 is equipped with antenna/antennas 225a operably connected to transceiver 227 for operation in the appropriate frequency band and for communication with the wider cellular network, using methods and protocols that are generally known in the art. Furthermore, while not explicitly shown in the drawing, the cellular modem module 225 further includes all the internal components of the typical cellular modem module. For details of one example, the reader is directed to the CC864-DUAL Hardware User guide 1vv0300791 Rev. 6-201202-13. One of ordinary skill in the art will appreciate that the above examples of cellular modem modules known in that art are provided merely by way of example and, thus, the present invention is not limited to only the cellular modem modules listed above, but rather, may employ any known or to be developed cellular modem module without departing from the scope of the present disclosure. Other wireless protocols may also be employed, such as Wireless Modbus, Fieldbus, PROFIBUS, WirelessHART, or ISA SP 100.11a protocols.

Returning to the description of the gateway module 215, the microcontroller 229 serves as the master controller for the gateway module 215. The microcontroller may be any microcontroller known, or to be developed in the art, e.g., the ATMEGA328P, which is an 8-bit AVR RISC-based microcontroller that includes 32 KB ISP flash memory with read-while-write capabilities, 1024B EEPROM, 2 KB SRAM, 23 general purpose I/O lines, 32 general purpose working registers, three flexible timer/counters with compare modes, internal and external interrupts, serial programmable USART, a byte-oriented 2-wire serial interface, SPI serial port, a 6-channel 10-bit A/D converter (8-channels in TQFP and QFN/MLF packages), programmable watchdog timer with internal oscillator, and five software selectable power saving modes. Other examples microcontrollers include the TI MSP430 series of MCU mixed signal processors. The microcontroller 229 is configured to receive sensor output from sensors 223a, 223b, . . . , 223n. In addition, microcontroller 229 is configured to interface with transceiver 227 in order to receive asset sensor data from remote wireless sensors (not shown).

In accordance with one or more embodiments, the remote wireless sensor modules and wireless gateways communicate by way of an RF protocol, preferably operating in one of the ISM bands. However, one of ordinary skill will appreciate that other frequency bands and protocols may be used including standard Zigbee, Wi-Fi, Bluetooth, or the like. The transceiver 227 may be any transceiver known or to be developed in the art, for example, the RFM12B or RFM22B, which are low cost ISM band frequency shift keying (FSK), Gaussian frequency shift keying (GFSK), and on-off keying (OOK) transceiver modules implemented with high resolution phase locked loops (PLL) working at signal ranges from the 433/868/915 MHZ bands. The transceiver 227 complies with FCC and ETSI regulation and, further may include the ability to transmit/receive over various carrier bands, e.g., in the case of the RFM12B, the device may be programed to operate in one of 255 separate bands, thus allowing the module to communicate with separate co-located sensor networks over 255 unique carrier frequency bands using antenna 227a. One of ordinary skill will appreciate that the number of sensors and bands is only limited by the choice of hardware and, thus, the particular hardware discussed herein and shown in FIG. 2 is not meant to limit the scope of the present invention to only the mentioned hardware, but rather, the above specific examples and specifications are provided merely by way of example. Furthermore, in accordance with one or more embodiments, more than one sensor module may share a single frequency band if time multiplexing is employed, as is known in the art. The transceiver 227 further includes interface 227b for communication with microcontroller 229.

In accordance with one or more embodiments, the sensors 223a, 223b, . . . , 223n may provide information relating to the environment surrounding the gateway module. While three sensors are shown in the example, one of ordinary skill will appreciate that any number of sensors may be used without departing from the scope of the present invention. For example, the sensors 223a, 223b, . . . , 223n may be temperature, pressure, and/or humidity sensors. In accordance with one or more embodiments, a precision linear active thermistor IC may be employed to take periodic temperature measurements. To improve accuracy and reduce cost of the wireless sensor modules in the field, the reading of the linear active thermistor IC in the gateway module may be used to calibrate the on-board CPU temperature readings of the wireless sensor modules, as described in more detail below.

The gateway 201 is further equipped with a proximity sensor 220 and an indicator unit 221 which are both configured to electrically communicate with the microcontroller 229. The indicator unit may be an acoustic exciter and/or a visual indicator, such as one or more light emitting diodes (LED's). In accordance with one or more embodiments, the proximity sensor 220 may operate in a proximity mode or in a physical touch mode. In proximity mode, the sensing element may be embedded within the enclosure, whereas in touch mode, a touch plate may be attached to the outside of the enclosure. Gateway 201 may be further configured to produce an audible signal from an audio exciter 221 regarding the health or configuration status of the module in response to user proximity and/or touch. For example, two long tones output from an audio exciter 221 may indicate a fully operational status, while a number of short bursts of sound may indicate a failure to communicate with one or more remote sensors or with the remote server. In another embodiment, the frequency of the tone may indicate the received signal strength from a wireless sensor module that is within range of the gateway. For example, a higher frequency audible tone may indicate high signal strength (good reception) and a lower frequency tone may indicate low signal strength (poor reception). Alternatively, indicator unit 221 includes of one or more high output LED indicator lights. In accordance with one or more embodiments, the indicators may be LED's of different colors that produce very high light intensities that are clearly visible even in direct bright sunlight. The light blinking, duration and color sequences can be programmed to provide diagnostic and informative information for the user.

Further, the proximity/touch sensor may be used to program the module itself. For example, touches by a user of different durations may initiate different diagnostic sequences or initiate a reprogramming of certain parameters of the system if desired. In accordance with another embodiment, indicator unit 221 employing an exciter may output a prerecorded audio track that is stored within the memory of microcontroller 329, or that is stored in separate external memory (not shown) that is operably connected to the microcontroller 329. In this example, the audio track may use spoken language to indicate the health of the module or the value of certain system parameters.

In accordance with one or more embodiments, the indicator unit 221 may use an exciter of the contact type. Generally speaking, a contact type exciter is a small form factor electrodynamic transducer, more or less a speaker without the cone. Accordingly, in one or more embodiments of the invention, the exciter 221 may be mounted directly to the solar panel 211, and, thus, the solar panel itself serves as the vibrating sound source, resonator, or effective speaker cone. Deploying the solar panel as the effective resonator results in suitable sound quality and also reduces the number of required system components and, thus, the overall cost and weight of the system.

FIGS. 3A-C show an example of a remote wireless sensor module for use in a system for remote stationary asset monitoring in accordance with one or more embodiments of the invention. As described below, many of the internal components of the remote wireless sensor module are common to the wireless gateway module and, thus, for completeness, some of the description found below is duplicative to that already presented above. Such duplicative information, where it occurs, is included below for the sake of completeness. In accordance with one or more embodiments, the remote wireless sensor module 301 is housed within an environmentally isolated enclosure 303. In accordance with one or more embodiments, the enclosure 303 is fabricated from a durable material that is able to withstand prolonged exposure to UV light in addition to extreme temperature swings. In accordance with one or more embodiments, the enclosure 303 is fabricated from acrylonitrile butadiene styrene (ABS), polycarbonate, or any other durable material. In addition, the enclosure 303 may further include a lid 305 and a body 307. The lid 305 and body 307 may be securely joined by any method known in the art, e.g., by way of screws (not shown), or the like. In accordance with one or more embodiments, the lid 305 and body 307 are sealed together by way of a silicone rubber gasket 309, or the like, as shown in cross the sectional view of FIG. 3B. Other embodiments can consist of two piece injection molded enclosures that may be fused together with glue or ultrasonic welding. For some applications a single-piece overmold configuration may be used. In any case, enclosure 303 may have a NEMA 4 rating that conforms with Class I, Division II general oilfield or hazardous agricultural use.

FIG. 3C shows a block diagram of a remote wireless sensor module 301 in accordance with one or more embodiments of the present invention. In this example, the remote wireless sensor module 301 includes power module 313 and wireless sensor electronics module 315. In accordance with one or more embodiments, power module 313 includes a battery 317 for providing power to wireless sensor electronics module 315. In addition to the battery, power module 313 may also include a solar panel (not shown) as described above with respect to the wireless gateway module. Furthermore, in accordance with one or more embodiments, the power module 315 is configured to provide power to the wireless sensor electronics module 315 by way of battery 317. In accordance with one or more embodiments, the wireless sensor module is in sleep more than 99% of the time as discussed in more detail below in reference to FIG. 4 and such a wireless sensor module may run for over three years using only 4 AA batteries. One of ordinary skill in that art will appreciate that the number and type of batteries will vary according to the power budget of the specific type of sensors being deployed with some sensors requiring solar assist in a manner similar to that described above in reference to the wireless gateway module.

In accordance with one or more embodiments, the battery 317 may be of the nickel metal hydride (NiMH) type, lithium ion phosphate type (lipo), and lithium thionyl type. In particular, lithium thionyl batteries have proven to provide an extremely high power density and a suitable single cell operating voltage of 3.6V. Accordingly, a single lithium thionyl battery is capable of reaching internal processor and RF operating voltages. For the sake of clarity, the power connections required to provide power from the power module 313 to the individual components of the wireless sensor electronics module 315 are not shown. However, one or ordinary skill will appreciate that each element of wireless sensor electronics module 315 is powered by power module 313.

In accordance with one or more embodiments, the output of the power module 313 is enabled or disabled by way of the proximity switch 319. In accordance with one or more embodiments, the proximity switch 319 is a magnetic reed switch that is normally open. However, when placed in close proximity to a magnetic material, the proximity switch 319 forms a closed contact and activates the power output to the wireless sensor electronics module 315. Herein, the term magnetic material is used generally and refers to a material that produces a magnetic field in response to an applied magnetic field, e.g., various ferromagnetic materials. Accordingly, the remote wireless sensor module 301 may power up automatically (i.e., without user input) when placed in the field, i.e., when mounted to an asset made of a magnetic material. In one example, the wireless sensor module 310 may be affixed to a tank in the field, having walls made from a magnetic material. Accordingly, the remote wireless sensor module 301 powers on immediately after the enclosure is affixed to the wall of the tank and begins a boot up and connection procedure to automatically configure itself to communicate with the wireless gateway module, as described in more detail below. No external power switch or user input is necessary to install the remote wireless sensor module 301 in the field and, thus, installation and replacement become greatly simplified.

In accordance with one or more embodiments, on an occasion when the remote wireless sensor module 301 is proximate to an asset formed from a non-magnetic material, e.g., a fiberglass tank, or the like, a magnetic token or plug, may be affixed near the magnetic reed switch to induce the switching of the magnetic reed switch. Alternative, a capacitive, or other non-magnetic, proximity switch may be used to trigger the power up/boot sequence. Furthermore, to simplify the installation of the remote wireless sensor module 301 even further, the enclosure may be affixed to the asset by way of a suitable double sided tape, e.g., as described above in reference to FIG. 2. Due to the lightweight design of the modules themselves, such a tape provides for a durable and long-lasting attachment to the asset, even in the presence of foul weather, heat, and age. Of course, one of ordinary skill will appreciate that many different types of methods may be employed for mounting the enclosure and, accordingly, the present invention is not intended to be limited to any particular method disclosed herein.

In accordance with one or more embodiments, the magnetic proximity switch may be used to trigger an interrupt pin of the remote wireless sensor's internal microcontroller (MCU), rather than being used as a primary power switch. In this embodiment, the remote wireless sensor module may be shipped to the end user in a deep power hibernation mode. The magnetic proximity switch can be configured to toggle the MCU into and out of full operation mode as the unit is placed in proximity of a ferromagnetic material such as a steel tank or structure. The unit will remain operating until the power is toggled again by touching it on a ferromagnetic object. This simplifies the installation on a non-magnetic material such as a fiberglass tank because it eliminates the requirement of attaching a magnetic token to the unit. It also allows the creation of a specialized computer algorithm to prevent accidental toggling on-or-off by requiring a certain timed interval to place the module in contact with the magnetic object to toggle the power.

FIG. 3C further shows that the wireless sensor electronics module 315 includes a proximity detector 320, an optional exciter 321, sensors 323*a*-323*c*, transceiver 327, microcontroller 329, which itself includes, a processor 329*a* and memory 329*b*, as well as various analog and digital input and output lines as described in more detail below. Optionally, the wireless sensor electronics module 315 also includes a GPS receiver/chipset (not shown) configured to allow the device to be location aware, i.e., to have the ability to auto-geolocate and to install itself into the wireless sensor network, as described in more detail below.

Returning to the description of the wireless sensor electronics module 315, the microcontroller 329 serves as the master controller for the wireless sensor electronics module 315. Accordingly, the transceiver 327 includes interface 327*b* for communication with and for programming by way of the microcontroller 329. The microcontroller may be any microcontroller known in the art, e.g., as described above in reference to FIGS. 2A-2C. The microcontroller 329 is configured to receive sensor output from sensors 323*a*-323*c*. In addition, microcontroller 329 is configured to interface with transceiver 327 in order to transmit to the wireless gateway module any acquired asset data as received from sensors 323a-323c.

In accordance with one or more embodiments, wireless sensor electronics module 315 communicates with the wireless gateway module by way of an RF protocol, preferably operating in one of the ISM bands. However, one of ordinary skill will appreciate that other frequency bands may be used including standard Zigbee, Wi-Fi, and Bluetooth. The transceiver 327 used for the communication may be any transceiver known in the art, as described above in reference to FIGS. 2A-2C. For example, the RFM12B or RFM 22B, which are low cost ISM band frequency shift keying (FSK), Gaussian frequency shift keying (GFSK), and on-off keying (OOK) transceiver modules implemented with high resolution phase locked loops (PLL) working at signal ranges from the 433/868/915 MHZ bands. The transceiver 327 complies with FCC and ETSI regulation and, further may include the ability to transmit/receive over various carrier bands, e.g., in the case of the RFM12B, the device may be programed to operate in one of 24 separate bands, thus allowing the module to communicate with 24 separate sensors over 24 unique carrier frequency bands using antenna 327a.

One of ordinary skill will appreciate that the number of sensors and bands is only limited by the choice of hardware and, thus, the particular hardware discussed herein and shown in FIG. 3 is not meant to limit the scope of the present invention to only the mentioned hardware but rather, the above specific examples and specifications are provided merely by way of example. Furthermore, in accordance with one or more embodiments, more than one sensor module may share a single frequency band if time multiplexing is employed, as is known in the art. The transceiver 327 further includes interface 327b for communication with microcontroller 329. In addition, while one way communication between the wireless sensor modules 315 and the wireless gateway is described in the above example, one of ordinary skill will appreciate that two-way communication between the gateway and sensor is possible and sensor-to-sensor communication is possible without departing from the scope of the present disclosure. Furthermore, sensors and/or gateways may communicate with one or more intermediate repeater modules, if necessary.

In accordance with one or more embodiments, the sensors 323a-323c may provide information relating to the asset being monitored by the remote wireless sensor module, as described in more detail below. For example, the remote wireless sensor module may be a fluid level detector mounted to a fluid tank, an accelerometer/orientation detector, mounted to a beam pump or level control system. Other sensor types include, e.g., microphones and magnetometers. While three sensors are shown in the example, one or ordinary skill will appreciate that any number of sensors may be used without departing from the scope of the present invention. For example, the sensors 323a, 323b, . . . 323n may be sensors designed to measure temperature, pressure, acceleration, magnetic field, electric field, humidity, or any other known sensor. In accordance with one or more embodiments, the temperature of the remote wireless sensor electronics module 315 may be monitored by way of the on-board CPU temperature readings. To improve accuracy, the value of these temperature sensors may be correlated with a high-precision thermistor IC deployed within the wireless gateway module as described above in reference to FIG. 2. Alternatively, the sensor units may include high-precision thermistor ICs directly onboard.

The remote wireless sensor module 301 is further optionally equipped with a proximity sensor 320 and an indicator unit 321 both of which are configured communicate with the microcontroller 329. The indicator unit may be an acoustic exciter and/or a visual indicator, such as one or more light emitting diodes (LED's). In accordance with one or more embodiments, the proximity sensor 320 may operate in proximity mode or physical touch mode. In proximity mode, the sensing element may be embedded within the enclosure, whereas in touch mode, a touch plate may be attached to the outside of the enclosure. Sensor module 301 may be further configured to produce an audible signal from an audio exciter 321 regarding the health or configuration status of the module in response to user proximity and/or touch. For example, two long tones output from an audio exciter 321 may indicate a fully operational status, while a number of short bursts of sound may indicate a failure to communicate with one or more remote sensors or with the remote server. In another embodiment, the frequency of the tone may indicate the received signal strength from a wireless sensor module that is within range of the gateway. For example, a higher frequency audible tone may indicate high signal strength (good reception) and a lower frequency tone may indicate low signal strength (poor reception). Alternatively, indicator unit 321 includes of one or more high output LED indicator lights. In accordance with one or more embodiments, the indicators may be LED's of different colors that produce very high light intensities that are clearly visible even in direct bright sunlight. The light blinking, duration and color sequences can be programmed to provide diagnostic and informative information for the user.

Further, the proximity/touch sensor may be used to program the module itself. For example, touches by a user of different durations may initiate different diagnostic sequences or initiate a reprogramming of certain parameters of the system, if desired. In accordance with another embodiment, the indicator unit 321 employing an exciter may output a prerecorded audio track that is stored within the memory of microcontroller 329. In this example, the audio track may use spoken language to indicate the health of the module or the value of certain system parameters.

In accordance with one or more embodiments, the indicator unit 321 may employ an exciter of the contact type, also known as an exciter. Generally speaking, an exciter is a small form factor electrodynamic transducer, more or less, a speaker without the cone. Accordingly, in one or more embodiments of the invention, the exciter 321 may be mounted directly to the lid 305 of the enclosure 303, and, thus, the lid itself serves as the vibrating sound source. More specifically, a portion of an inner surface 323 the lid 305 may be milled to form a notched portion 325 for housing the exciter 321. Accordingly, a thin portion of the lid 305 directly above the notch portion 325 serves as an effective resonator for generating sound by way of the exciter 321. Deploying the thin portion of the thin 305 as the effective speaker cone results in suitable sound quality and also reduces the number of required system components and, thus, the overall cost and weight of the system.

Figure 4:
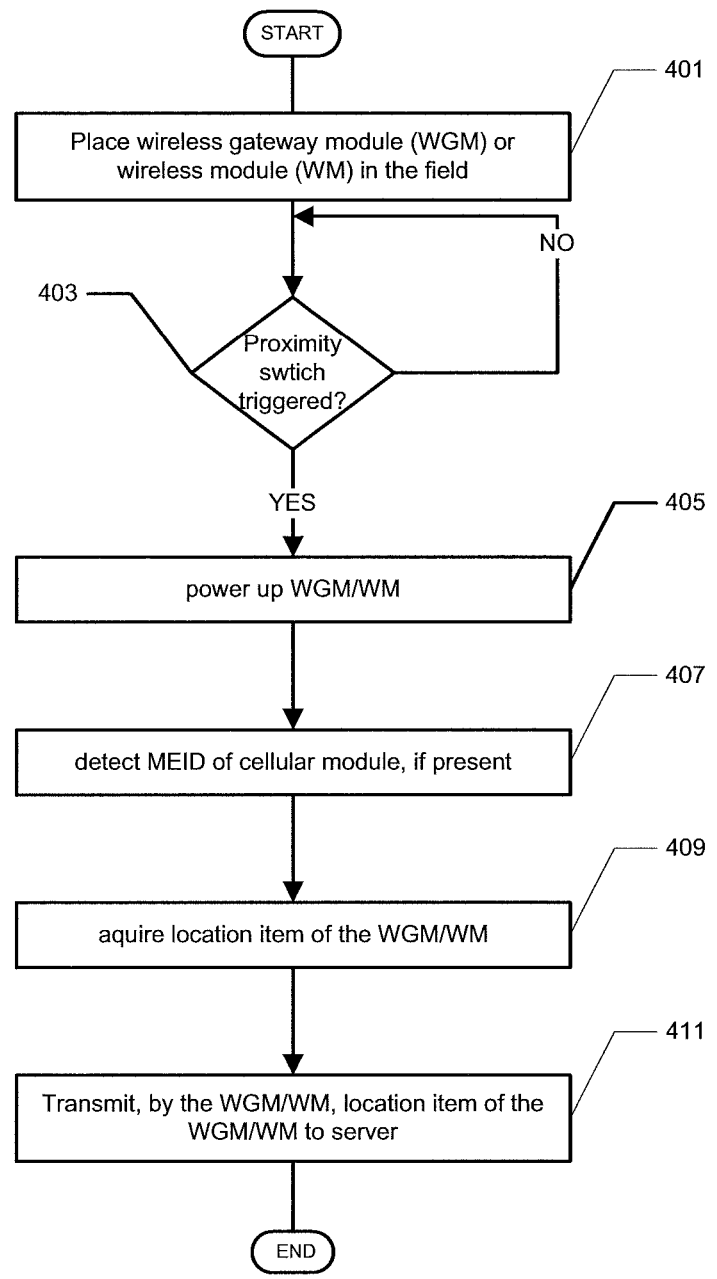
FIG. 4 shows a flowchart describing a gateway-side auto-initialization method for initializing a wireless gateway at a monitoring site including a stationary asset, in accordance with one or more embodiments of the invention.

FIG. 4 shows a flowchart describing an auto-initialization method for initializing a wireless gateway at a monitoring site including a stationary asset, in accordance with one or more embodiments of the invention. At step 401, the wireless gateway module is placed in the field. For example, a service person may enter the field and affix the wireless gateway module to a convenient stationary asset by way of a suitable double sided high-adhesive tape. In accordance with one or more embodiments of the present invention, the design of the wireless gateway module makes this installation extremely simple. For example, in one embodiment, all that is required is that the service person remove a protective film from the adhesive tape and affix the wireless gateway module to the stationary asset; the remainder of the installation process is accomplished automatically. Once affixed to the asset, the proximity switch is automatically triggered at step 403. For example, in one embodiment, the proximity switch is a magnetic reed switch that is normally open. However, when placed in close proximity to a magnetic material, the proximity switch forms a closed contact and activates the power output to the gateway module. Accordingly, the wireless gateway module powers up automatically (i.e., without user input) when placed in the field, e.g., when mounted to an asset in the field made of a magnetic material. In one example, the wireless gateway module may be affixed to a vessel containing fluid to be monitored in the field, wherein the walls of the vessel are formed of a magnetic material. Accordingly, at step 405, the gateway powers up immediately after the enclosure is affixed to the wall of the vessel. At step 407, the internal cellular module of the gateway begins its boot sequence and the hardware identification information is acquired, e.g., a mobile equipment identifier (MEID), or the like. After the cellular module concludes is boot sequence, the cellular module acquires a location item of the wireless gateway at step 409. The location item includes the GPS coordinates of the wireless gateway. At step 411, the wireless gateway appends the MEID and the location information and transmits the combined information to a remote server for storage and/or further processing.

Figure 5:
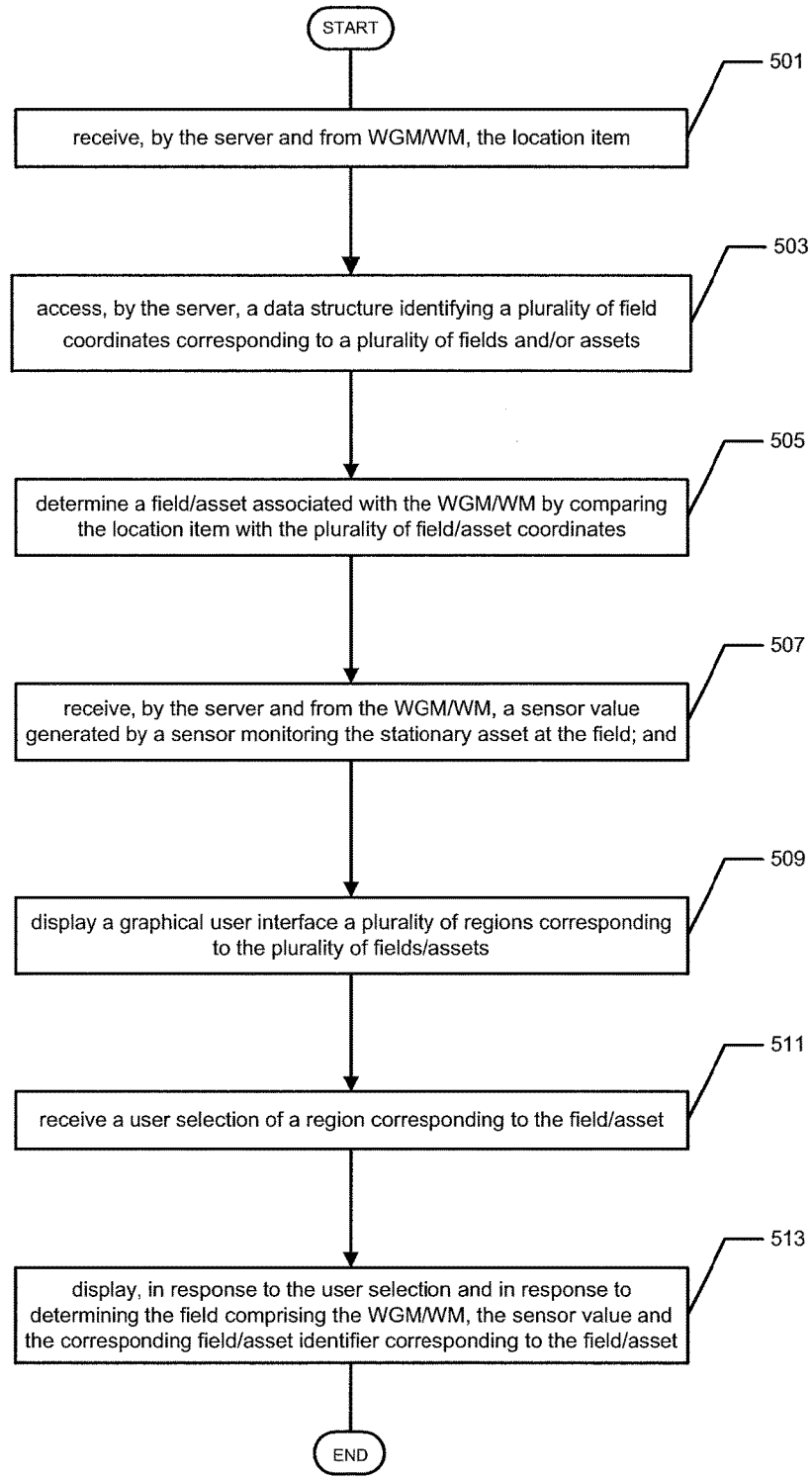
FIG. 5 shows a flowchart describing a server-side auto-initialization method for initializing a wireless gateway at a monitoring site including a stationary asset, in accordance with one or more embodiments of the invention.
Figure 7:
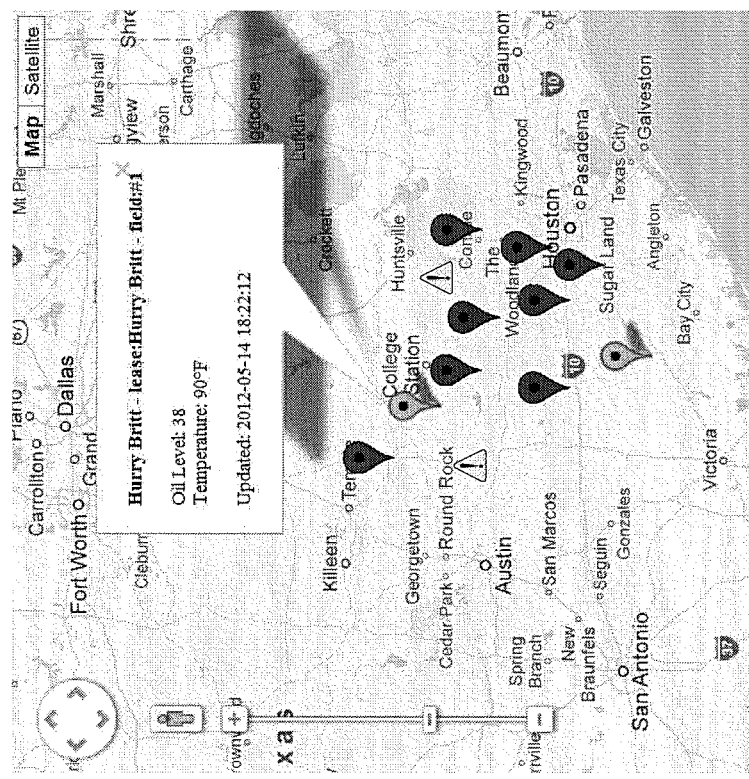
FIG. 7 shows one example of a graphical user interface in accordance with one or more embodiments of the invention.

FIG. 5 shows a flowchart describing an auto-initialization method for initializing a wireless gateway at a monitoring site including a stationary asset, in accordance with one or more embodiments of the invention. More specifically, FIG. 5 shows a method for automatically geolinking a wireless gateway that is placed in a field for monitoring a stationary asset. In this example, the processing is by a remote server after the location item geostamped MEID geostamped MEID is transmitted from the wireless gateway module to the remote server. At step 501, the server receives the geostamped MEID that includes the GPS coordinates of the wireless gateway module and the MEID of the wireless gateway module. At step 503, the server accesses a data structure in memory that identifies a plurality of field coordinates corresponding to a plurality of fields. For example, referring to FIG. 1, the data structure may be stored in the remote data storage facility 119 and/or the local data storage facility 121a. The data structure may include a number of field coordinates and field identifiers, i.e., names of fields. For example, in the case of oilfield monitoring of n fields, the database may include the names of all the field, e.g., field F1, field F2, field F3, . . . , field $F_n$. Furthermore, with each field is an associated location information item which includes latitude and longitude coordinates corresponding to each field, as shown in FIG. 7. In accordance with one or more embodiments, these field location information items were previously stored in the data storage facility through, e.g., user input or a previous survey done by a service person.

Returning to the method of FIG. 5, in step 505 the server automatically determines the field where the wireless gateway is located by comparing the GPS coordinates of the geostamped MEID of the wireless gateway with each of the field coordinates. For example, in accordance with one or more embodiments, the server may compute the distance between each stored field location item and the GPS coordinates of the wireless gateway module and then associate the wireless gateway with the field that is nearest to the wireless gateway module. For example, the distance between a newly installed wireless gateway module having GPS coordinates (Lat_1,Long_1) and a field $F_M$ having coordinates (Lat_M, Long_M) may be computed as $$D_{M1}=\sqrt{(\text{Lat\_}M-\text{Lat\_}1)^2+(\text{Long\_}M-\text{Long\_}1)^2}$$

Accordingly, the server may compute the distance between the newly installed gateway M and every field, F1-FN, and select the field nearest to the newly installed gateway as the field to associate the gateway with. As used herein, the term association refers to the linking by the server of the predetermined field data structure with the geostamped MEID and thus, the newly installed gateway. Accordingly, every measurement made by a wireless sensor module associated with the gateway's MEID, may be automatically associated with a predetermined stationary asset in the field. FIG. 7 shows one example of a result of GPS based linking of a newly installed wireless gateway.

Returning to FIG. 5, in step, 507, the server receives one or more sensor values generated by the wireless sensors mounted to the stationary assets in the field. Because the wireless gateway has been linked with a field having known stationary assets, the sensor values may also be automatically linked, by the server, with existing assets in the field. Thus, in accordance with one or more embodiments, a map, or other user interface such as a table, may be displayed to a user at step 509. In the example of a map display, the map includes a plurality of regions, each region corresponding to one of the plurality of fields. In step 511, the user may then select a region corresponding to one of the fields, for example, using a user interface device such as a mouse, touch-screen, keyboard, or the like. In step 513, in response to the user selection, the sensor values corresponding to selected field are displayed in addition to the field identifier, e.g., F1. In another embodiment, the user interface may be in the form of a table that includes information identical to that displayed in the map but in tabular form.

Figure 6:
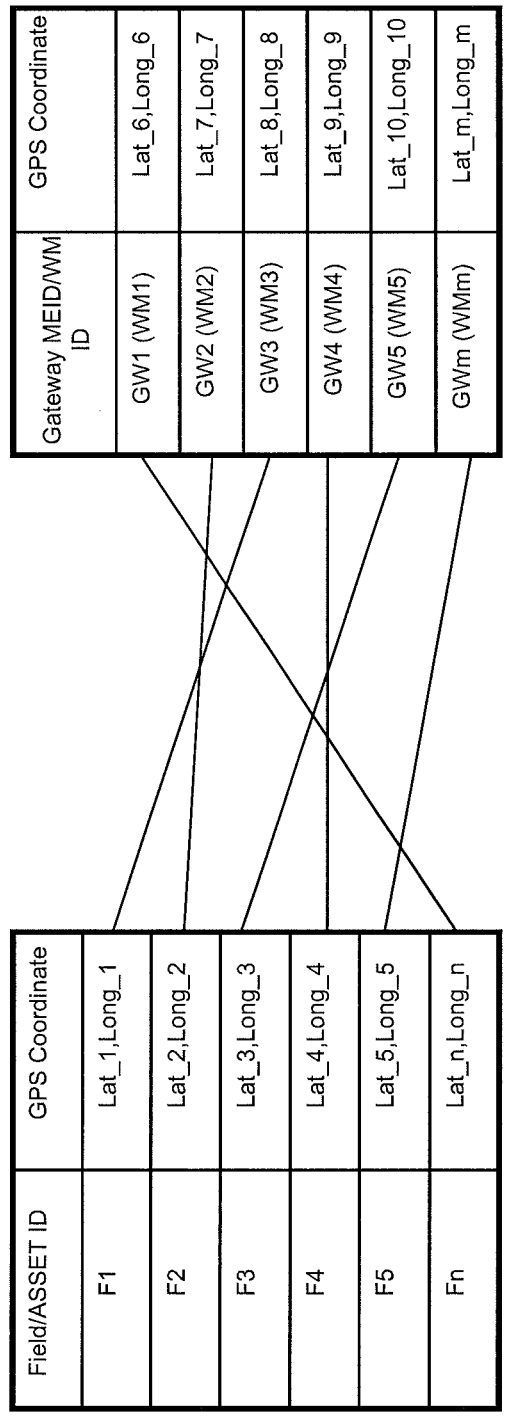
FIG. 6 shows one example of a result of GPS based linking of a newly installed wireless gateway or wireless module in accordance with one or more embodiments of the invention.

While the description above is focused on an example of gateway modules associating with particular fields, alternate embodiments may generally associate any module (WM) with any predetermined set of coordinates stored on the remote server. For example, as shown in FIGS. 4-6, a wireless module (WM), such as a sensor module may also include GPS capabilities and the server may include coordinates of actual assets in a field. Thus, in this embodiment, the individual location items of wireless modules (WMs) may be automatically associated, or linked with individual assets (using a plurality of asset coordinates stored in the remote server, generally in an identical manner to that described above for field coordinates), more specifically, in a manner identical to that described above with respect to gateway modules automatically associating (or linking) with fields.

FIG. 7 shows one example of a graphical user interface in accordance with one or more embodiments of the invention. As shown in the FIG. 6, a map is displayed with the map including regions 701 that correspond to any number of fields being monitored. The regions also include icons indicating the location and/or status of any particular field. For example, green icons may include fields having no active alarm states, while red icons or exclamation icons may indicate one or more active alarm states. The size, shape and color of the icons used in this particular example map are meant only as examples and, thus, one of ordinary skill having the benefit of this disclosure will appreciate that innumerable different types of icons or indicator may be used without departing from the scope of the present disclosure. As described above, in response to a user input, e.g., a mouse click or finger touch made in a map region that includes an indicator corresponding to a field, the sensor values for one or more stationary assets located in the field will be displayed. In the example shown in FIG. 6, Field #1 is displayed and two sensor values associated with a stationary asset are displayed: the current temperature and the oil level in an oil tank. As described above, these sensor values may originate from one or more wireless sensor modules in the field and transmitted to the remote server by way of a wireless gateway co-located in the field with the stationary asset being monitored.

Advantageously, the above described GPS based autolinking of the wireless gateway allows for nearly automated installation or replacement of a wireless gateway in a field. For example, a new wireless gateway may be simply affixed to a stationary asset by a service person. Once affixed, the wireless gateway will automatically power on, initiate a boot sequence, acquire its GPS coordinates and transmit the GPS coordinates to the remote server. The server then will automatically associate the gateway with an existing field and field location based on the location of the gateway. Accordingly, a user of the remote server need not provide any server side installation or user input. Rather, the sensor values are automatically made available to the user of the GUI by way of the auto-linking GPS procedure. Of course, if necessary, and if the location of a newly installed gateway is known, the user may alternately manually link a field to the newly installed wireless gateway by manually entering the field identification information, MEID, and location of the gateway into the server.

In accordance with one or more embodiments, the procedure of auto-linking the wireless gateway may be extended to the sensor modules as well. In one embodiment, a sensor module may have onboard GPS units themselves, and can link and associate the same way as described above for the gateways. In another embodiment, the system can assign approximate GPS locations for a sensor by using the GPS location data of the gateway or gateways it transmits to. In yet another embodiment, a field user can register or assign data to a sensor, repeater or gateway using a smart cellphone, tablet or portable computer. The phone can scan a bar code or quick response (QR) code on the device label, which uploads the unit ID and any additional data to the phone. Another option is for a near field communication (NFC) such as radio frequency ID (RFID) between the device and phone. Accordingly, the user can manually add additional data on the spot. In addition, a phone's own GPS position, if available in the cellphone hardware, may be automatically added to the device data so that its unique GPS position may be uploaded wirelessly into the device database.

Further to the previous example of uploading device information, a smart cellphone, tablet or portable computer may be used to display the current or near real-time data transmitted by a wireless sensor, repeater or gateway. For instance, by touching the sensor, repeater or gateway device in a programmed manner, the device can be instructed to immediately transmit its most recently acquired data to the online database, which can then immediately transmit the information directly to the user's cellphone or computer for display. In this manner the user's cellphone or computer may be used as a virtual sensor display device. This eliminates the need for incorporating complex or costly display elements on the modules. In addition, along with the internal antenna and proximity sensor features, the enclosures will enjoy maximum durability and weatherablity by minimizing penetrations, attachments and breaches of the enclosure surfaces.

Figure 8C:
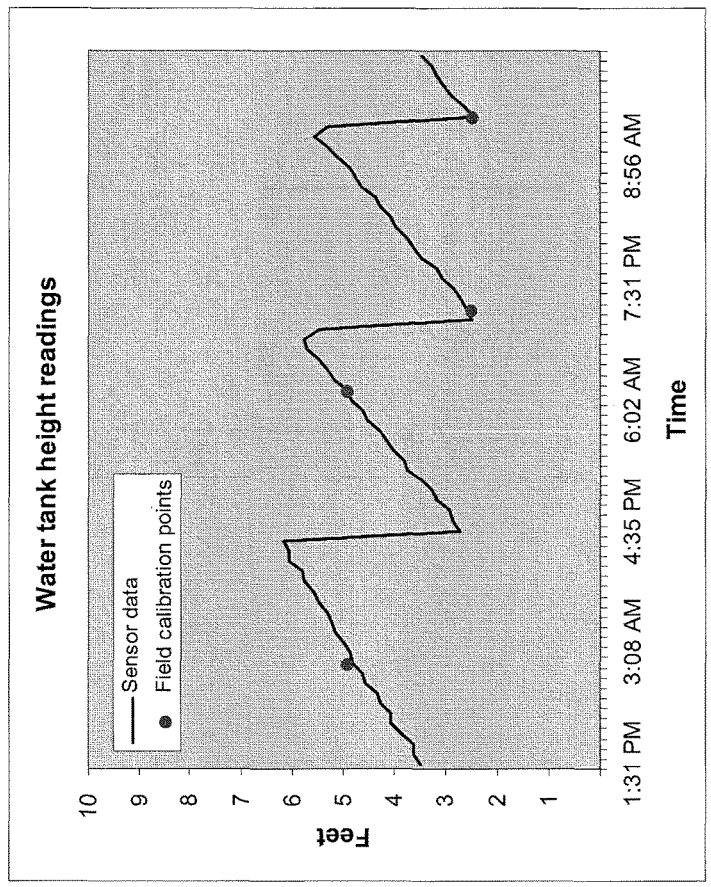
FIGS. 8A-8C show examples of a remote sensor calibration procedure in accordance with one or more embodiments of the invention.
Figure 8A:
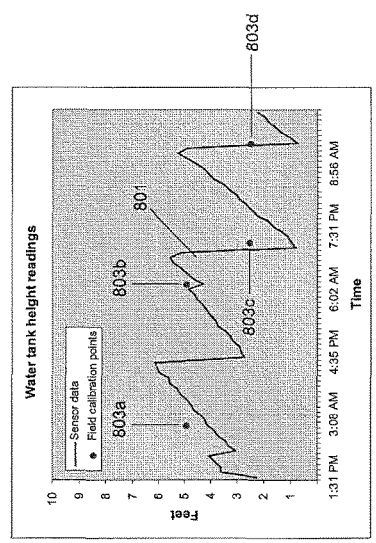
Figure 8B:
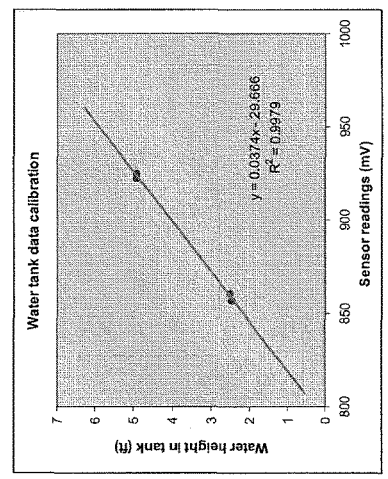

FIGS. 8A-8C show examples of a remote sensor calibration procedure in accordance with one or more embodiments of the invention. More specifically, FIG. 8A shows an example plot that includes uncalibrated sensor data 801, in this example tank level sensor data, and four calibration points 803*a*-803*d*. In accordance with one or more embodiments, the calibration points may be obtained by service personnel in the field. In this example, a service person may visit the asset being monitored and take one or more level readings and correlate those level readings with an output value of the sensor. For example, the service person may take four level readings with a calibrated level sensor and note the time at which these measurements are made. Of course, the above example uses four readings but any number of calibration readings may be made. One of ordinary skill will recognize that the calibrated level sensor may be any calibrated sensor known in the art, ranging from pressure, acoustic, or the like, to more simple methods such as a simple visual inspection of the of the height/depth of the fluid in the tank. One of ordinary skill will also appreciate that the level sensor may be calibrated in relative terms, i.e., a sensor output value may be correlated to a 100 percent fill level, 50 percent fill level, 10 percent fill level, or the like.

In accordance with one or more embodiments, once the fill levels, sensor values, and measurement times are known, the service person may input these values in a mobile device such as a mobile telephone, smart phone, tablet or computer, or the like. The values are then transmitted via the cellular network to the remote server where they are stored in memory and used by the remote server to compute a calibration curve 805. In one example, where internet access is available to the mobile device, the fill levels and sensor values may be transmitted by way of IP data packets to the remote server. Alternatively, the fill levels and sensor values may be transmitted by SMS, or the like. More generally, the fill levels and sensor values may be transmitted from the mobile device to the remote server by any communication method or protocol known in the art.

FIG. 8B shows an example of a linear sensor calibration curve 805 computed by the remote server in accordance with one or more embodiments of the invention. Advantageously, the remote server may be pre-programed with the necessary software to automatically fit the calibration points provided by the service person without any additional input from the service person, other than the calibration points themselves. In the example shown in FIG. 8B, the calibration curve is generated by first associating the measured calibration points with one or more uncalibrated sensor values using the time of measurement to select these uncalibrated sensor values out of a time series of uncalibrated data. Alternatively, or course, the service person may also log the values of the uncalibrated sensor at the same time the calibrated values are obtained in the field. Next, the server fits the calibration data to a linear calibration model and the fit parameters of the calibration model (e.g., slope, y-intercept, and $R^2$ value) are used to convert existing and future sensor values to calibrated sensor values.

One of ordinary skill will appreciate that many different numerical fitting routines can be employed in the above fitting procedure and, accordingly, the calibration curve may be obtained any number of ways without departing from the scope of the present disclosure. Furthermore, depending on the nature of the sensor response, nonlinear fit routines, e.g., nonlinear least squares, and nonlinear calibration curves may be employed, e.g., polynomial fits, or the like. FIG. 8C shows an example of the data from FIG. 8A that has been remotely calibrated using the calibration curve 805 generated by the remote server to produce the calibrated data 807.

In accordance with one or more embodiments, both the calibration points and the sensor data may be stored in memory at a data storage facility that is accessible by, or co-located with, the remote server. Thus, calibration points that are taken by a service person may be accumulated over time and one or more of the points may be used by the server to refit new, or previously existing and stored sensor data to further increase the accuracy of the calibration in real time. In accordance with one or more embodiments, the calibration points taken by the service person may also be time stamped. Accordingly, the particular calibration points used by the server to generate the calibration curve may be chosen by the server or manually by a user based upon a certain time criteria or range of time criteria. For example, when a service person replaces a defective sensor with a new sensor, the set of calibration points may be chosen as all points having a time stamp starting shortly after the installation of the new sensor. Alternatively the server may be programmed to choose a set of most recent calibration points based on time and date in order to improve the accuracy of the remote calibration in a situation where the calibration of the sensor is known to drift slowly over time such that old calibration points are no longer accurate. In other embodiments, all, or a subset of, the calibration points may be weighted according to their age and processed by the server using a numerical fitting routine that employs weighted fitting, e.g., a numerical weighted least squares fit.

Figure 9:
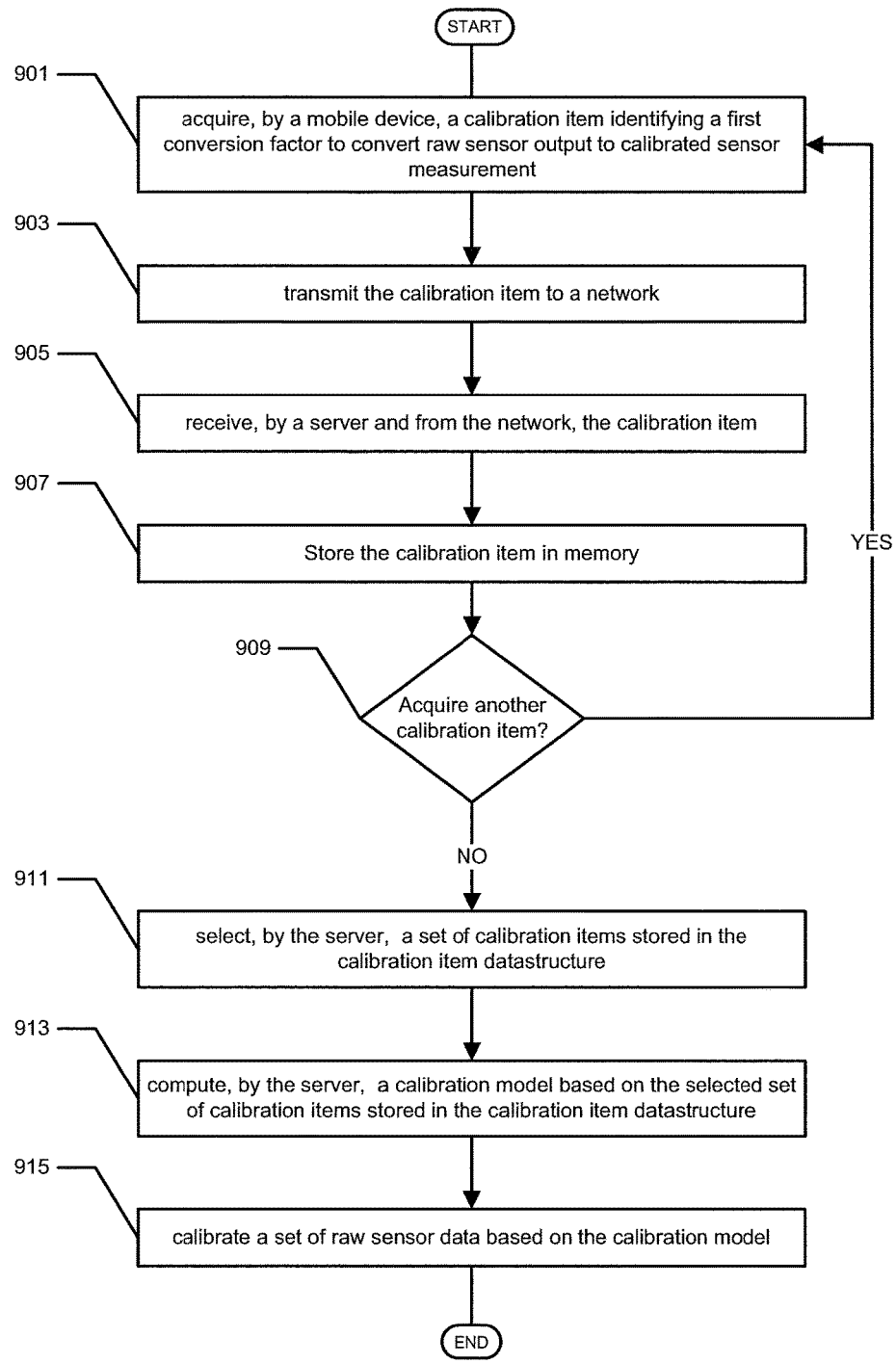
FIG. 9 shows a flowchart describing a method for remote sensor calibration, in accordance with one or more embodiments of the invention.

FIG. 9 shows a flowchart describing a method for remote sensor calibration, in accordance with one or more embodiments of the invention. In step 901, a service person may manually acquire a calibration item by measuring a property of the stationary asset being monitored with a previously calibrated sensor. For example, the calibration item may be a conversion factor for converting raw sensor output (e.g., volts) to a physical quantity being monitored such as tank fill level (e.g., feet of fluid, or percent full/empty). Alternatively, a calibration item may be a fill level and a time that may be later automatically associated with a remote sensor value by the server using the respective timestamps of the fill level and the sensor value. After acquiring the calibration item, the service person may enter the value of the calibration item into a mobile device, e.g., a mobile phone, tablet PC, laptop PC, or the like. In step 903, the mobile device communicates, or transmits, the calibration item to a network. In step 905, a remote server receives the calibration item from the network. In step 907, the calibration item is stored in the memory of a storage facility that is accessible by the remote server. One of ordinary skill will appreciate that the calibration item may be stored in memory that is co-located with the server or may be transmitted from the mobile device directly to a third party storage location which is accessible by the server, e.g., using a cloud service provider. In step 909, if the service person wishes to acquire another calibration item, steps 901-907 are repeated.

In step 911, the server selects a set of calibration items stored in memory. This set of calibration items may be chosen by hand by a user or determined automatically by the server based upon preprogrammed conditions, e.g., by time, as described above. In step 913, the server computes, using the selected set of calibration items, a calibration model. For example, the calibration model may be a linear or nonlinear fit to the calibration points as described above in reference to FIGS. 8A-8C. In step 915, using the calibration model, the sever then calibrates the set of raw sensor data as described above in reference to FIG. 8A-8C. For example, the server, using the model, may convert raw sensor values (in, e.g., volts) to a physical value (e.g., temperature, fill level, etc.).

FIG. 10A shows an example of sensor modules as described above in reference to FIGS. 3A-3C. Specifically, the wireless sensor modules are adapted as a system 1001 for wirelessly monitoring a fill level in a vessel in accordance with one or more embodiments of the invention. The system 1001 includes two sensor modules: an acoustic impulse generator 1003 and an acoustic impulse receiver 1005. Both the acoustic impulse generator 1003 and the acoustic impulse receiver 1005 may be attached to the outer surface of a vessel 1007. In accordance with one or more embodiments, the vessel 1007 may be a fluid tank, e.g., a fuel tank, oil tank, water tank, or any other tank used to house fluids. The acoustic impulse generator 1003 and receiver module 1005 may include one or more of the internal components described above in reference to FIGS. 3A-3C, in addition to several internal components specifically adapted for fluid level measurement, as described in more detail below. Furthermore, as the acoustic impulse generator 1003 and acoustic impulse receiver 1005 may be wireless sensor modules, the acoustic impulse generator 1003 and acoustic impulse receiver 1005 may also be configured to communicate with a wireless gateway module as described above. In accordance with one or more embodiments, not only may the acoustic impulse generator 1003 and acoustic impulse receiver 1005 each communicate with a wireless gateway, but the acoustic impulse generator 1003 and acoustic impulse receiver 1005 may communicate with each other, either wirelessly or by wire, in order to make a fluid level measurement, as described in more detail below.

In accordance with one or more embodiments, the acoustic impulse generator 1003 generates an acoustic impulse 1009 which travels along the wall of the vessel 1007. A short time after generation of the acoustic impulse 1009, the acoustic impulse 1009 reaches the acoustic impulse receiver 1005 where the pulse is detected by acoustic detection circuitry, e.g., a microphone, or any other detector adapted to detect acoustic signals. Generally speaking, the level of fluid in the vessel may be determined by the travel time of the acoustic impulse between the impulse generator 1003 and the acoustic impulse receiver 1005. Alternatively, the level of fluid in the vessel may be determined by properties of the acoustic impulse received at the acoustic impulse receiver 1005, as described in more detail below, e.g., using a characteristic of acoustic impulse spreading (dispersion) measured at the receiver.

FIG. 10B shows an example of the acoustic response within the wall of a vessel in accordance with one or more embodiments of the invention. More specifically, in response to the action of an acoustic impulse generator, e.g., impulse generator 1003 shown in FIG. 10A, an acoustic impulse 1011a propagates along a wall of the vessel. As shown in FIGS. 10A-10B, the impulse generator 1003, or more precisely, the acoustic sensor of the impulse generator 1003, is located at a height $z_1$ on the vessel. The acoustic impulse receiver 1005, or more precisely, the acoustic sensor of the acoustic impulse receiver 1005, is located some distance away, at a height $z_2$ on the tank. One of ordinary skill in the art will appreciate that the locations of acoustic impulse generator 1003 and acoustic impulse receiver 1005 may be interchanged or varied without departing from the scope of the present disclosure. In the example shown in FIG. 10B, an acoustic impulse including a wave packet 1011a is initiated at a time $t=t_1$. As the acoustic impulse propagates along the tank, the wave packet 1011*a* disperses (spreads) as shown by the snapshots shown at times $t_2$, $t_3$, and $t_4$, showing dispersing wave packets 1013, 1014, and 1015, respectively. As the impulse packet 1010 disperses, it separates into two packets which become more distinct with time. These packets may be, e.g., the preflexural (dilational, or compressional) wave and the flexural (rotational, or shear) waves, respectively. These packets separate in space (i.e., along the height of the tank) as they travel along the wall of the tank, as shown in FIG. 10B and are tracked in the figure by trajectories 1017 and 1019. The velocity of the pre-flexural waves are not substantially affected by the presence of fluid in the vessel, and the pre-flexural waves travel substantially faster than the flexural waves as indicated by trajectories 1017 and 1019 shown in FIG. 10B.

Figure 11:
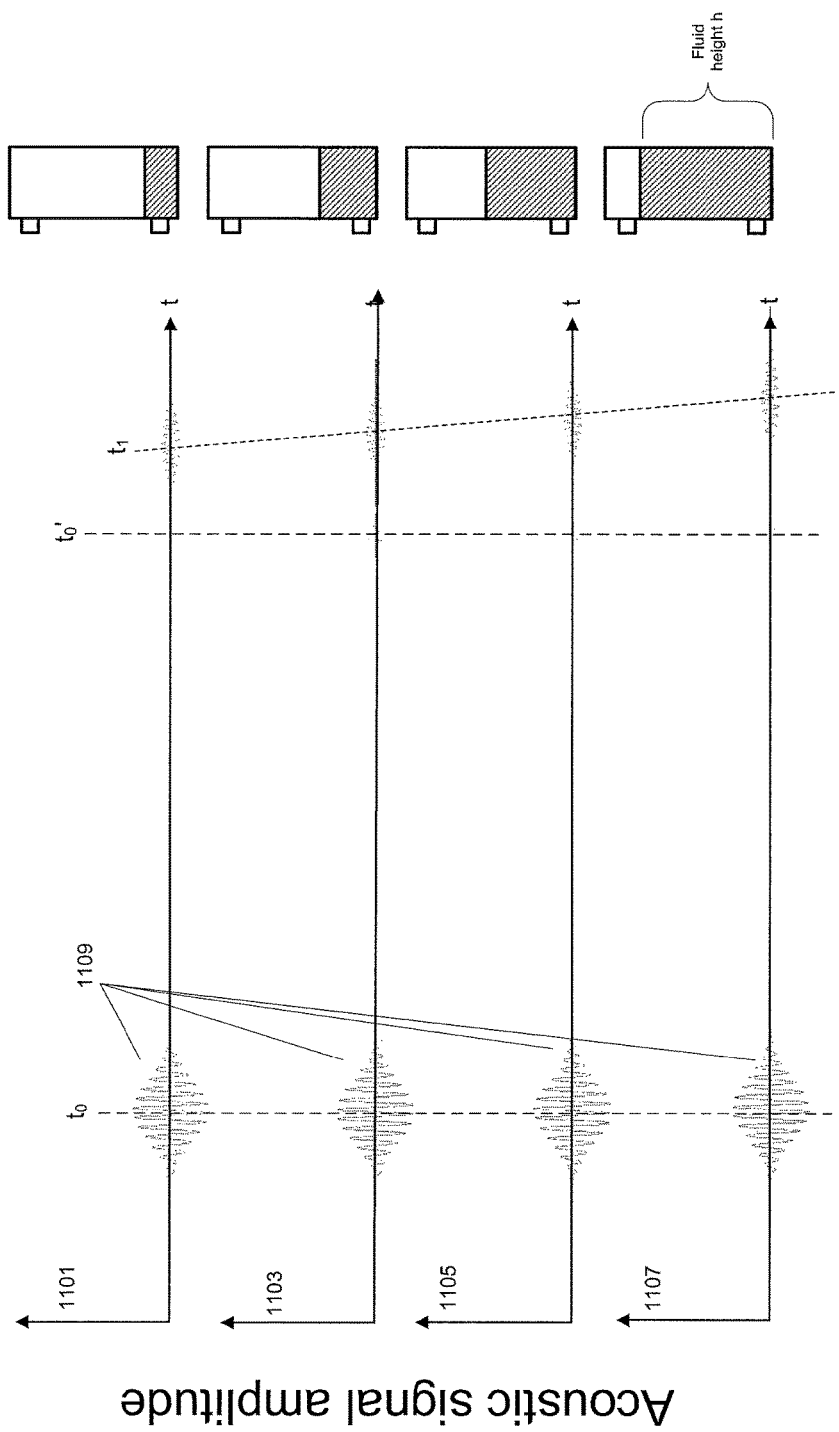
FIG. 11 shows a conceptual example of the effect of vessel fill level (fluid level), on the propagation velocity of acoustic impulses in accordance with one or more embodiments of the invention.

FIG. 11 shows a conceptual example of the effect of vessel fill level (fluid level), on the propagation velocity of acoustic wave packets in accordance with one or more embodiments of the invention. More specifically, graphs 1101-1107 show plots of an acoustic wave impulse as measured by the acoustic impulse generator 1003 in a time window centered about $t_0$ and plots of acoustic wave amplitude as measured by the acoustic impulse receiver 1005 at a time window roughly centered about the times $t_0'$ and/or $t_1$. FIG. 11 further shows the effect of different fluid levels in the tank on the propagation speed of the acoustic impulse. As shown in FIG. 11, the height of fluid in the vessel affects the speed of the flexural wave packet but does not substantially affect the speed of the preflexural wave packet. For example, graph 1101 shows an example of a tank that is approximately 20 percent full, graph 1103 shows an example of a tank that is approximately 40 percent full, graph 1105 shows an example of a tank that is approximately 60 percent full and graph 1107 shows an example of a tank that is approximately 80 percent full.

As can be seen in FIG. 11, the velocity of the preflexural wave is not significantly affected by the amount of fluid in the vessel. However, the velocity of the flexural wave is measurably affected. Accordingly, in accordance with one or more embodiments of the invention, the fill level of the tank may be determined by measuring either the time of flight between the acoustic impulse generator and acoustic impulse receiver, i.e., $t_1-t_0$ or may be determined using the difference in arrival times between the preflexural wave and the flexural wave at the receiver, i.e., $t_1-t_0'$. In addition, in accordance with one or more embodiments, the fill level may be determined through a measurement in the change in width of the flexural wave impulse, i.e., a measurement of the dispersion of the wave packet vs. time as described in more detail below.

Figure 10:
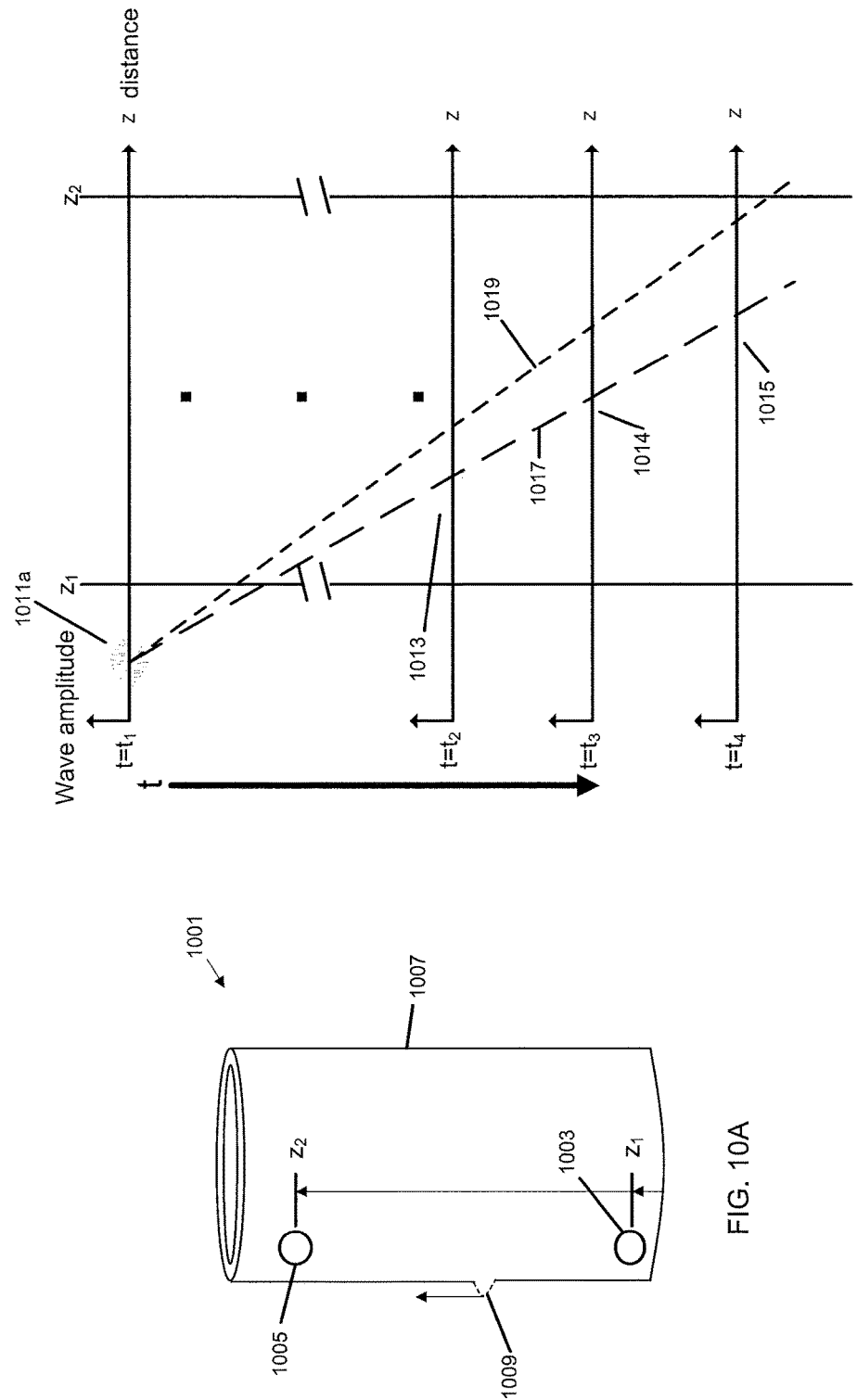
FIGS. 10A-10B show an example of a system for wirelessly monitoring a fill level in a vessel in accordance with one or more embodiments of the invention.
Figure 12:
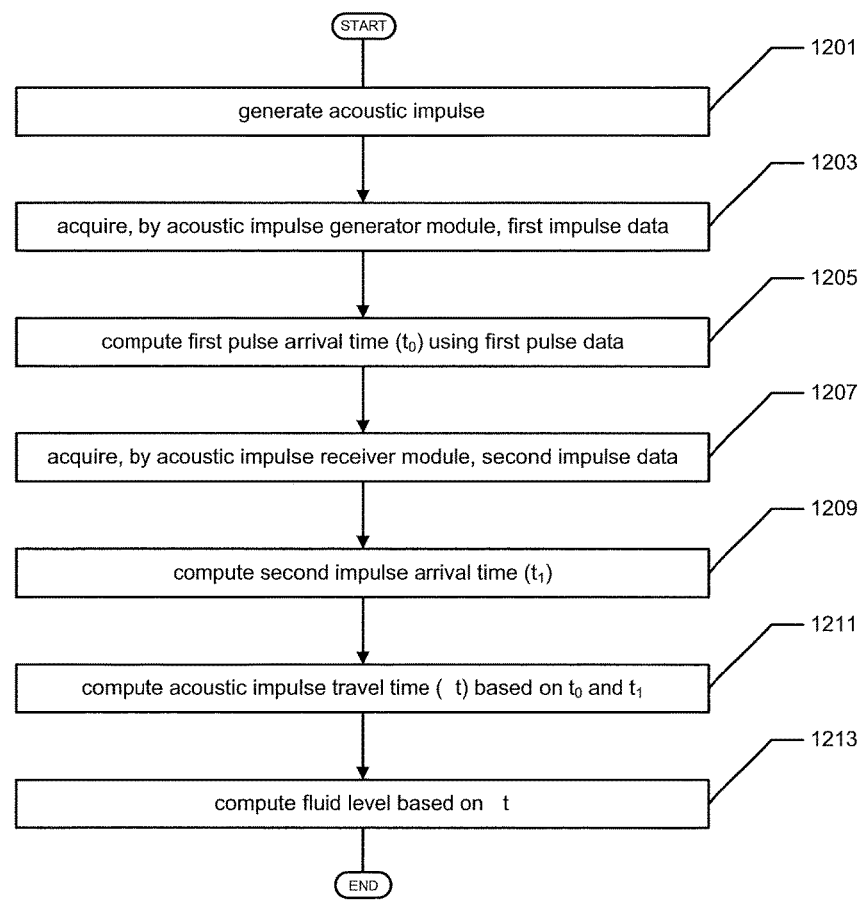
FIG. 12 shows a flow chart describing a method for measuring the fluid level in a vessel in accordance with one or more embodiments of the invention.

FIG. 12 shows a flow chart describing a method for measuring the fluid level in a vessel in accordance with one or more embodiments of the invention. The method may be employed in conjunction with a system as described above, for example in FIGS. 10-11 and in the system shown in FIGS. 23A and 23B. In step 1301, an acoustic impulse is generated in the wall of a vessel. For example, the acoustic impulse may be an initial acoustic impulse 1109 shown in FIG. 11, generated by an acoustic impulse generator 1003, e.g., as shown in FIGS. 10 and 23A and B. In accordance with one or more embodiments, the method may be employed in conjunction with a system as described above, for example in FIGS. 10-11 and in the system shown in FIG. 21 or in conjunction with any known system for generating acoustic impulses. In step 1203, first impulse data is acquired by sampling, at a predetermined rate, the output signal of an acoustic sensor, e.g., a microphone, located in the acoustic impulse generator. The first impulse data is then stored in the internal memory of the acoustic impulse generator. Alternatively, after acquisition, the first impulse data may be transmitted to the acoustic impulse receiver for processing and/or storage in memory at the acoustic impulse receiver and/or a remote server for processing and/or storage in memory.

Figure 17B:
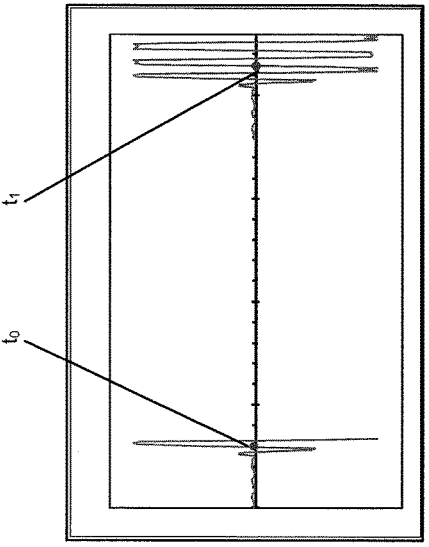
FIG. 17B shows an example of acoustic impulse data acquired by an acoustic impulse generator and acoustic impulse data.

In step 1205, the first impulse arrival time $t_0$ is computed. As described in more detail below, the first impulse arrival time $t_0$ may be computed from the first impulse data in a number of ways. In addition, the first impulse arrival time $t_0$ may be computed using the processor of the acoustic impulse generator, by the processor of the acoustic impulse receiver, or by a remote server after the first impulse data has been transferred over the wireless network to the remote server. In accordance with one or more embodiments, $t_0$ may be computed by determining the time of acquisition of the maximum value of the first impulse data. Alternatively, $t_0$ may be determined by the time of a zero-crossing in the first impulse data described in more detail below in reference to FIGS. 16-18. More generally, $t_0$ may be determined by choosing any point in the first impulse data that occurs between a zero crossing and a peak without departing from the scope of the present disclosure. For example, such an arbitrary point may be determined by selecting a point in the first impulse having an amplitude value falls within a predefined range of values.

As illustrated in FIGS. 10 and 11, after generation, the initial acoustic impulse 1109 propagates through the vessel wall, along the length or height of the vessel until it reaches the impulse receiver at some time $t_1$ after $t_0$. In step 1207, second impulse data is acquired by sampling, at a predetermined rate, the output signal of an acoustic sensor, e.g., a microphone, located in the acoustic impulse receiver. The second impulse data is then stored in the internal memory of the acoustic impulse receiver. Alternatively, after acquisition, the second impulse data may be transmitted to the acoustic impulse generator for processing and/or storage in memory at the acoustic impulse generator and/or a remote server for processing and/or storage in memory.

In step 1209, the second impulse arrival time $t_1$ is computed. As described in more detail below, the second impulse arrival time $t_1$ may be computed from the first impulse data in a number of ways. In addition, the second impulse arrival time $t_1$ may be computed using by the processor of the acoustic impulse receiver 1003, by the processor of the acoustic impulse generator, or by a remote server after the second impulse data has been transferred over the wireless network to the remote server. In accordance with one or more embodiments, $t_1$ may be computed by determining the time of acquisition of the maximum value of acoustic impulse waveform data. Alternatively, $t_1$ may be determined using a zero-crossing method and/or dispersion method described in more detail below in reference to FIGS. 16-18.

In step 1211, the total travel time of the acoustic impulse between the impulse generator 1003 and the impulse receiver 1005 is calculated based upon $t_1$ and $t_0$. For example, in accordance with one or more embodiments, the total travel time $\Delta t = t_1 - t_0$. Then in step 1213, the fluid level is computed based upon $\Delta t$ and a previously determined time-to-level calibration factor as is known in the art. While the precise form for converting $\Delta t$ to fluid level will vary depending on many factors, including tank shape, material of fabrication, temperature (both tank and fluid), field tests done by the inventor on tanks commonly employed in the oilfield and agricultural fields produce acoustic waves whose velocity changes within a range of 10-40 microseconds per inch of fluid.

Figure 13B:
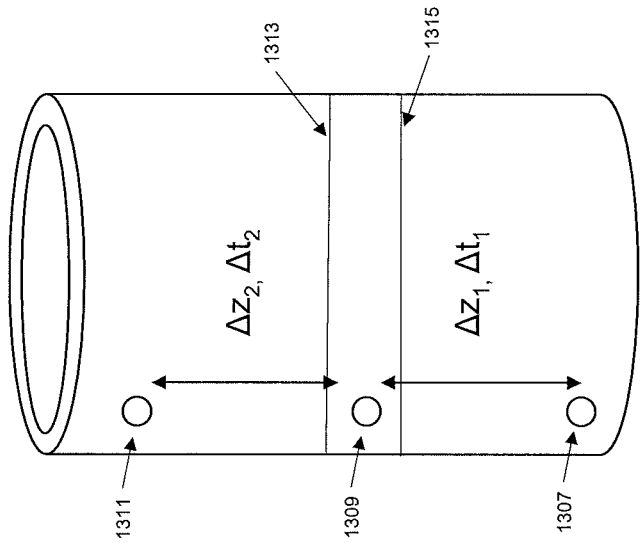
FIGS. 13A-13B show acoustic fluid level sensor systems in accordance with one or more embodiments of the invention.
Figure 13A:
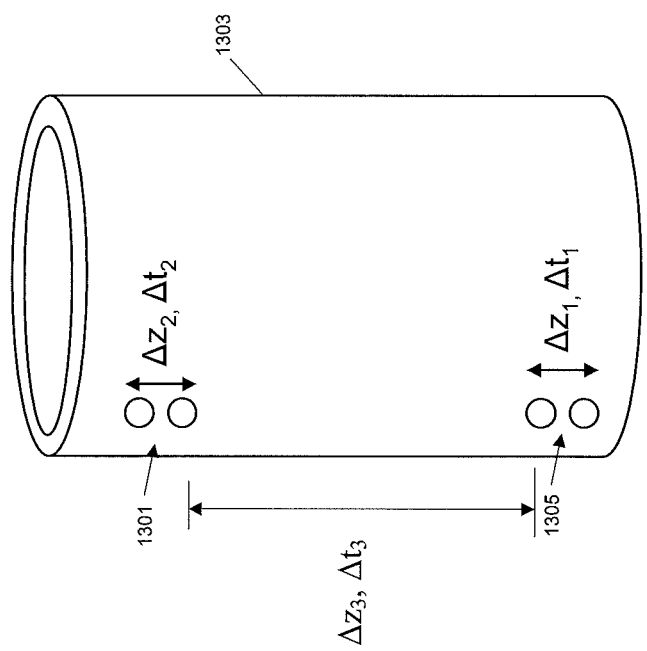

In accordance with one or more embodiments, system for measuring fluid level in a container may employ additional receiver(s) in the system. Two such embodiments are shown in FIGS. 13A-13B. In the embodiments shown in FIG. 13A, an upper pair of receivers 1301 is placed near the top of the tank 1303 in normally fluid-free condition, and a second lower pair 1305 is located near the bottom where in a normally fluid-filled condition. In this configuration, the end-point travel times for 100% full and 100% empty conditions can be continually established and monitored for changes, for instance temperature changes that can systematically affect the travel times. Accordingly, using these endpoint values the % fluid fill can be calculated using a linear interpolation based on total travel time measured between pairs and the 100% full and 100% empty time measurements. For example, if the empty travel time measured by pair 1301 is $\Delta t_e$ and the full travel time measured by pair 1305 is $\Delta t_1$, the empty velocity (0% full) is given by $\Delta z_2/\Delta t_2 = v_2$ and the full velocity (100% full) is given by $\Delta z_1/\Delta t_1 = v_1$ Accordingly, to measure the relative level in the tank, the travel time between any two receivers of different pairs may be used, e.g., $\Delta t_a$, as shown in FIG. 13A. Thus, the measured velocity for the unknown fill level is $\Delta z_3/\Delta t_3 = v_3$ and the relative fill level may be computed from the following linear interpolation:

$$\text{Fill \%} = 100\left(\frac{v_3 - v_2}{v_1 - v_2}\right)$$

In another embodiment shown in FIG. 13B, the 'full' and 'empty' conditions can be measured alternately as the fluid level rises or drops below the midline receiver 1307 level. As before with the embodiment shown in FIG. 13A, once the 'full' and 'empty' velocities are determined, the relative fill level may be computed with the linear interpolation described above. The two embodiments shown in FIGS. 13A-13B can reduce the uncertainty of the fluid calculation by immediately establishing reference 'full' and 'empty' travel times, and they also inform the calculations with continual slight changes due to temperature (always it is assumed that the fluid properties don't change, which is a good assumption under normal field conditions). Advantageously, the system shown in FIG. 13A allows for a simple system because the receiver pairs are always in a 100% wet or dry condition. Alternately, the system shown in FIG. 13B, requires one less receiver circuit and much less demand on timing accuracy because the receiver pairs are separated by a greater distance (e.g., feet instead of inches). However, in this example additional processing is needed to determine on whether the data are completely 'full' or 'empty.' For example, at the fill level 1313, the travel time from generator 1307 to receiver 1309 may be used to determine the 'full' condition. Likewise, at the fill level 1315, the travel time between receivers 1311 and 1309 may be used to determine the completely 'empty' condition. Accordingly, in accordance with one or more embodiments, the fluid level may be monitored continuously and when the fluid is clearly above the midline, the 'full' condition travel time may be calculated using the lower pair of modules 1309, 1307, and when the fluid is clearly below the midline, the 'empty' travel time may be calculated using the upper pair 1309, 1311 of modules. The determined travel times and known distances separating the modules can be used for subsequent calculations as described above in reference to FIG. 13A. Of course, in all of the embodiments disclosed herein, which module is the receiver and which is the generator may be different from that shown in the Figure without departing from the scope of the present disclosure.

Figure 14:
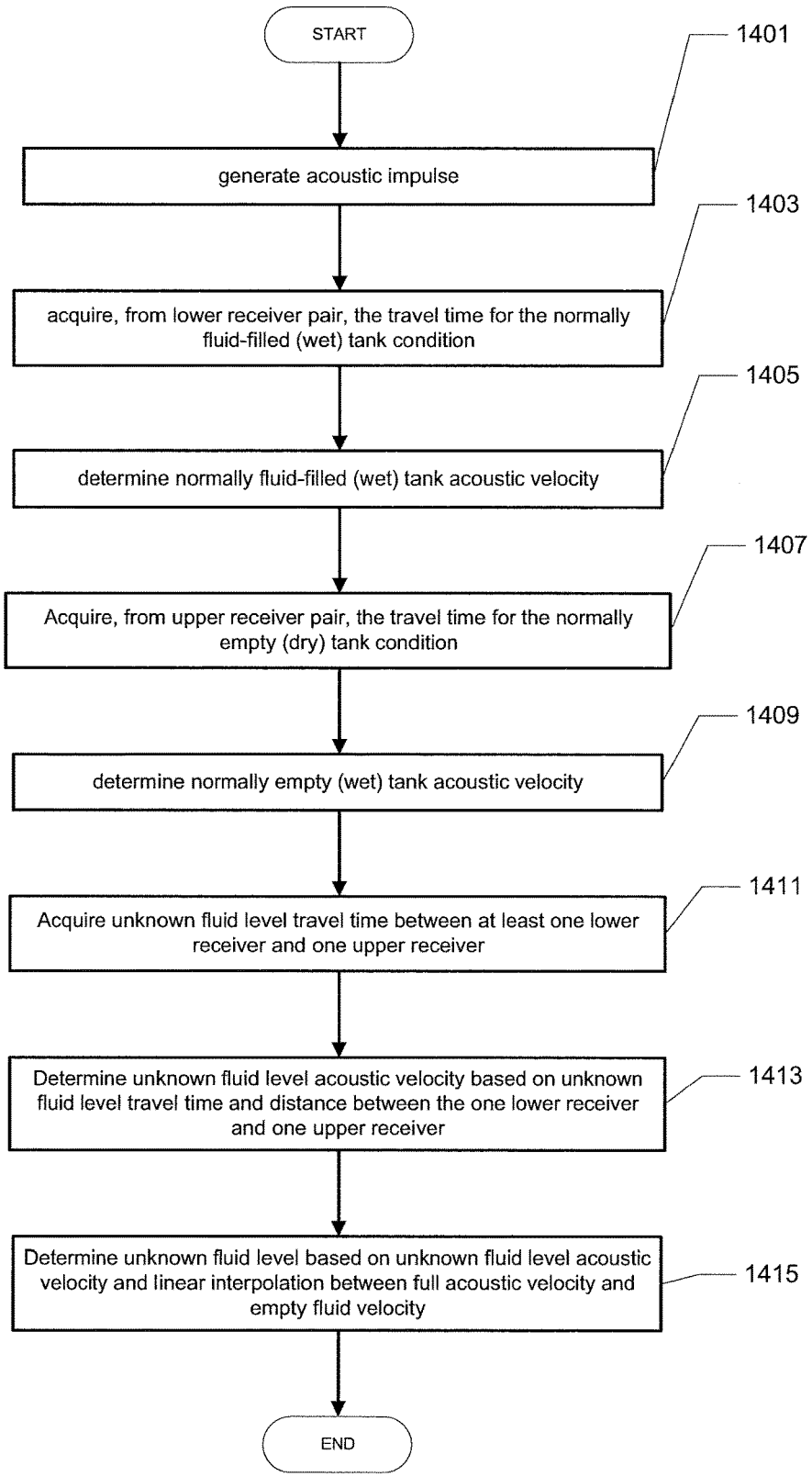
FIG. 14 shows a flow chart describing a method for measuring the relative fluid level in a vessel in accordance with one or more embodiments of the invention.

FIG. 14 shows a flow chart of the method for determining a relative fill level as described above in reference to FIGS. 13A-13B. In step 1401, an acoustic impulse is generated. In step 1403, a lower receiver pair acquires the travel time of this acoustic impulse between the two receivers of the receiver pair. This travel time is the normally fluid-filled tank condition travel time. In step 1405, the fluid filled tank acoustic velocity is determined from the normally fluid-filled tank travel condition travel time and the known separation between the receivers of the lower receiver pair. In step 1407, an upper receiver pair acquires the travel time of the acoustic impulse between the two receivers of the upper receiver pair. This travel time is the normally empty tank condition travel time. In step 1409, the empty tank acoustic velocity is determined from the normally empty tank condition travel time and the known separation between the receivers of the upper receiver pair. In step 1411, an unknown fluid level travel time is acquired between at least one lower receiver and one upper receiver. In step 1413, the unknown fluid level acoustic velocity is determined based upon the unknown fluid level travel time and the distance between the lower receiver and the upper receiver used to measure the unknown fluid level travel time. In step 1415, the unknown fluid level is determined based on the unknown fluid level acoustic velocity and a linear interpolation between the full acoustic velocity and the empty acoustic velocity, e.g., using the equation described above in reference to FIGS. 13A-13B.

Figure 15B:
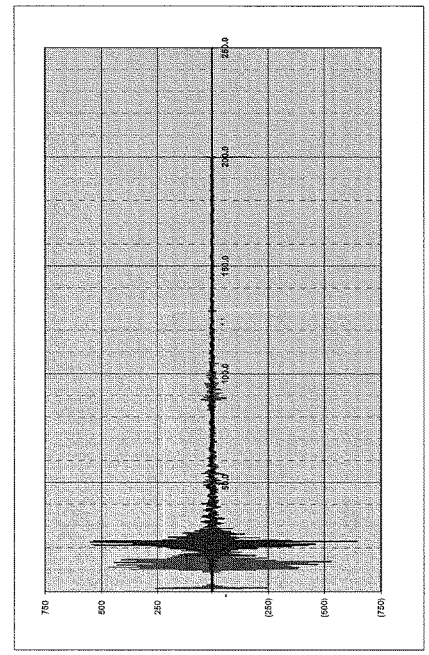
FIGS. 15A-15D show examples of typical acoustic data recorded by a wireless sensor module deployed as an acoustic sensor of an impulse generator or by an acoustic sensor of an impulse receiver in accordance with one or more embodiments of the invention.
Figure 15D:
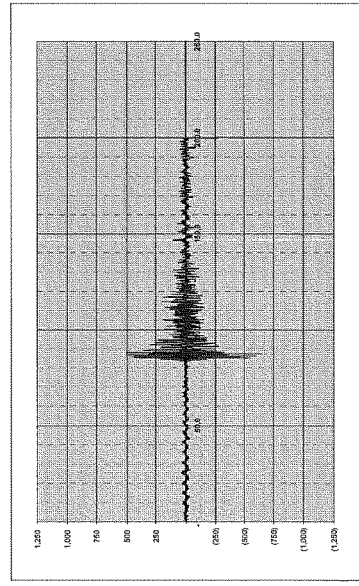
Figure 15A:
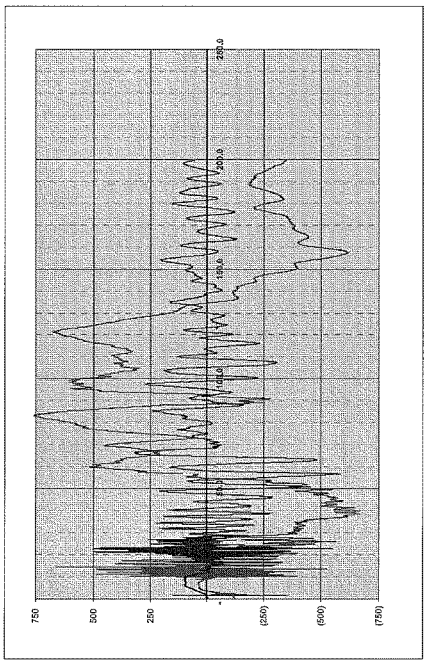
Figure 15C:
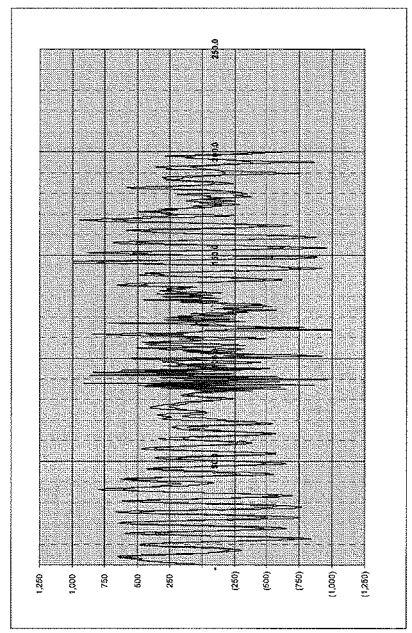

In practice, the acoustic signals measured in the field always include substantial noise and, due to limited on-board processing speed and memory, the signals themselves may eventually be down sampled or compressed, as described in more detail below. These two factors taken in combination often severely impair the ability of the microcontroller to make accurate measurements of $t_1$ and $t_0$ without some amount of preprocessing of the raw data. Typical field conditions include various noise sources such as wind, vehicle engine noise, or the like. FIGS. 15A-15D show examples of typical acoustic data recorded by an acoustic sensor of an impulse generator or by an acoustic sensor of an impulse receiver. FIG. 15A illustrates the effect of wind noise that is picked up either directly by the acoustic sensor or conducted through the vessel wall as the wind blows against the surface area of the vessel. As shown in FIG. 15A wind effects produce relatively high amplitude and low frequency noise which swamps the acoustic impulse signal. In accordance with one or more embodiments, a N-sample digital window filter may be applied e.g., a Bessel filter, Butterworth filter, Elliptical filter, Linkwitz-Riley filter, Chebyshev filter, Ladder filter, Biquad filter, or the like, to reduce the noise after the acoustic impulse data has been acquired. For example, FIG. 15B shows the result after filtering using a 15-sample boxcar low-pass digital filter. Similarly, FIG. 15C shows the effect of engine noise on the measured acoustic impulse signal and FIG. 15D shows the results after applying a 15-sample digital filter. In accordance with one or more embodiments, the digital filter is applied to the data using the hardware and software resources available within the wireless sensor modules themselves, e.g., within a microcontroller, as shown in FIGS. 23A-23B. In other embodiments, analog filters may be employed as additional hardware within the data acquisition and amplification circuitry.

FIGS. 16A-16B show an example of acoustic impulse data 1601 acquired by an acoustic impulse generator and acoustic impulse data 1603 acquired by an acoustic impulse receiver in accordance with one or more embodiments of the invention. More specifically, an acoustic sensor of an impulse generator may acquire a portion 1601*a* of acoustic impulse data 1601, wherein the portion 1601*a* is located within generator acquisition time window 1605. The location and width of generator acquisition time window 1605 may be programmed in advance into the control system of acoustic impulse generator. In accordance with one or more embodiments, generator acquisition time window 1605 is programmed to record an initial portion 1601*a* of the acoustic impulse data 1601, so as to record the initiation of the acoustic impulse generated by acoustic impulse generator. One of ordinary skill will appreciate that generator acquisition time window 1605 may encompass a different portion of the acoustic impulse data 1601 or, in addition, may include the entire the acoustic impulse data 1601. FIG. 16B shows an example of the portion 1601*a* of acoustic impulse data 1601 as acquired by an acoustic impulse generator.

Figure 23:
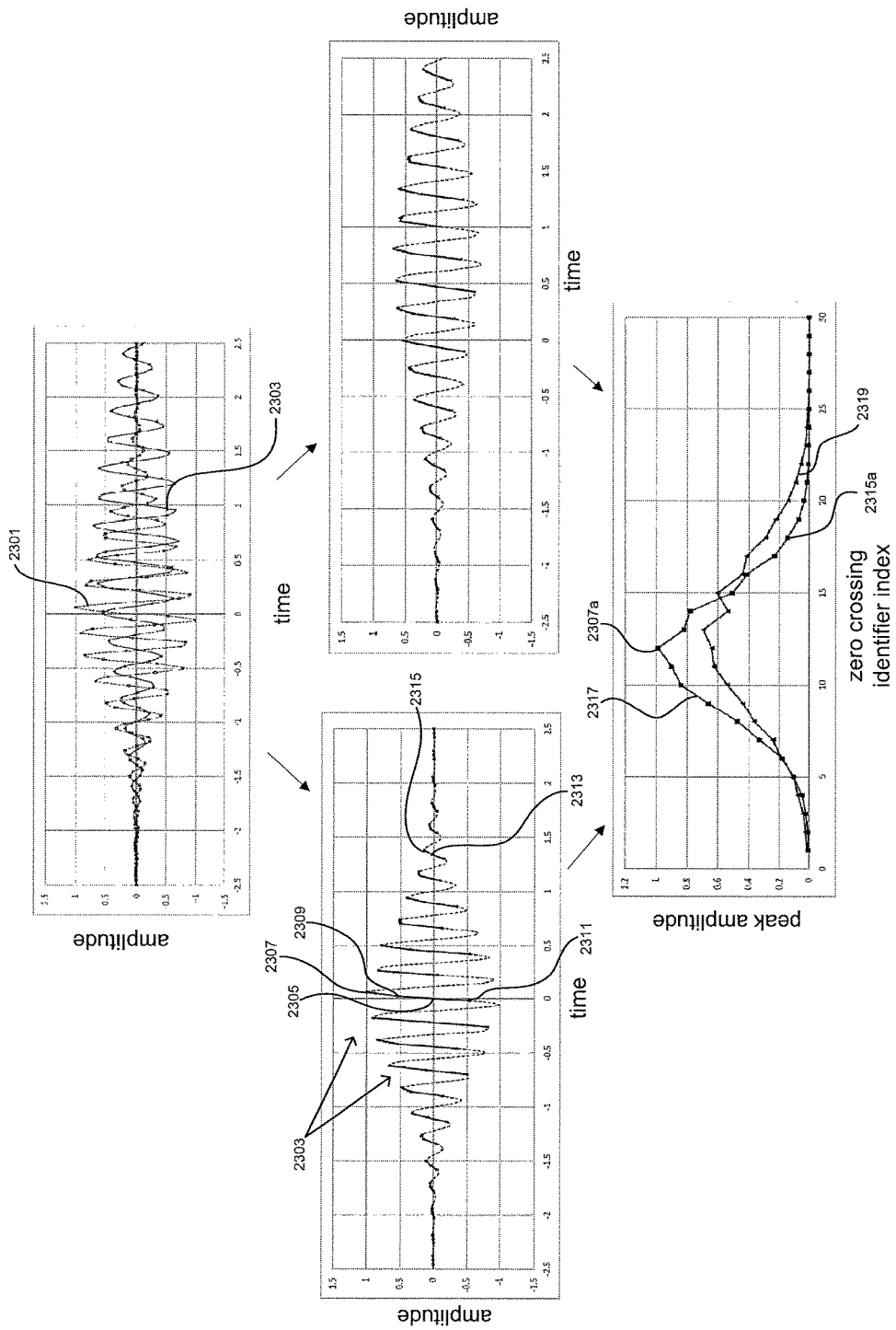
FIG. 23 shows examples of acoustic data in accordance with one or more embodiments of the invention.

Furthermore, in a manner similar to that described above for the acquisition of acoustic impulse data 1601, the acoustic impulse 1603 may be acquired by an acoustic impulse receiver, similar to that shown in FIGS. 11 and 23. More specifically, an acoustic sensor of an impulse receiver may acquire a portion 1603*a* of acoustic impulse data 1603, wherein the portion 1603*a* is located within receiver acquisition time window 1607. As shown in FIG. 16A-16B, in accordance with one or more embodiments, receiver acquisition time window 1607 may be configured in advance in order to acquire the initial or earliest arriving portion, of the acoustic impulse 1603 that has traveled along a length/height of the tank. Advantageously, acquiring the early portion of acoustic impulse 1603 as shown in FIG. 16A-16B eliminates distortions in the acoustic data which may be due to acoustic reflections (echoes) that have propagated along the length of the tank and returned to the acoustic impulse receiver. Advantageously, the elimination of these reflected waves from the acquisition results in a system of higher accuracy and repeatability. Shown in FIG. 16B is an acquired portion 1603*a* of acoustic impulse data 1603 that shows little degradation from the interference effects of reflected waves. In particular, a relatively low amplitude preflexural wave 1603*b* is seen to arrive before the flexural wave 1603*c*.

The precise location in time of time windows 1605 and 1607 depends on many factors including the Young's modulus G of the vessel wall, the density and thickness of the vessel wall material, the density and compressional modulus of the fluid, and the temperature of the tank and/or fluid. Thus, prior knowledge of the vessel being monitored is preferable for setting up the time gates within the impulse generator and impulse receiver to ensure that the desired data is acquired. In absence of any knowledge of the physical characteristics of the vessel, the time windows may be set up by service personnel at the time of installation in the field. However, such a process is time consuming and fraught with difficulty associate with the "trial and error" approach required to determine the precise location of the time windows. In accordance with one or more embodiments, the impulse generator and impulse receiver may be configured to compute the location of the time windows based upon a physical model and various parameters associated with the properties of the tank being measured. These physical parameters may be previously stored in memory of the modules themselves or may be stored at a remote location accessible on the network and retrieved by the modules when needed. Alternatively, a service person may input the parameters directly into a mobile device and the mobile device may upload these parameters to a remote server or the parameters may be transmitted to the devices in accordance with methods known in the art.

Of particular importance for the computation of the time windows 1605 and 1607 is the velocity of propagation $c_p$ of the flexural waves along the wall of the tank Lamb's equation, with modifications, may be used to approximate the velocity of flexural wave in a cylindrical vessel when the thickness of the vessel wall is small compared to the diameter of the vessel, a condition that is met by most vessels in the field. This velocity $c_p$ is given by $$c_p^2 = c_r^2 \left[ \frac{4}{3} f^3 \xi^3 \left(1 - \frac{c_r^2}{c_d^2}\right) \frac{p_s}{p_w} \right] \frac{1}{1 + \xi f \frac{p_s}{p_w}}$$

where $c_r$ is the rotational (shear) velocity of sound in the vessel wall, $c_d$ is the dilational (longitudinal) velocity of sound in the vessel, f is ½ the thickness of the vessel wall, $\xi$ is the wavenumber, $\rho_s$ is the density of the tank wall, and $\rho_w$ is the density of fluid in the vessel. Through the use of the above equation, the velocity of the flexural wave may be estimated and, given the known distance between the impulse generator and impulse receiver, the propagation time of the flexural wave between the impulse generator and impulse receiver may be computed. Accordingly, the positions of acquisition windows 1605 and 1607 may be computed without the requirement of a time-consuming trial and error calibration procedure employed by field personnel. In some situations small corrections to the computed acquisition windows 1605 and 1607 may be made to compensate for effects not taken into account in the model. In accordance with one or more embodiments, the use of the physical model embodied by the above modified Lamb's equation enables the prediction and calibration of the technique for different fluid and vessel properties and environmental variations. In addition, software onboard the field modules can initiate an auto-calibration procedure upon power-up during field installation. For instance, the receiver can be programmed to search for the time of arrival of the maximum amplitude wave crossing in a series of programmed test measurements. This information can be used to establish the approximate boundaries of the expected acquisition time interval.

Figure 17A:
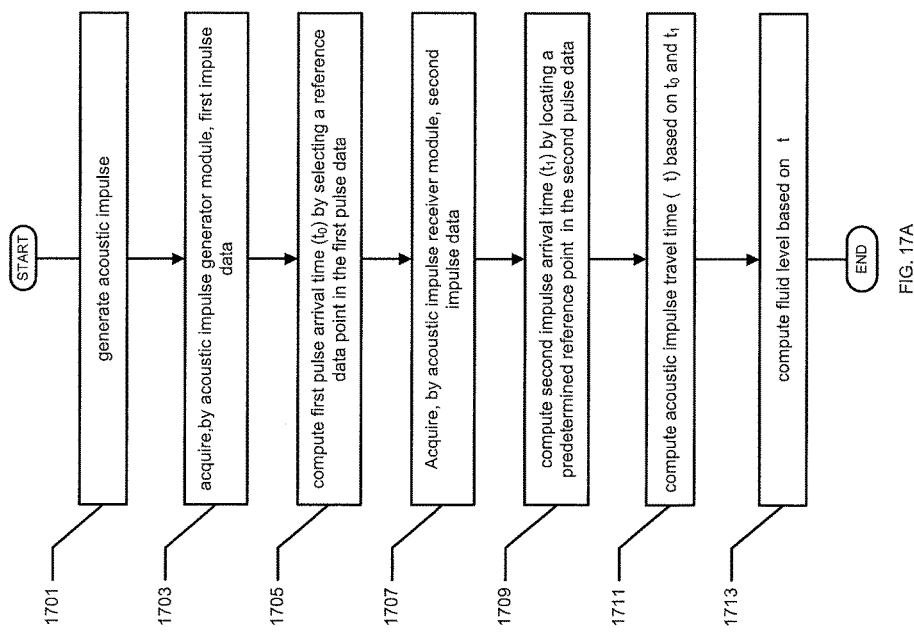
FIG. 17A shows a flow chart describing a method for measuring the fluid level in a vessel in accordance with one or more embodiments of the invention.

FIG. 17A shows a flow chart describing a method for measuring the fluid level in a vessel in accordance with one or more embodiments of the invention. More specifically, FIG. 17 describes a method for measuring fluid level that employs zero-crossing detection in the acoustic data to determine $t_0$ and $t_1$. The method may be employed in conjunction with a system as described above, for example in FIGS. 11-11 and, e.g., in the system shown in FIGS. 23A-23B. In step 1701, an acoustic impulse is generated in the wall of a vessel. For example, the acoustic impulse may be an initial acoustic impulse 1109 shown in FIG. 11, generated by an acoustic impulse generator 1103 as shown in FIG. 11. In accordance with one or more embodiments, the method may be employed in conjunction with a system as described above, for example in FIGS. 11-11 and in the system shown in FIG. 21, or in conjunction with any known system for generating acoustic impulses. In step 1703, first impulse data is acquired by sampling, at a predetermined rate, the output signal of an acoustic sensor, e.g., a microphone, located in the acoustic impulse generator. The first impulse data is then stored in the internal memory of the acoustic impulse generator. Alternatively, after acquisition, the first impulse data may be transmitted to the acoustic impulse receiver for processing and/or storage in memory at the acoustic impulse receiver and/or a remote server for processing and/or storage in memory.

In step 1705, the first impulse arrival time $t_0$ is computed by selecting a reference data point in the first pulse signal data. In one example, the first impulse arrival time $t_0$ is computed as the first zero crossing in a rising slope (i.e., slope>0) of the first impulse data. Advantageously, selecting $t_0$ to be the first rising slope zero crossing enables a precise determination of $t_0$ even when the amount of acquired data is low and/or the when the absolute peak of the acoustic impulse is not measurable, either due to the acquired signal being noisy, amplifier saturation, or due to the fact that the acquisition window was not long enough to capture the entire acoustic impulse waveform. Advantageously, because the first zero crossing (or, equivalently any early occurring zero crossing) is chosen, only a small portion of the total waveform need by collected, greatly lowering the data storage and processing requirements. For example, in FIG. 17B, it is seen that $t_0$ can be computed accurately even when only a small fraction of the total acoustic impulse is acquired, e.g., only 1.5 complete cycles. The need to require a only a fraction of the total waveform results in the benefit of reduced memory requirements, reduced requirement on the processor clock speed for pre- and post-data processing and consequently reduced total cost and reduced power consumption of the system.

In accordance with one or more embodiments, because the location of the zero crossing is used rather than the overall peak of the waveform, the computation is less sensitive to systematic effects that may result from the application of a low pass filter to a noisy signal. Applying a strong low pass filter to remove noise sources such as wind noise, vehicle noise, compressor noise, or the like, becomes readily available. In addition, field tests by the inventor have shown that the position of the zero crossing is generally much less sensitive to noise than the overall peak value of the dataset. Accordingly, the use of the zero crossing technique as disclosed herein allows for a highly repeatable measurements of $t_0$.

In embodiments where the data is sampled across the zero crossing without logging a point sufficiently close to the zero crossing, a linear interpolation technique may be employed to find the zero crossing. For example, the data point just above and below zero may be used to linearly interpolate the position of the zero crossing. In accordance with one or more embodiments, the data processing necessary to locate the zero crossing may be done using the processor of the acoustic impulse generator, by using the processor of the acoustic impulse receiver, or by a remote server after the first impulse data has been acquired by the acoustic impulse generator and transferred over the wireless network to the remote server.

Furthermore, one of ordinary skill in the art will recognize that while the first zero crossing is illustrated in the example above for obtaining $t_0$, any zero crossing may be used without departing from the scope of the present disclosure. Furthermore, as discussed above, the time when the impulse data reaches a maximum may be used. Alternatively, combinations of all the above may also be used. For example, the times of several zero crossings and/or the peak time may be averaged together and used as the $t_0$ reference. Furthermore, while the examples of zero crossings and peak amplitudes are used in the example laid out above, any reference point may be used without departing form the scope of the present disclosure. For example, $t_0$ may be determined by choosing any point in the first impulse data that occurs between a zero crossing and a peak without departing from the scope of the present disclosure. For example, such an arbitrary point may be determined by selecting a point in the first impulse that whose amplitude value falls within a predefined range of values. Once of ordinary skill, having the benefit of this disclosure, will appreciate that the interpolation procedure described above in the context of zero crossing interpolation may also be applied for any point without departing from the scope of the present disclosure.

As illustrated in FIGS. 11 and 11, after generation, the initial acoustic impulse propagates along the vessel wall, along the length or height of the vessel until it reaches the impulse receiver at some time $t_1$ after $t_0$. In step 1707, second impulse data is acquired by sampling, at a predetermined rate, the output signal of an acoustic sensor, e.g., a microphone, located in the acoustic impulse receiver. The second impulse data is then stored in the internal memory of the acoustic impulse receiver. Alternatively, after acquisition, the second impulse data may be transmitted to the acoustic impulse generator for processing and/or storage in memory at the acoustic impulse generator and/or a remote server for processing and/or storage in memory.

In step 1709, the second impulse arrival time $t_1$ is computed. In accordance with one or more embodiments, $t_1$ may be computed by selecting a zero crossing in the flexural wave data in a manner that is identical to that described above in reference to step 1705. In step 1711, the total travel time of the acoustic impulse between the impulse generator and the impulse receiver is calculated based upon $t_1$ and $t_0$. For example, in accordance with one or more embodiments, the total travel time $\Delta t = t_1 - t_0$. Then in step 1713, the fluid level is computed based upon $\Delta t$ and a previously determined time-to-level calibration factor, as is known in the art. Alternatively, using the known distance between the impulse generator and the impulse receiver in conjunction with the measured and $\Delta t$, the speed of the flexural wave $c_p$ may be computed.

Furthermore, while the examples of zero crossings and peak amplitudes are used in the example laid out above for obtaining $t_1$, any reference point may be used without departing form the scope of the present disclosure. For example, $t_0$ may be determined by choosing any point in the first impulse data that occurs between a zero crossing and a peak without departing from the scope of the present disclosure. For example, such an arbitrary point may be determined by selecting a point in the first impulse that whose amplitude value falls within a predefined range of values. Once of ordinary skill having the benefit of this disclosure will appreciate that the interpolation procedure described above in the context of zero crossing interpolation may also be applied for any point without departing from the scope of the present disclosure.

Figure 18A:
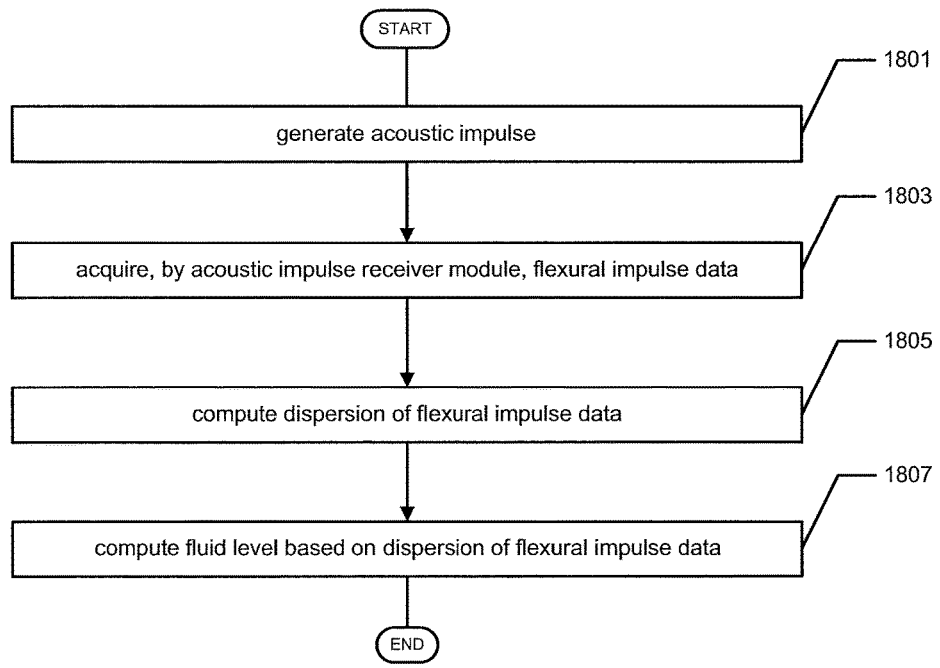
FIG. 18A shows a flow chart describing a method for measuring the fluid level in a vessel in accordance with one or more embodiments of the invention.

FIG. 18A shows a flow chart describing a method for measuring the fluid level in a vessel in accordance with one or more embodiments of the invention. More specifically, FIG. 18A describes a method for measuring fluid level in a vessel by correlating the dispersion, or wave packet spreading, of the flexural wave, with the height of fluid in the vessel. In step 1801, an acoustic impulse is generated in the wall of a vessel. For example, the acoustic impulse may be an initial acoustic impulse 1109 shown in FIG. 11, generated by an acoustic impulse generator 1003 as shown in FIG. 10 or, e.g., in FIG. 25A or 25B. The method may be employed in conjunction with a system as described above, for example in FIGS. 10-11 and in the system shown in FIG. 25 or in conjunction with any known system for generating acoustic impulses. As illustrated in FIGS. 10 and 11, after generation, the initial acoustic impulse propagates through the vessel wall, along the length or height of the vessel until it reaches the impulse receiver at some time after $t_0$. As also shown in FIGS. 10 and 11, as the flexural component of the impulse propagates, the impulse broadens in width, or disperses. In step 1803, the acoustic impulse receiver acquires the propagated flexural wave impulse and stores it as flexural impulse data. The flexural impulse data is acquired by sampling, at a predetermined rate, the output signal of an acoustic sensor, e.g., a microphone, located in the acoustic impulse receiver. The flexural impulse data is then stored in the internal memory of the acoustic impulse receiver. Alternatively, after acquisition, the flexural impulse data may be transmitted to the acoustic impulse generator for processing and/or storage in memory at the acoustic impulse generator and/or a remote server for processing and/or storage in memory.

Figure 18B:
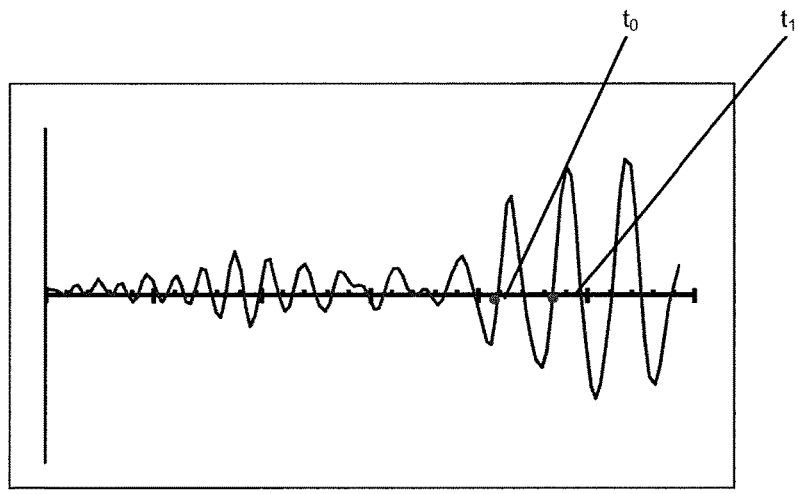
FIG. 18B shows an example of acoustic impulse data acquired by an acoustic impulse generator and acoustic impulse data.

In step 1805, the dispersion of the flexural impulse data is computed. For example, as shown in FIG. 18B, a time difference may be computed between the first and second rising slope zero crossings of the flexural wave impulse data. The first and second zero crossings, occurring at $t_0$ and $t_1$, respectively, may be determined in an identical manner to that described above in reference to FIG. 17. In addition, the location of all measured zero crossings may be computed (not shown).

Figure 19:
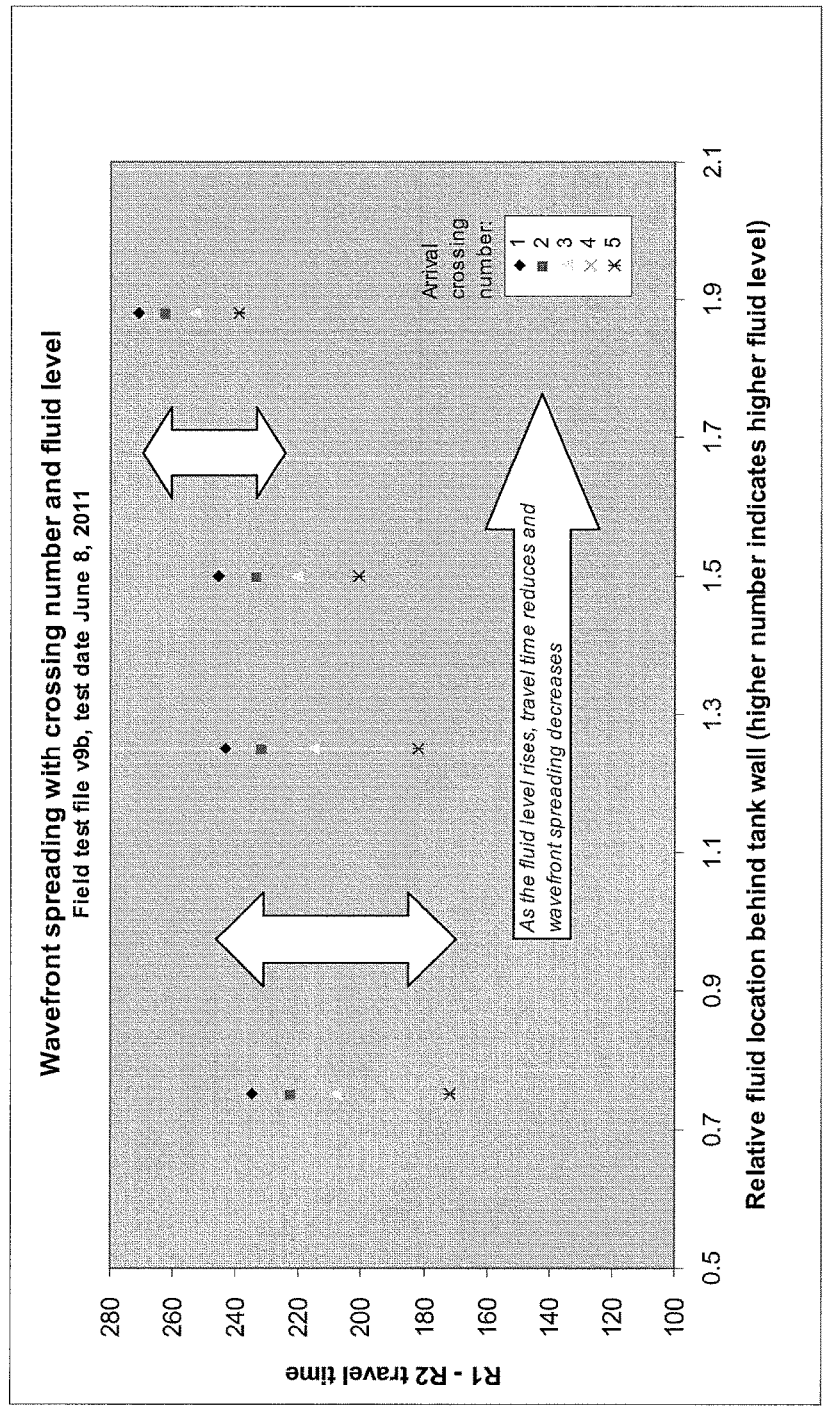
FIG. 19 shows an example of acquired impulse data showing dispersion of the acoustic impulse data.

In step 1807, the fluid level is computed based on the dispersion of the flexural impulse data. As shown in FIG. 19 the width of the overall flexural wave impulse correlates to the height of fluid in the vessel. Accordingly, the height of fluid in the vessel may be computed using only the flexural wave impulse that is acquired by the acoustic impulse receiver. Advantageously, this method is independent of any measurement of the acoustic impulse by the acoustic impulse generator. Accordingly, this method may be used on its own to measure fluid level in the vessel, but may also be used in combination with the other methods disclosed herein to provide a cross-check to help diagnose possible equipment failures, or, for example, multiple independent measurements methods of the same tank may be used to improve the overall accuracy of the level detection method.

Figure 20B:
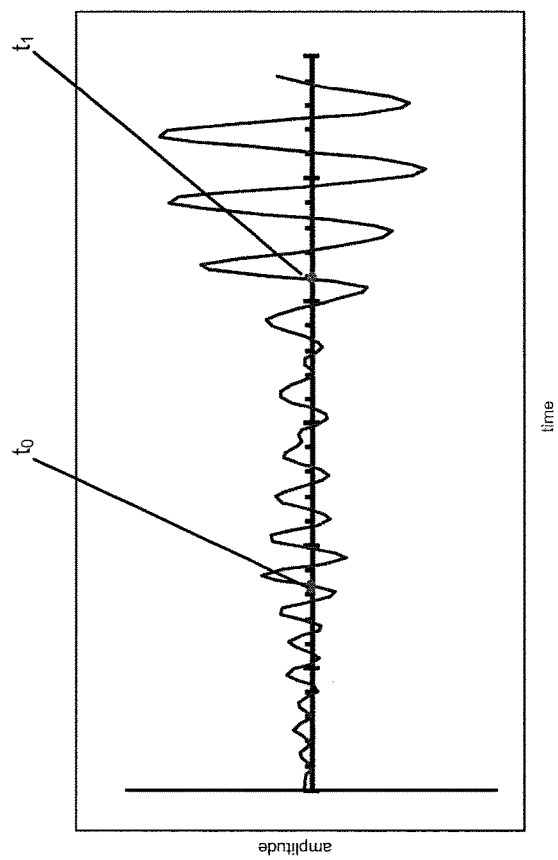
FIG. 20B shows an example of acoustic impulse data acquired by an acoustic impulse generator and acoustic impulse data.
Figure 20A:
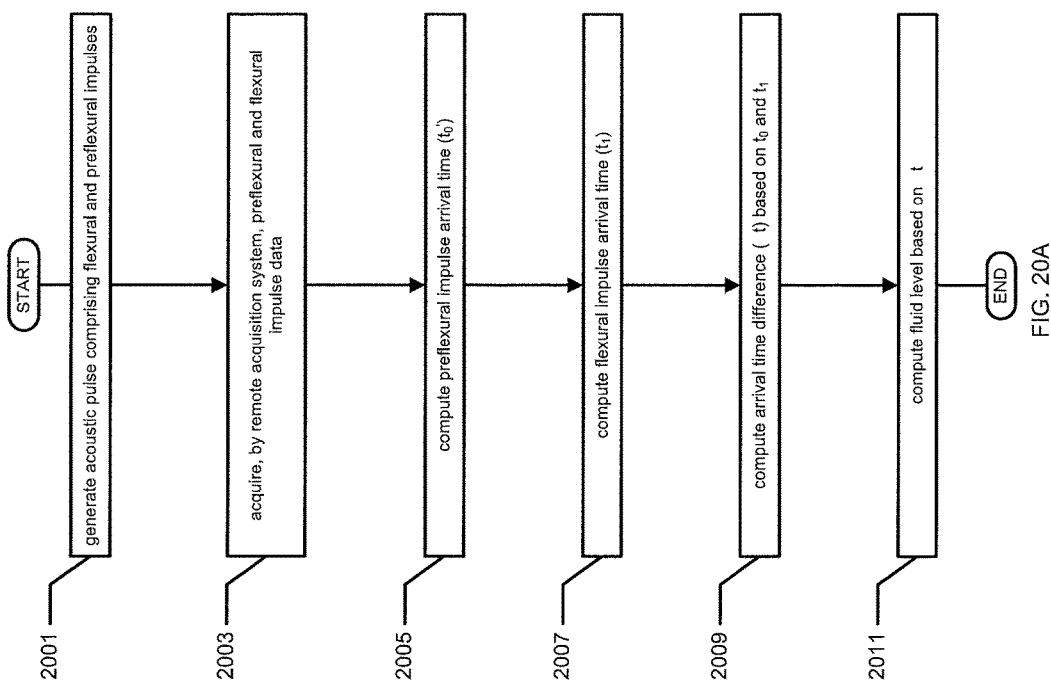
FIG. 20A shows a flow chart describing a method for measuring the fluid level in a vessel in accordance with one or more embodiments of the invention.

FIGS. 20A-20B show examples of a method for measuring the fluid level in a vessel that employs a pre-flexural wave referencing computation. In step 2001, an acoustic impulse is generated in the wall of a vessel. For example, the acoustic impulse may be an initial acoustic impulse 1109 shown in FIG. 11, generated by an acoustic impulse generator 1003 as shown in FIG. 10. In addition, as shown in FIGS. 10 and 11, the acoustic impulse includes a flexural wave and a preflexural wave. As with the previous methods, the method may be employed in conjunction with a system as described above, for example in FIGS. 10-11 and in the system shown in FIG. 25 or in conjunction with any known system for generating acoustic impulses. As illustrated in FIGS. 10 and 11, after generation, the initial acoustic impulse propagates through the vessel wall, along the length or height of the vessel until it reaches the impulse receiver at some time after $t_0$. As also shown in FIGS. 10 and 11, as the flexural component of the impulse propagates, the impulse broadens in width, or disperses and also, separates from the preflexural component of the impulse. In step 2003, flexural and preflexural impulse data is acquired by sampling, at a predetermined rate, the output signal of an acoustic sensor, e.g., a microphone, located in the acoustic impulse receiver. The flexural and preflexural impulse data is then stored in the internal memory of the acoustic impulse receiver. Alternatively, after acquisition, the flexural and preflexural impulse data may be transmitted to the acoustic impulse generator for processing and/or storage in memory at the acoustic impulse generator and/or a remote server for processing and/or storage in memory.

In step 2005, the arrival time $t_0$ of the preflexural impulse is computed. For example, as shown in FIG. 20B, the arrival time of the preflexural impulse may be computed by detecting a zero crossing in the preflexural impulse data. Likewise, in step 2007, the arrival time $t_1$ of the flexural impulse is computed. For example, as shown in FIG. 20B, the arrival time $t_1$ of the flexural impulse may be computed by detecting a zero crossing in the flexural impulse data. In step 2009, an arrival time difference $t_1-t_0$ is computed. In step 2011, the fill level is computed based on the arrival time difference $t_1-t_0$. Alternatively, in accordance with one or more embodiments, a cross-correlation computation between the flexural impulse data and the preflexural impulse data may be used to compute $t_1-t_0$, wherein the maximum value of the cross-correlation determines the offset between the two datasets.

Advantageously, the above method allows for the reduction of timing uncertainties because the preflexural wave provides an accurate and repeatable $t_0$ reference. Additionally, the above method provides a way to apply environmental compensation to the readings, specifically temperature effects. Higher temperature causes both the preflexural and flexural waves to slow down. Accordingly, a temperature-corrected flexural wave travel time may be obtained by scaling this measured time based on the % change of the preflexural arrival time. Accordingly, temperature effects on travel time in large tanks, which can be appreciable, are compensated for.

As described above, in accordance with one or more embodiments of the invention, reference point detection is used, both to compute the first impulse arrival time $t_0$ and to compute the second impulse arrival time $t_1$. Thus, in order to compute accurate total travel time $\Delta t=t_1-t_0$ in accordance with one or more embodiments of the invention, a method for detecting reference points, e.g., zero crossings is used that leads to a repeatable and consistent tracking of a reference point, e.g., a zero crossing on a waveform as subsequent measurement are made, as described in more detail below in reference to FIGS. 21-23. Alternatively, in accordance with one or more embodiments, a cross-correlation computation between the first impulse data and the second impulse data may be used to compute $t_1-t_0$, wherein the maximum value of the cross-correlation determines the offset between the two datasets.

Furthermore, while the examples of zero crossings are used in the example laid out above for determining $t_0$ and $t_1$, any reference point may be used without departing form the scope of the present disclosure. For example, $t_0$ and $t_1$ may be chosen to be times at which peaks occur in the dataset. In addition, for example, $t_0$ may be determined by choosing any point in the first impulse data that occurs between a zero crossing and a peak without departing from the scope of the present disclosure. For example, such an arbitrary point may be determined by selecting a point in the first impulse that whose amplitude value falls within a predefined range of values. Once of ordinary skill having the benefit of this disclosure will appreciate that the interpolation procedure described above in the context of zero crossing interpolation may also be applied for any point without departing from the scope of the present disclosure.

Figure 21:
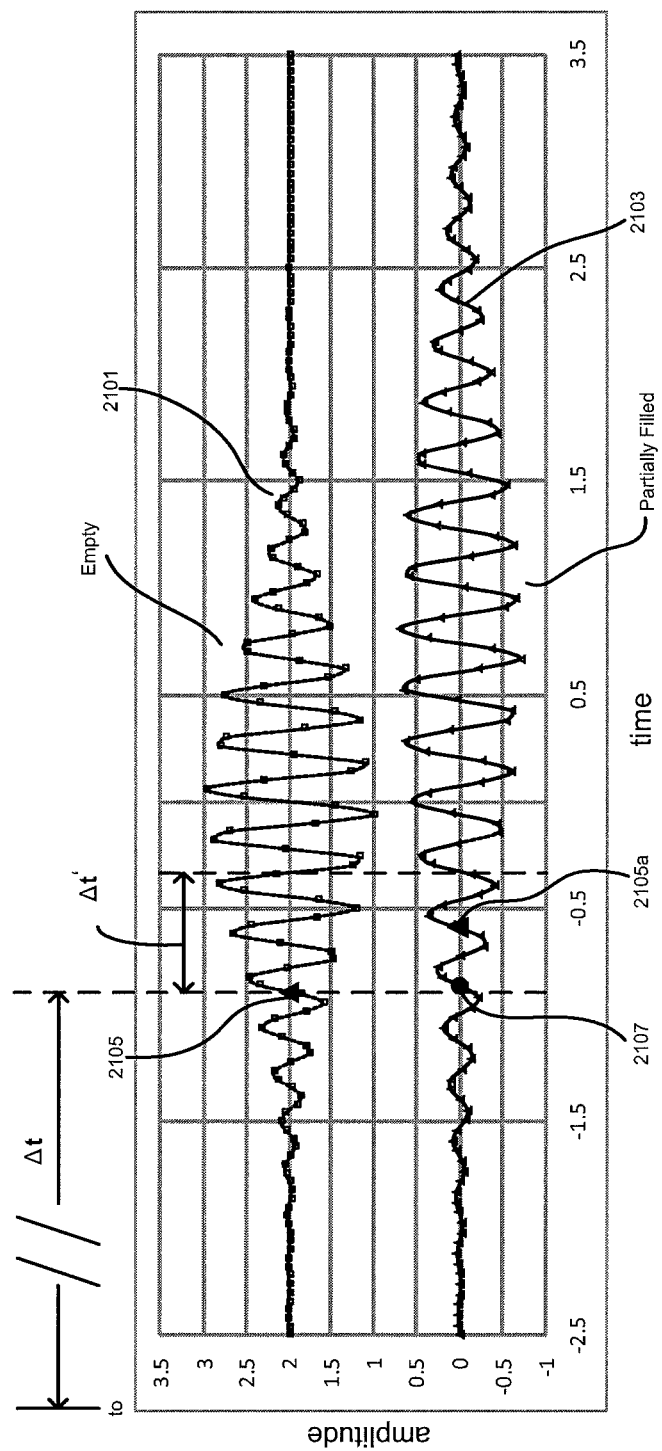
FIG. 21 shows an example of acquired acoustic impulse data.

FIG. 21 shows one example of an acoustic impulse data measured by either an acoustic impulse generator or an acoustic impulse receiver. As discussed above, in reference to FIG. 11, both the speed and dispersion of a flexural acoustic impulse is affected by the presence of fluid in the vessel. FIG. 21 shows two examples of impulse data. Accordingly, waveform 2101 is an example of a waveform that has propagated in an empty tank while waveform 2103 is an example of a waveform that has propagated in a partially full tank. FIG. 21 shows that fluid in the tank results in a waveform that is both shifted in time and dispersed as compared to a waveform that has propagated in an empty tank. To compute the fluid level in the tank, the total travel time $\Delta t = t_1 - t_0$ is computed as described above. To a first approximation, $t_0$ may is a fixed reference but various noise sources may lead to fluctuations in the acquired data within the acquisition window. In addition, $t_1$ may vary due to noise and more fundamentally, depending on the fluid level in the tank. Accordingly, the zero crossings 2105 and 2107 chosen as the reference points for the $t_1$ measurement must be tracked from measurement to measurement. For example, a measurement may begin by choosing the zero crossing to be the Nth zero crossing 2105 near the beginning of the impulse.

For simplicity, in what follows, an example limited to the zero crossing as the point chosen. However, one of ordinary skill having the benefit of this disclosure will appreciate that any point may be used without departing from the scope of the present disclosure. For example, while zero crossings may be located by selecting only those points within a predetermined data window centered at zero, any other point may be chosen by using any other window.

Returning to FIG. 21, zero crossing 2105 (or more generally any reference point in the dataset, as noted above) may be initially chosen using data processing algorithms that are commonly known in the art, e.g., by applying thresholding and/or windowing functions to the dataset. Furthermore, for low noise datasets and/or when the tank is filling or emptying slowly, the zero crossing 2105 may be effectively tracked in subsequent measurements by choosing the zero crossing 2107 in the subsequent dataset that occurs nearest in time to the initially chosen zero crossing 2105. While this "auto-tracking" method works well for slowly varying datasets, the method fails if the fluid level in the vessel changes abruptly between measurements, as is shown in FIG. 21 of if there is a time shift error of more than one wave period between measurements. For the case shown in FIG. 21, the fluid level has changed dramatically between the times when waveforms 2101 and 2103 are acquired. However, auto-tracking the zero crossing 2105 would lead to zero crossing 2107 being picked and consequently a measurement that indicates a fluid level has not changed. In reality, the fluid level has changed dramatically. In fact, as measured from the proper zero crossing of 2105a, an added propagation delay $\Delta t'$ is present relative to the original measurement of waveform 2101, due to the presence of extra fluid in the vessel.

Figure 22:
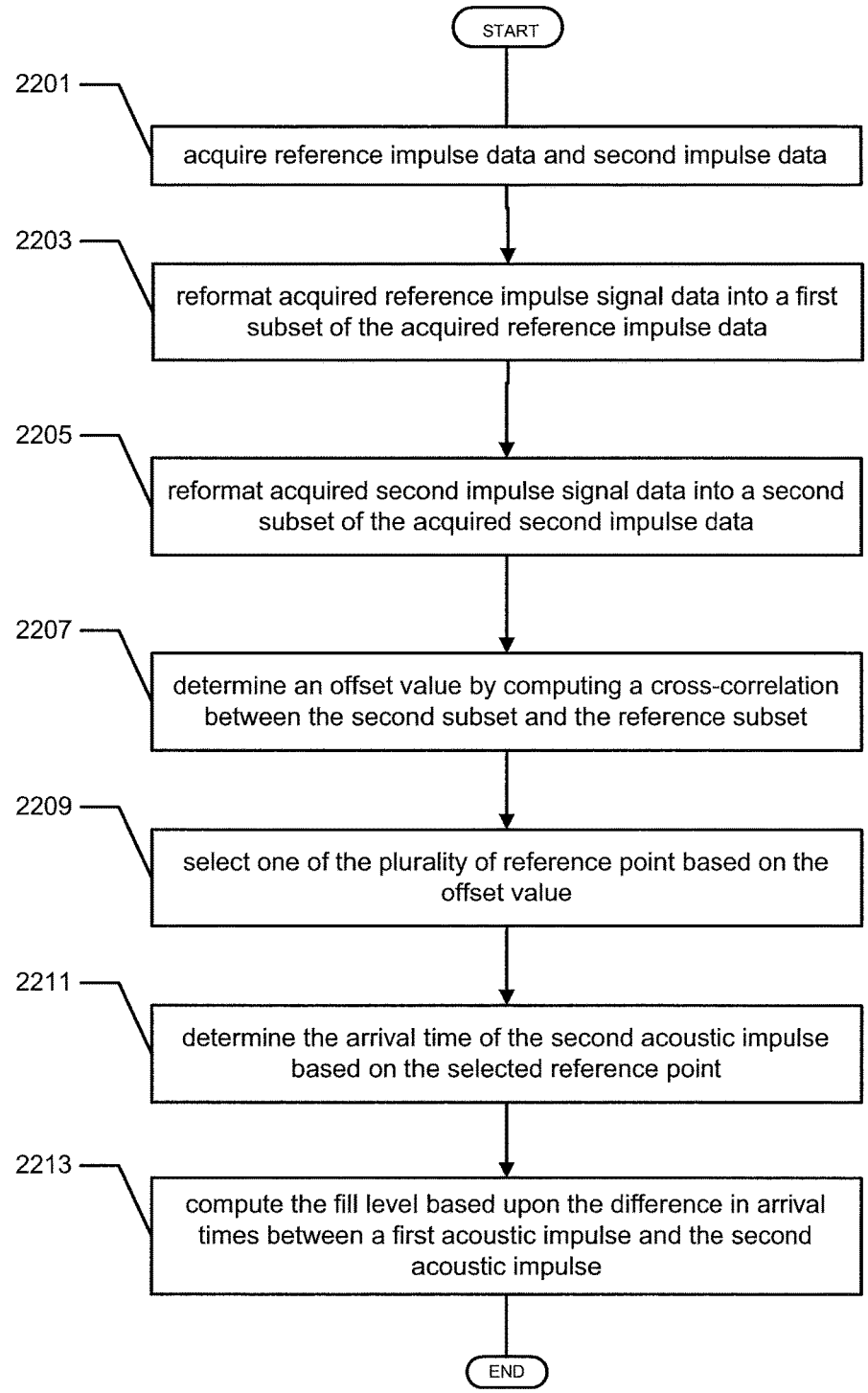
FIG. 22 shows a flow chart describing a method for reformatting and/or compressing acoustic data in accordance with one or more embodiments of the invention.

FIG. 22 shows a flow chart describing a method for reliably computing reference data points in acoustic impulse data, and thus, reliably computing $t_0$ and/or $t_1$ in accordance with one or more embodiments of the invention. The acoustic impulse data may be obtained in any way. For example, the acoustic impulse data may be flexural and/or preflexural wave data obtained by an acoustic impulse generator, as described above in reference to FIGS. 10 and 11. Furthermore, the acoustic impulse data may be preflexural and/or flexural wave data acquired by an acoustic impulse receiver, as described above in reference to FIGS. 10-11.

In step 2201, reference impulse data and second impulse data is acquired. In accordance with one or more embodiments, the reference impulse data may be acoustic impulse data that was previously acquired and stored in memory as a reference. In this example, the reference impulse data is a propagated initial acoustic impulse that is chosen as a reference for a subsequent zero crossing computation using subsequently acquired second impulse data. For example, the reference impulse data may be a series of samples of waveform 2101 and the second impulse data may be waveform 2103, as described above. In addition, examples of the reference impulse data and the second impulse data are shown in FIG. 21 as waveform 2101 and 2103, respectively. Furthermore, the second impulse data is impulse data that is acquired either by the impulse receiver or the impulse generator and is to be used to compute the fill level in the vessel. The reference impulse data and/or the second impulse data may be stored in the internal memory of the acoustic impulse receiver or, after acquisition, the reference impulse data and/or the second impulse data may be transmitted to the acoustic impulse generator or a remote server and stored for further processing.

In one example, the method for computing the reference data points in impulse data is accomplished by choosing a zero crossing in the second impulse data by referencing a zero crossing in the reference impulse data as described in more detail below. However, one of ordinary skill in the art having the benefit of this disclosure will appreciate that any point may be used and accordingly, the present disclosure is not limited only to embodiments that select zero-crossing points as the reference data points. In accordance with one or more embodiments, once the reference data point, e.g., a zero crossing, in the second impulse data is chosen, the fill level may be determined by computing the time delay between the arrival of a previously acquired first acoustic impulse and the second acoustic impulse, as described above in reference to FIGS. 11, 14, 17, 18, 20, and 22. While the example described here is directed to second wave impulse data acquired by the acoustic impulse receiver, and, accordingly, the determination of $t_1$, the method may equivalently be used to track reference points, e.g., zero crossings, in first impulse data, acquired by either the acoustic impulse receiver or the acoustic impulse generator and, thus, provides for an accurate method to compute $t_0$, $t_0'$, and/or $t_1$.

In step 2203 the reference dataset is further processed by reformatting the data into a reference subset of the reference impulse data. In accordance with one or more embodiments, reformatting accomplished by first parsing the reference impulse data to generate a subset of the reference impulse data that includes, e.g., peak data points and adjacent data points that are adjacent to the reference data point, e.g., zero crossing points, as shown by the data points joined by the set of solid lines 2303 of FIG. 23. The data is further processed to precisely compute the reference points, e.g., zero crossing points, associated with each rising slope that is adjacent to a respective peak. For example, in accordance with one or more embodiments, the zero crossing 2305 that is associated with peak 2307 may be determined from the x-intercept of a linear interpolation between points 2309 and 2311. Alternatively, if one of the points associated with the peak is within a predetermined threshold value, for example 0.05, the point may be automatically chosen as the zero crossing without the linear interpolation described above. For example data point 2313 may be chosen to be the zero crossing associated with the peak 2315. In yet other embodiments, the reference point may generally be determined by a linear interpolation between two arbitrarily chosen values, or may be chosen as a value that falls within a predetermined upper and lower threshold value, in other words, the reference point need not be a zero crossing.

After all zero crossings and associated peak amplitude values are computed, these values are stored in memory as the reference subset of the acquired reference impulse data. In this way, the acquired reference impulse data is reformatted and compressed to allow for more efficient processing and use of on-board memory. An example of a reference subset is shown as data 2317 in FIG. 23, as computed from acquired waveform 2301. Each data point in the reference subset data 2317 corresponds to a zero crossing and peak amplitude value from acquired reference waveform 2301. For example, point 2307a corresponds to peak data point 2307 and zero crossing 2305 and point 2315a corresponds to peak 2315 and zero crossing 2313. While this example describes a parsing of the original data set using only rising slope data, falling slope data may be used without departing from the scope of the present disclosure.

In step 2205 the same reformatting process from step 2203 is applied to the second impulse data to generate a second subset of the second impulse data.

Figure 24:
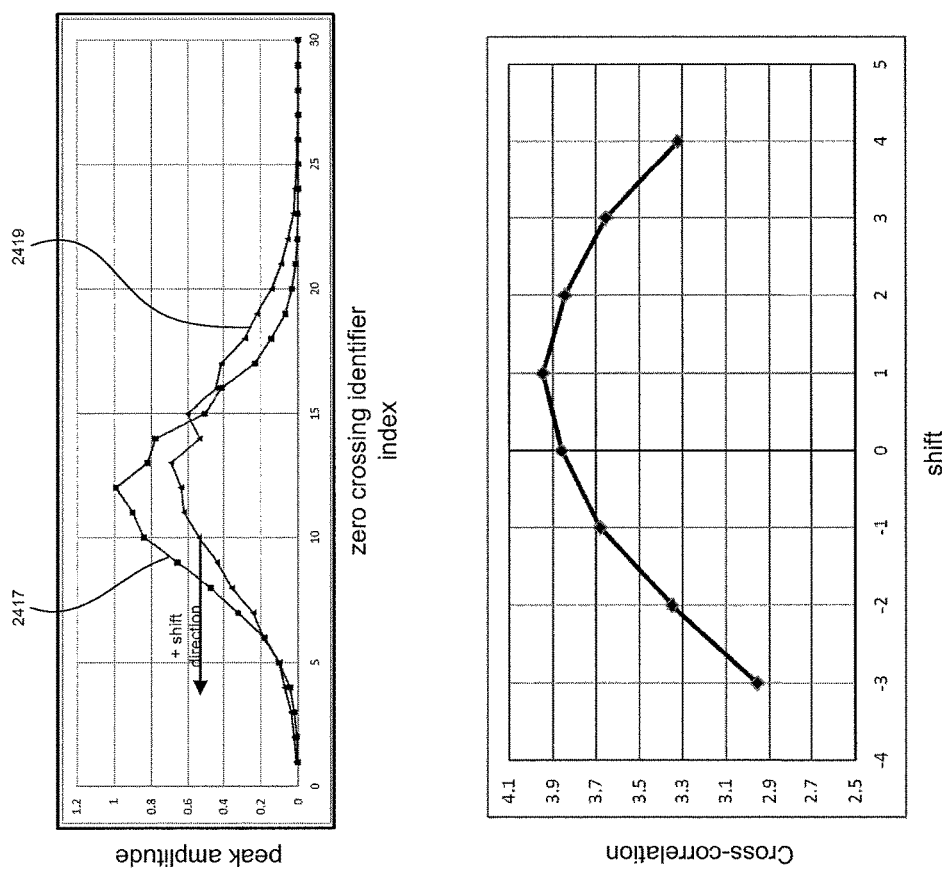
FIG. 24 shows examples of cross-correlated acoustic data in accordance with one or more embodiments of the invention.

In step 2207 an offset value Δ between the reference subset and second subset by computing the peak of a cross-correlation measurement between the second subset and the reference subset. In accordance with one or more embodiments, the $i^{th}$ element of the cross-correlation $C_i$ of the two datasets is defined by the equation:

$$C_i = \sum_{j=-\infty}^{\infty} x_j y_{i+j},$$

where $x_i$ is the i-th element of the reference subset x of having length N: $x=[x_1, x_2, \ldots x_N]$ and $y_i$ is the i-th element of the second subset y having length M: $y=[y_1, y_2, \ldots, y_M]$. FIG. 24 shows an example of a cross correlation computation of the reference subset 2317 and the second subset 2319. FIG. 24B shows that for this example, the cross-correlation between the two subsets peaks at 1, indicating a shift of 1 element (i.e., a shift of 1 zero-crossing) between the two datasets.

In step 2209 one of the plurality of second zero crossings is selected based on the shift computed in step 2207. To continue with the example above, if the i-th zero crossing of the reference subset is chosen as the reference zero crossing, the i+1 element is chosen as the second zero crossing. More generally, the i+Δ element of the second subset is chosen as the zero crossing used to determine $t_1$ for the subsequent fill level measurement.

In step 2213 the fill level is computed based on Δt, where Δt=$t_1$−$t_0$ as described above in reference to FIGS. 11, 14, 17, 18, 20, and 22. As described above, $t_0$ is the arrival time of a first acoustic impulse and $t_1$ is the arrival time of the second acoustic impulse as determined using the cross-correlation method described above.

In general, the peak of the cross-correlation measurement is used to compute the shift Δ between the reference subset and the second subset. Advantageously, this method provides for an accurate way to track the zero crossing from which $t_1$ is derived from measurement to measurement, even if the fill level in the vessel changes abruptly in between measurements. In addition, reformatting the waveform data into a subset of data as described above results in a compression of the data of a factor of anywhere from 10-30. Advantageously, the data compression that results from reformatting the data before cross-correlation results in both low memory requirements and lower processing power requirements of both the acoustic impulse generator and receiver hardware and, thus, low cost and low power consumption for these devices.

While the example method described above uses a cross-correlation technique to accurately determine the reference point, e.g., zero crossing, chosen in a second acoustic impulse to determine the arrival time ($t_1$) of the second acoustic impulse, the same technique may be used to accurately locate the reference point, e.g., zero crossing, chosen in a first acoustic impulse to determine the arrival time ($t_0$) of the first acoustic impulse. This alternative method may be used both for first acoustic impulses that are measured at the acoustic impulse generator and for acoustic impulses comprising preflexural waves that are measured at the acoustic impulse detector. It should be noted that in each case, the cross-correlation measurement is between a reference first acoustic impulse and a subsequently measured first acoustic impulse or, as described above, a reference second acoustic impulse and a subsequently measured second acoustic impulse. Accordingly, the cross correlation measurement allows for accurate and consistent picking of reference points used for either or both of $t_1$ or $t_0$. The impulse travel time is then determined from Δt=$t_1$−$t_0$, as described above.

One of ordinary skill will also appreciate that a different method may be deployed that relies on a cross-correlation measurement of the first acoustic impulse and the second acoustic impulse to determine the propagation time in the vessel wall. In such a method, the time shift determined from the cross-correlation measurement is Δt. In accordance with one or more embodiments, the time shift Δt may be determined from first locating the time at which the peak values of the first acoustic impulse and the second acoustic impulse are acquired. Then, the propagation time is determined by subtracting these two times. Both of the alternative embodiments of determining Δt may be used with the level sensor of the present invention, but are most effective in low acoustic noise environments.

In accordance with one or more embodiments, the system may employ only a single receiver, located at an end of the tank opposite to the generator. In this system $t_0$ may be set as the time the servo or solenoid in the in the generator is triggered. In accordance with one or more embodiments, the use of the wavefront arrival dispersion method with cross-correlation allows for an accurate level detection using only a single receiver. In this example, the timing of the generator does not need to be known other than for use in a dead-reckoning timing scheme to sync the gating and cross-correlation window of the receiver. In this example, the fluid level is entirely determined by the dispersion of the impulse measured at the receiver and the timing between the generator and the receiver is not used to compute the fill level. Likewise, only a single receiver is necessary of using the preflexural wave as the $t_0$ reference. Advantageously all of these single receiver embodiments, reduce the complexity and cost of circuitry, parts and makes for a very simple and robust system.

Figure 25A:
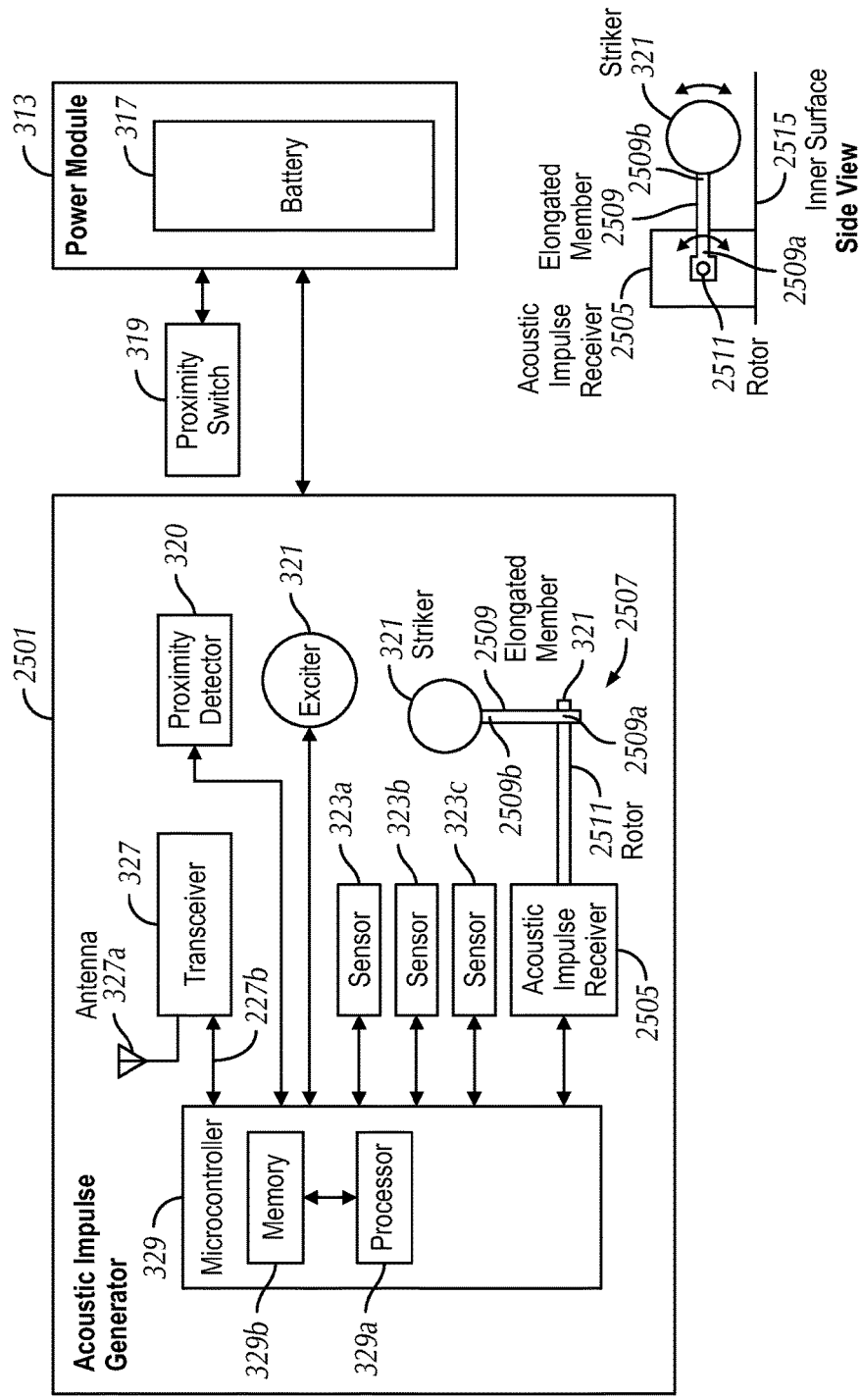
FIGS. 25A-25B shows examples of an acoustic impulse generator and an acoustic impulse receiver, respectively, in accordance with one or more embodiments of the invention.
Figure 25B:
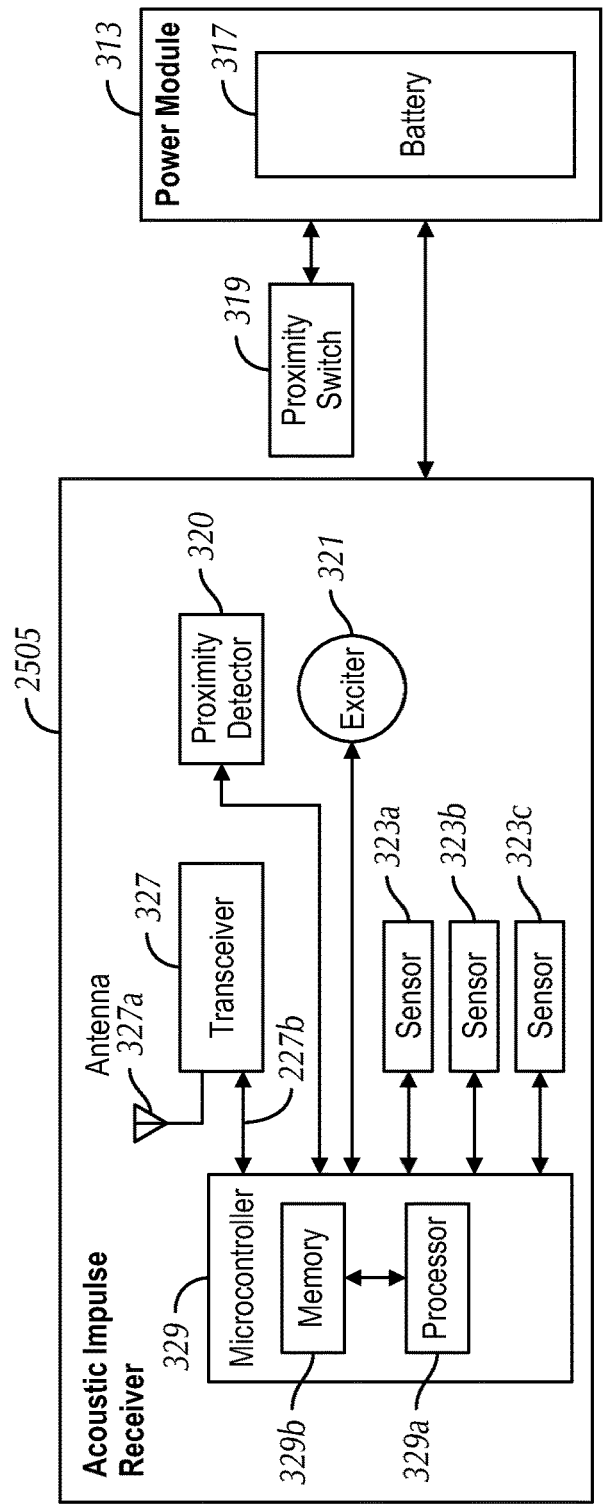

FIGS. 25A-B show examples of wireless sensor modules in the form of an acoustic impulse generator and an acoustic impulse receiver in accordance with one or more embodiments of the invention. Generally speaking, the acoustic impulse generator 2501 and the acoustic impulse receiver 2505 are remote wireless sensor modules as described above in FIGS. 3A-3C. Accordingly, like elements are labeled with like numerals and the detailed description of these elements will not be repeated here for sake of brevity. However, as shown in FIGS. 25A-25B, the acoustic impulse generator 2501 is a wireless sensor module that has been adapted to generate and receive acoustic impulses. More specifically, the acoustic impulse generator 2501 includes a striking mechanism 2507 that is mounted to a rotary 2511. In accordance with one or more embodiments, the entirety of the striking mechanism 2507 is mounted within the enclosure of the acoustic impulse generating module. The striking mechanism is formed from an elongated member 2509 that is attached at one end 2509*a* to a rotor 2511 of a rotary actuator (not shown) in the acoustic impulse receiver 2505. Accordingly, a second end 2509*b* of the elongated member 2509 is free to move in response to the rotation of the rotor 2511. In accordance with one or more embodiments, the rotor 2511 rotates about axis 2505*a*. Fixed at end 2509*b* of elongated member 2509 is a striker 2513 that is configured to strike an inner surface 2515 of the enclosure of the acoustic impulse generator. In accordance with one or more embodiments, the enclosure is identical to the enclosure described above in reference to FIGS. 3A-3C. In accordance with one or more embodiments, the rotary actuator is a micro rotary servo having a rotor that can be set in 1 degree increments via commands from microcontroller 329. In accordance with one or more embodiments, striker 2513 may be made of any material and be of any shape and weight. However one embodiment of the striker 2513 is a spheroidal shaped lead weight that weighs approximately 1 oz. In accordance with one embodiment, the servo is configured to rotate at an angular velocity of approximately 300 degrees per second. However, many different angular velocities may be used without departing from the scope of the present disclosure.

In accordance with one or more embodiments, other forms of acoustic impulse generation may be used. For example, a small solenoid actuator may be used, in which the solenoid throw rod assembly may be placed such that it strikes the inside wall of the enclosure that is placed against the wall of the vessel when the solenoid device is actuated. Other devices include but are not limited to linear actuators, eccentric motors, haptic actuators, electromagnetic actuators, bimetallic strips, shape memory wire, such as NITINOL and FLEXINOL, piezoelectrics, speakers or exciters, shape memory allow actuators, and Miga nanomuscle motors.

In accordance with one or more embodiments, acoustic impulse generator is equipped with several sensors 323*a*, 323*b*, . . . , 323*c* as described above in reference to FIGS. 3A-3C. While three sensors are shown here for simplicity, the acoustic impulse generator may be equipped with any practicable number of sensors. In particular, the acoustic impulse generator is equipped with an acoustic sensor in the form of microphone 323*a* for recording the acoustic impulse generated when the striker strikes the inner surface of the enclosure. As described above, the acoustic impulse generator is affixed to a vessel for housing a fluid. The enclosure of the acoustic impulse generator may be affixed to the vessel in an identical manner to that described above, e.g., by way of adhesive tape. Accordingly, the acoustic impulse generated by the striker is effectively coupled into the wall of the vessel whose fill level is to be measured.

As described and shown above, an acoustic wave may be created by banging a servo arm or solenoid throwbar directly at the tank in a direction normal to the tank wall. However, alternate methods of acoustic wave generation may be employed without departing from the scope of the present disclosure. For example, the side of the module that is perpendicular to the tank surface may be hit so that most of the energy will be transferred by shear to concentrate on the axial direction of the tank. In this manner, the compressional energy will be maximized with a corresponding reduction of flexural energy.

FIG. 25B shows a block diagram of an acoustic impulse receiver in accordance with one or more embodiments of the invention. Generally speaking the acoustic impulse receiver 2505 is a wireless sensor module as described above in FIGS. 3A-3C. Accordingly, like elements are labeled with like numerals and the detailed description of these elements will not be repeated here for sake of brevity. However, as shown in FIG. 25B, the acoustic impulse receiver 2505 is a wireless sensor module that has been adapted to receive acoustic impulses that are generated by acoustic impulse generator 2501. Accordingly, the acoustic impulse receiver is equipped with an acoustic sensor in the form of microphone 323*a* for recording the acoustic impulse generated by the striker after the impulse travels a length along the vessel defined by the separation between the acoustic impulse receiver 2505 and the acoustic impulse generator 2501. As described above, the acoustic impulse receiver is affixed to a vessel for housing a fluid. The enclosure of the acoustic impulse generator may be affixed to the vessel in an identical manner to that described above, e.g., by way of adhesive tape.

In accordance with one or more embodiments, the acoustic impulse receiver 2505 and the acoustic impulse generator 2501 are configured to communicate with each other wirelessly by way of transceivers 327. Furthermore, the acoustic impulse receiver 2505 and the acoustic impulse generator 2501 may communicate with a wireless gateway module or a wireless repeater module as described above in reference to FIGS. 4A-4C. For the sake of brevity, the communication protocol between a wireless sensor module and a wireless gateway module is not repeated here.

Figure 26A:
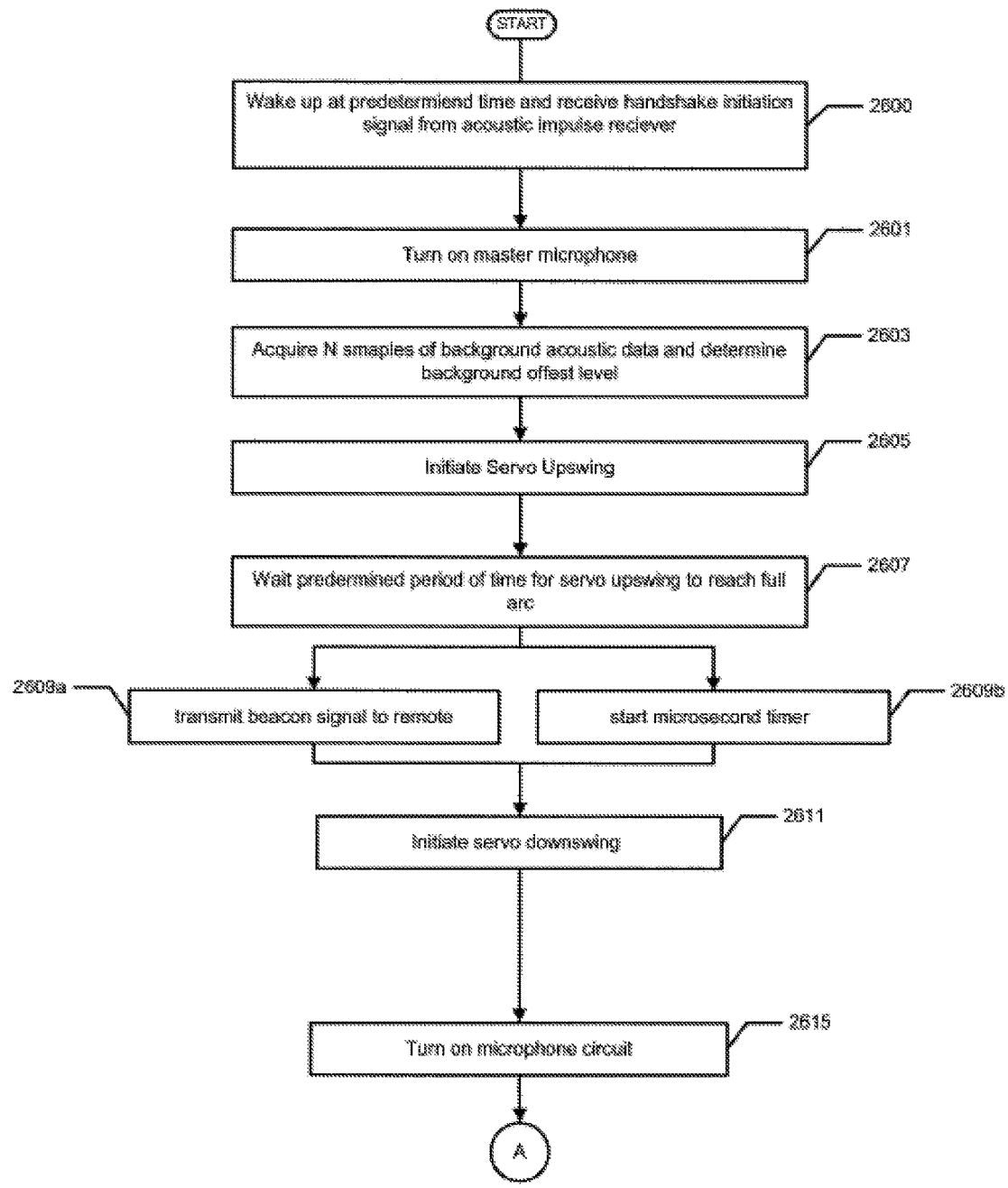
FIGS. 26A-26B shows a flow chart describing a method of operation and communication of an acoustic impulse generator in accordance with one or more embodiments of the invention.
Figure 26B:
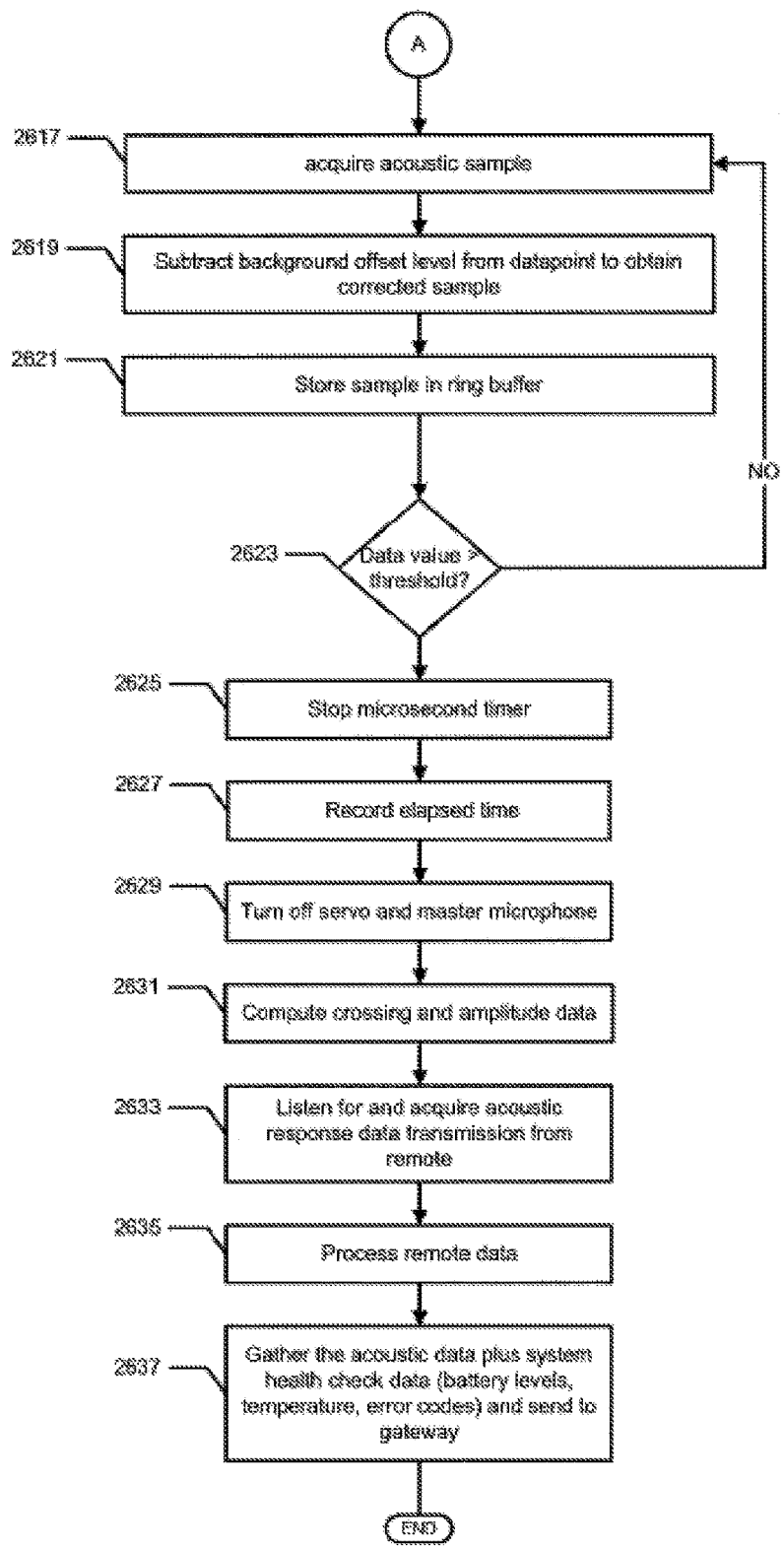

FIG. 26A-26B shows a flow chart describing a method of operation and communication of an acoustic impulse generator in accordance with one or more embodiments of the invention. In step 2600, the acoustic impulse generator wakes up at a predetermined time and handshakes with the acoustic impulse receiver to initiate the acquisition sequence. In accordance with one or more embodiments, the handshaking is accomplished by any known handshaking protocol. In step 2601, the power to the acoustic impulse generator microphone (e.g., microphone 323*a*) is turned on. In step 2603, the acoustic impulse generator acquires a number of samples of background acoustic data (e.g., 10 acoustic samples), and using the microphone and microcontroller of the acoustic impulse generator processes this data to determine the current level of background offset noise. The background offset noise value is then stored in memory for use in correcting subsequently acquired data samples.

In step 2605, a command is sent from the microcontroller to the rotary actuator (e.g., a digitally controlled servo motor) to initiate the upswing of the striking mechanism. In step 2607, the system waits a predetermined period of time for the striking mechanism to reach full arc. In step 2609*b* and 2609*a*, a microsecond timer in the CPU module is started and a beacon signal is sent to the acoustic impulse receiver to initiate the receiver acquisition sequence.

In step 2611, a command is sent from the microcontroller to the rotary actuator to initiate the downswing of the striking mechanism. In step 2615, the microprocessor sends a signal to the microphone circuit to turn on the microphone circuit (e.g., the circuit may include buffers, amplifiers, receivers, or the like, as is known in the art). In step 2617, the acoustic impulse is recorded by the microphone of the acoustic impulse generator. In accordance with one or more embodiments, the microcontroller is configured to acquire at least one acoustic impulse data point by sampling the signal from the microphone at a set time interval. In step 2619, each time a sample is acquired, the background noise offset is subtracted to obtain a corrected data sample. In step 2621, the corrected data sample is stored using a line or ring buffer acquisition loop. In step 2623, the most recently stored sample is compared to a predetermined threshold value to determine whether or not to stop the acquisition. This threshold value is pre-programed to ensure that a significant fraction of the acoustic impulse is acquired (i.e. to ensure that the data acquired is actually representative of the microphone acquisition after the striker hits the enclosure wall). In step 2625, the microsecond timer is stopped and in step 2627 the elapsed time is stored in memory. In step 2629, the microcontroller sends a command to turn off the rotary actuator and the microphone circuit. In step 2631, a subset of the acquired data is optionally computed by reformatting the data in the form of amplitude and reference point, e.g., zero crossing, data, as described above in FIGS. 21-23. In step 2633, the acoustic impulse generator waits for the acoustic impulse receiver to collect and send data back to the acoustic impulse generator (e.g., for a typical measurement, this may take a few milliseconds). In accordance with one or more embodiments, the microcontroller of the acoustic impulse receiver processes the acquired data. For example, the microcontroller may backtrack through the ring buffer to locate the zero crossing just prior to the end of data acquisition. The crossing is then interpolated using the prior and post amplitude values as a ratio. The crossing time is then reported to the nearest microsecond. Once the acoustic impulse data is received from the acoustic impulse receiver, the data is further processed in step 2635, e.g., to correct the data to account for the elapsed swing time and the small correction to the reference point, e.g., zero crossing. In step 2637, the acoustic data is gathered with system health check data (e.g., battery levels, temperature, error codes, etc.) and this data is transmitted to the wireless gateway module.

Figure 27:
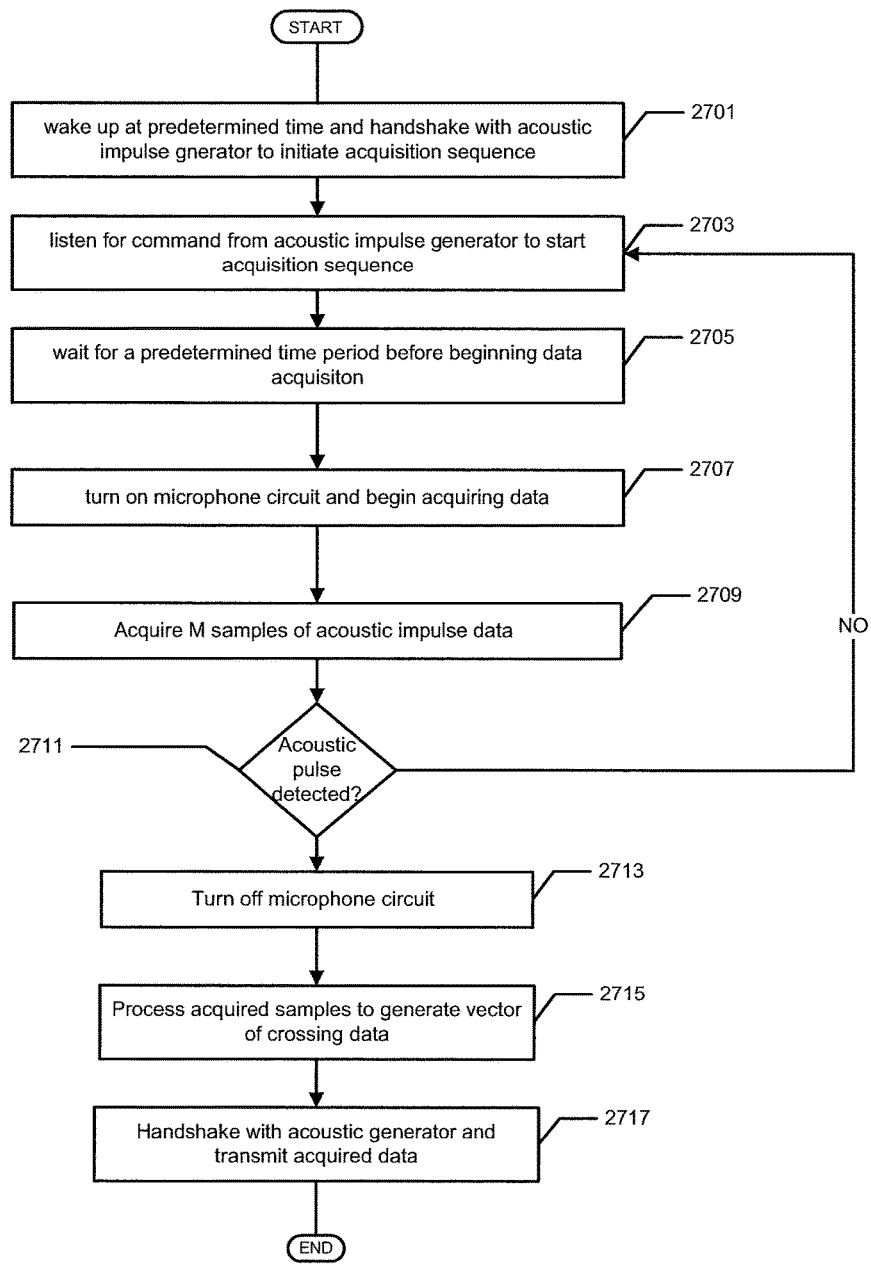
FIG. 27 shows a flow chart describing a method of operation of an acoustic impulse receiver in accordance with one or more embodiments of the invention.

FIG. 27 shows a flow chart describing a method of operation and communication of an acoustic impulse receiver in accordance with one or more embodiments of the invention. In step 2701, the receiver wakes up at a predetermined time and handshakes with the acoustic impulse generator to initiate the acquisition sequence. In accordance with one or more embodiments, the handshaking is accomplished by any known handshaking protocol. In step 2703, the acoustic impulse receiver listens for a beacon from the acoustic impulse generator indicating a command to start the acquisition sequence. Once the beacon is received, the acoustic impulse receiver waits a predetermined time in step 2705 before beginning acquisition of the acoustic data. In accordance with one or more embodiments, the predetermined time is computed by, e.g., the remote server stored in the internal memory of the respective receiver/generator. Furthermore, as described above, the predetermined time is based on computations that use a physical model of acoustic impulse propagation in a tank of the type being monitored.

In step 2707, the microcontroller of the acoustic impulse receiver turns on its microphone circuit. In step 2709, the microcontroller acquires a set of M samples of the signal output from the microphone circuit. In step 2701, at test is applied to the acquired samples to test if an acoustic impulse was actually acquired in step 2709. For example, the data may be tested to see if the amplitude of any of the acquired samples falls above a predetermined threshold value. If, in step 2711, it is determined that a suitable acoustic impulse has not been acquired, e.g., the acoustic impulse is not discernible from the noise level, the system returns to step 2703 and waits for another beacon from the generator to start another acquisition. The generator sends an 'All ok" or else a 'get ready for another sample' command when it assesses the data quality. In accordance with one or more embodiments, the acoustic impulse receiver may be preprogramed to retry data acquisition a set number of times, e.g., three times before returning to a low power sleep mode.

If an acoustic impulse is detected in step 2711, the microphone circuit is turned off in step 2713. In step 2715, the acquired data is processed. For example, the data may be parsed into a series of samples that include amplitude values and crossing data values as described above in reference to FIG. 21-23. In addition, the crossing data may be interpolated to create a final data subset of interpolated zero crossings using the amplitude data. As shown in FIG. 23 and described above. In step 2717, the acoustic impulse receiver handshakes with the acoustic impulse generator and transmits the acquired data to the acoustic impulse generator.

In the above description, some amount of pre-processing of the acquired data is accomplished by both the acoustic impulse generator and the acoustic impulse receiver. However, in other embodiments the raw data may be collected and transmitted to the gateway without any preprocessing. Likewise, additional processing, other than that described above may be accomplished in accordance with one or more embodiments. For example, the full fluid level computation may be done by the generator and/or receiver before the data is transmitted to the gateway. Alternatively, the raw acoustic data, or interpolated zero crossing subset may be transmitted to the gateway for further processing at the gateway or at the remote server. One of ordinary skill will appreciate that many different ways of manipulating the data before or after transmission may be employed without departing from the scope of the present disclosure.

Figure 28:
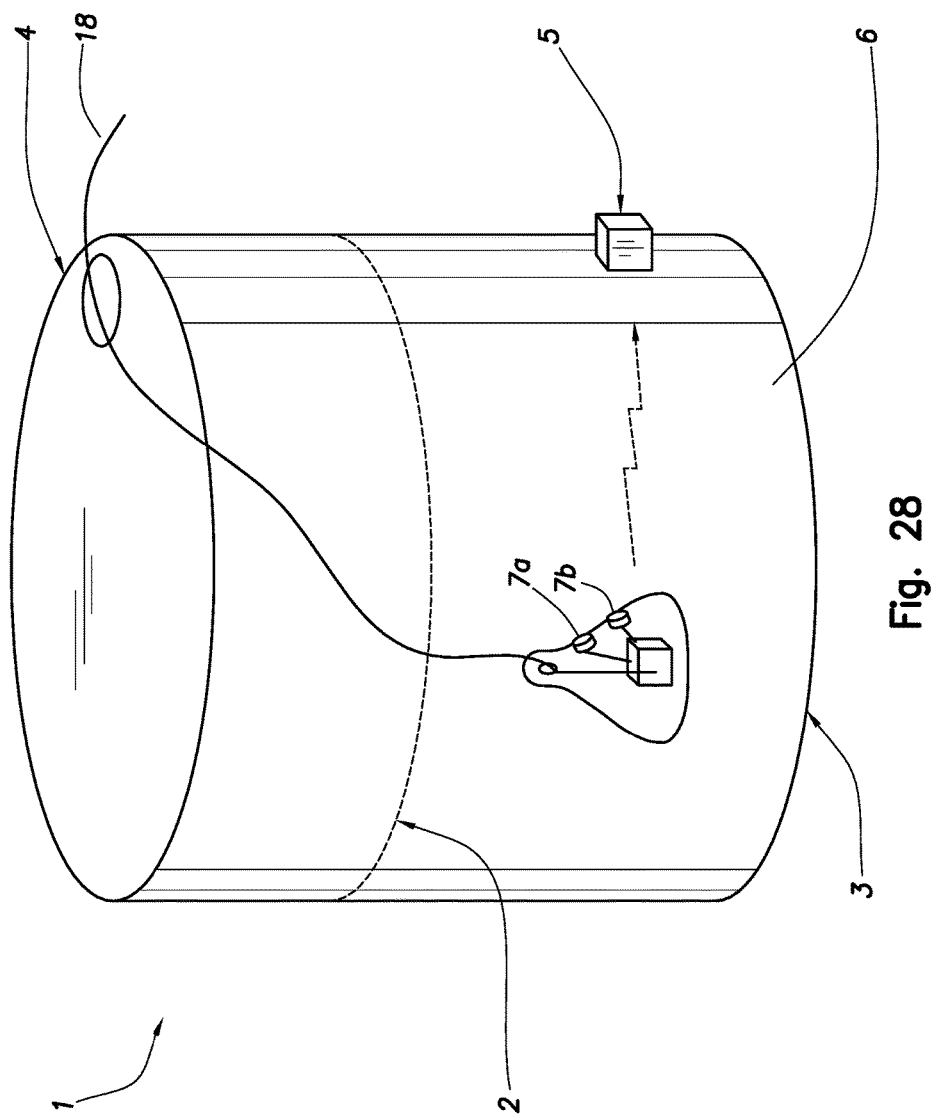
FIG. 28 shows a system for wireless tank level monitoring in accordance with one or more embodiments of the invention.

FIG. 28 shows a system for wireless tank level monitoring in accordance with one or more embodiments of the invention. In accordance with one or more embodiments of the invention, the estimated fluid levels are based on data derived from pressure measurements taken by a standalone wireless sensor module located inside the vessel. The sensor module is normally placed on the bottom of the vessel and reports readings wirelessly to a receiver-processor module located on the outside of the vessel wall.

A vessel 1 includes the fluid of interest (for instance, oil, water, or other liquid) that is filled to a certain fluid level 2 inside the vessel. The vessel can be of any size and can be either fully enclosed or open or accessible at the top. A sensor module 3 is placed inside the vessel, ideally installed by simply dropping it into the vessel via a hatch or opening 4. One of ordinary skill will appreciate that typical storage vessels employ various types of hatches or openings. Thus, the particular shape of the opening 4 depicted in FIG. 1 is for illustrative purposes only, and is not meant to limit the invention in any way. In accordance with one or more embodiments, the sensor module 3 may be powered by a power source, e.g., a battery (not shown) or other energy source, as shown in FIGS. 3A-3C and described above.

Furthermore, in accordance with one or more embodiments, the sensor module 3 is sealed and environmentally protected from the fluid in the vessel 1. The sensor module 3 includes one or more sensors 7*a* and 7*b*. In accordance with one or more embodiments, the sensor module 3 may employ a microelectromechanical (MEMS) pressure sensor. MEMS sensors include various beneficial characteristics for wireless tank level monitoring, including their extremely small size, environmentally ruggedness, low power requirements (typically 5V at 6 mA, or 30 mW), and high resolution (on the order of 10 mV per inch of water).

In accordance with one or more embodiments, the sensor module 3 wirelessly communicates with a collection module 5 that is located on the outside of the vessel. The collection module 5 may include similar processing and transmission electronics as the sensor module itself and also may additionally employ a cellular modem (e.g., a Telit CC864-Dual, or the like) for incorporating the collection module and thereby the wireless sensor module into a cellular network. Advantageously, no external wiring is necessary to install the system and the sensor data may be made available to a remote server. Advantageously, this wireless aspect makes the system portable in addition to being simple and easy to maintain. The collection module 5 may be a wireless transceiver configured to communicate with the sensor module 3. One of ordinary skill will appreciate that many protocols for wireless communication are presently known in the art and that the sensor module 3 and collection module 5 may employ any known method without departing from the scope of the present invention. In accordance with one or more embodiments, the sensor module 3 and collection module 5 may include any commercially available wireless transceiver chipsets. One of ordinary skill will appreciate that in accordance with one or more embodiments of the invention, any transceiver, receiver, and/or transmitter chipsets may be used without departing from the scope of the present invention. In accordance with one or more embodiments, the collection module is a wireless gateway as described above in reference to FIGS. 2A-2C.

Figure 29:
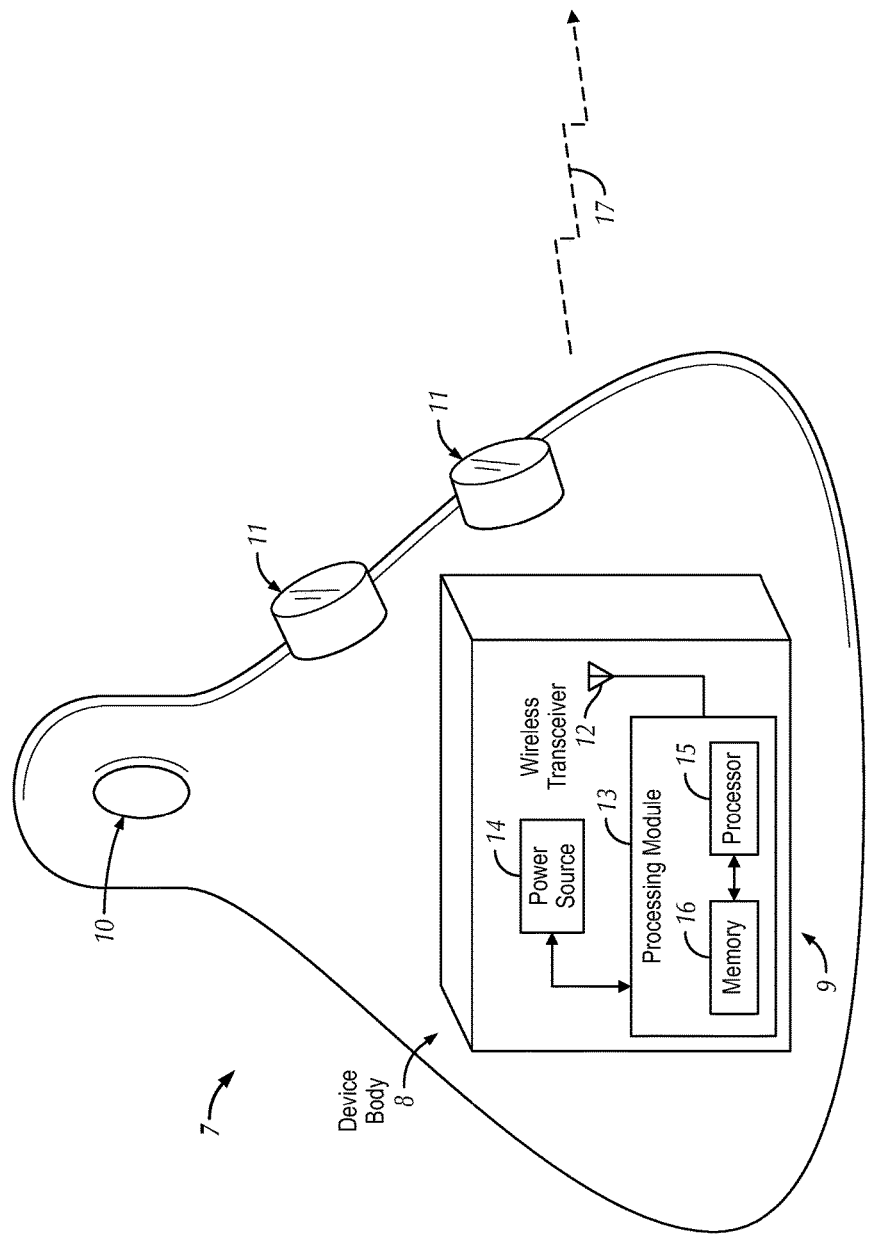
FIG. 29 shows an example of a wireless sensor module in accordance with one or more embodiments of the invention.

FIG. 29 shows an example of a sensor module in accordance with one or more embodiments of the invention. The module 7 can be fashioned of any shape or size, but preferably, the module 7 includes a very small device body 8, which is of a higher density than the fluid in the vessel so that the module 7 may be lowered by a cord or wire (as shown by cord 18 in FIG. 28) attached to the device at a convenient point 10 on the device body 8. Alternatively, the module 7 may be dropped into the vessel without being attached to a cord or wire. The device body 8 may be fluidly and/or environmentally sealed from the fluid to be measured and/or monitored, such that the internal components of the module 7 may not interact with the fluid. A series of one or more small sensors 11 of the module 7 are exposed to the fluid and thereby detect the fluid pressure and/or other fluid characteristics.

In accordance with one or more embodiments, rather than deploying wireless communication, the cord 18 may allow for wired communication between the sensor module 3 and a receiver (not shown). Such an arrangement allows for convenient deployment and retrieval of the sensor module in addition to simpler internal circuitry of the sensor module itself due to the fact that wireless transceivers and their associated control circuitry are not necessary. Returning to FIG. 29, the sensors 11 may be pressure sensors, salinity sensors, and/or other fluid characteristic sensors. Sensor readings are collected in internal electronics 9, which may include a processing module 13. In accordance with one or more embodiments, the processing module may include any microprocessor module known in the art, e.g., microprocessors such as the TI MSP430F2003, MSP430G2231, or the like, and one of ordinary skill will appreciate that the processing module may further include a processor 15, memory 16, and a wireless transceiver 12, where the sensor data are processed, stored, and transmitted wirelessly, respectively. As discussed above in reference to the collection module 5, any commercially available wireless transceivers may be used without departing from the scope of the present disclosure.

In accordance with one or more embodiments, the data is transmitted by wireless transceiver 12 wirelessly from the interior of the tank to the external collection module (not shown), e.g. through the use of RF signals 17. Field tests performed by the inventor indicate that mid-range RF signals will be able to travel outside typical steel field tanks via the small gap between the hatch cover and the top wall of the tank. The two elements are normally separated by about ½ to 1 inch by a low pressure sealing gasket, thorough which a small amount of RF signal may escape (much like the ability to get cellphone coverage inside most elevators due to the slight gaps in the exit doors). In accordance with one or more embodiments, the electronics located within the module 7 may be powered by power source 14, which may include a battery, or the like. As used herein, the term transceiver in meant broadly to encompass units known in the art to have wireless transmission capabilities only, wireless reception capabilities only, or both transmission and reception capabilities within a single unit.

In accordance with one or more embodiments, the sensor module 7 functions by taking periodic pressure measurements of the surrounding fluid. A preferred sensor type is a small MEMS device. Recent advancements in sensor technology driven by automobile real-time tire pressure measurement and medical products have driven cost and power requirements of these devices to extremely low levels. A key enabling factor has been the associated lowering of the operating pressure range of these sensors. Common and inexpensive sensors now operate in the range of 0-20 psi, providing an excellent fit for fluid pressure measurement in most vessel heights which normally do not exceed heights of ten to twenty feet.

One of ordinary skill will appreciate that the fluid height can be estimated based on the sensor module's pressure reading and knowledge of the specific gravity of the fluid in the vessel. For example, in accordance with one or more embodiments, for tanks with fluids having a density that does not vary in time, calibration may be performed in an initial two-point calibration. Subsequent measurements may then be calibrated based on a linear formula relating pressure to height using the initial two point calibration.

According to other embodiments, a more robust solution can include onboard capability to determine the fluid density. Methods of determining the fluid density include, for example, salinity based measurements. For example, in the case of water, an accurate estimate of water density can be made if the resistivity and temperature of the water are known. Thus, a sensor module including two or more electrical pads (not shown) in contact with the fluid can be used to measure the electrical resistance of the fluid in order to calculate the salinity-to-density transform. One of ordinary skill will appreciate that the conversion between salinity and density may be employed using any known method in the art without departing from the scope of the present disclosure.

In accordance with one or more embodiments, the system may be configured to undertake a differential pressure measurement. In a differential measurement method, two or more pressure sensors, or a sensitive differential pressure sensor, may be installed in a vertical array on the tank sensor module. A pressure gradient between the sensors may then be determined and used in a calculation to derive fluid height.

One of ordinary skill will appreciate that many other methods may be employed to measure fluid level in addition to the two types of methods disclosed herein. Furthermore, one of ordinary skill will appreciate that the sensors used in the sensor module disclosed herein may be of any type known in the art to measure fluid characteristics that may be used to determine a fluid level.

In accordance with one or more embodiments, several methods of wireless communication are possible. One example of a wireless communication method employs acoustic transmission, wherein sensor readings are encoded in an acoustic impulse signal. The acoustic impulse signal is transmitted by the sensor module and received by the collection module. However, because the information transfer rate in acoustic methods is normally extremely low (on the order of 1 to 5 bytes per transmission). In accordance with one or more embodiments, low frequency RF (VLF) can also be used; higher frequency RF may also be used if the transmission distance is small.

In accordance with one or more embodiments, the communication is normally one-way from sensor module to collection module. In other embodiments, the system may be configured to employ bi-directional communication.

In accordance with one or more embodiments, the sensor module is normally 'sleeping' in very low power draw mode. For many applications, level measurements are often needed only hourly or perhaps daily. Thus, the sensor module can be operated on a small battery for a long period of time, thereby minimizing the frequency of sensor module replacement.

In accordance with one or more embodiments, the sensor module is constructed from common electronics parts and can be manufactured cheaply—at a fraction of the cost of systems that are common today. Advantageously, one or more embodiments of the invention employ a sensor module that can be easily replaced by simply lowering (or dropping) a replacement into the vessel. This greatly reduces the maintenance time, cost, and skill required to use this system. Furthermore, the sensor module is designed to maintain function in harsh environmental conditions, such as wide temperature variations and corrosive fluid environments.

Figure 30:
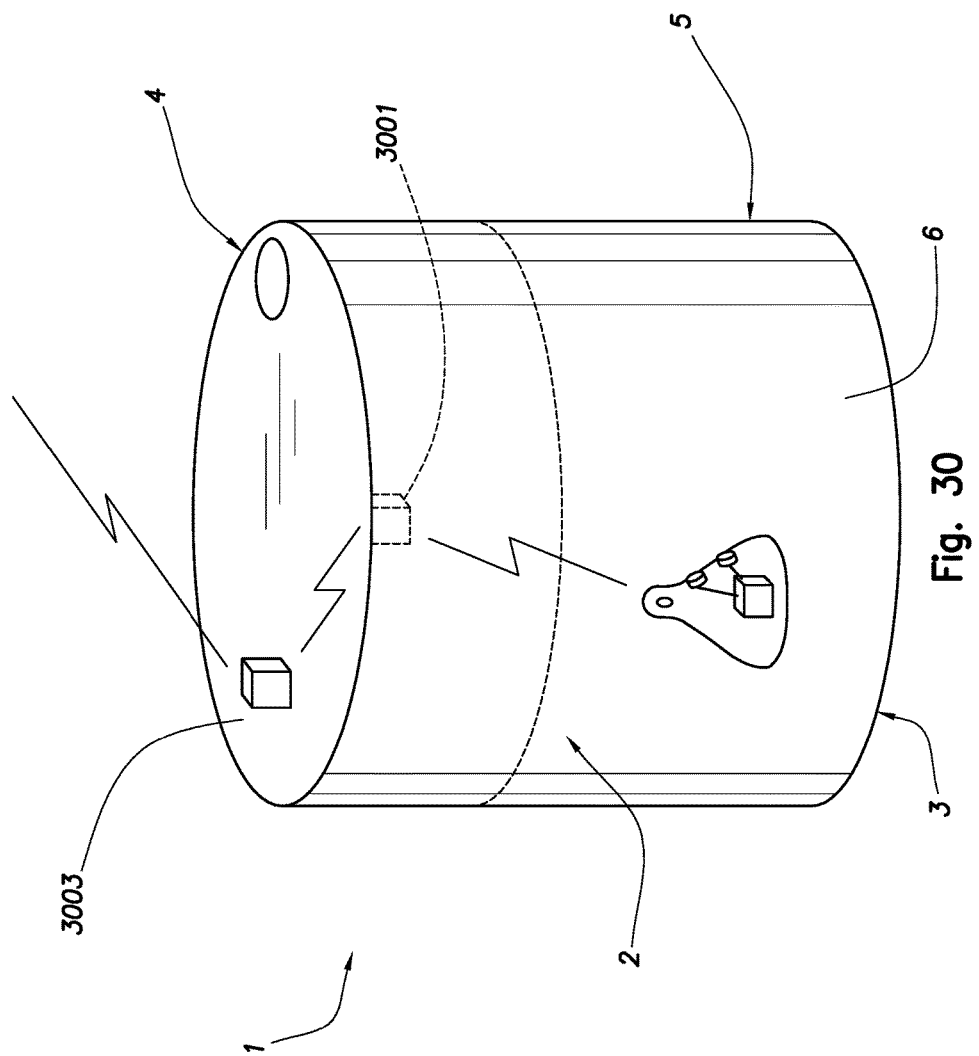
FIG. 30 shows an example of a wireless sensor module in accordance with one or more embodiments of the invention.

FIG. 30 shows an example of a wireless sensor module in accordance with one or more embodiments of the invention. More specifically, FIG. 30 shows an embodiment that is identical to that described in FIG. 28 with an added repeater unit 3001 mounted to an inner surface of the tank. The repeater unit is configured to store transmission data from the wireless sensor module 3 and to forward the data to the collection module 3003. As before, the collection module then forwards the transmission to a wireless gateway module, or alternatively, the collection module 3003 may serve as a wireless gateway itself, in which case it forwards the transmission directly to the cellular network. In accordance with one or more embodiments, the configuration shown in FIG. 30 may be beneficially deployed in tanks having metallic or otherwise conducting walls.

Figure 31:
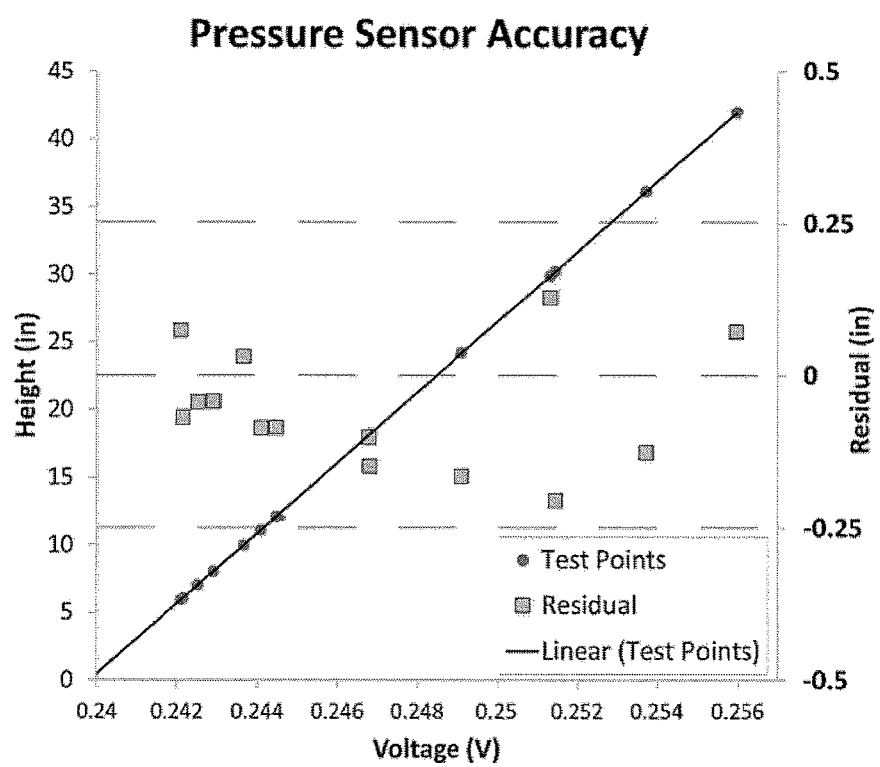
FIG. 31 shows an example calibration plot for a wireless sensor module output versus fluid level in accordance with one or more embodiments of the invention.

FIG. 31 shows an example calibration plot of sensor module output versus fluid level in accordance with one or more embodiments. As can be seen from the plot in FIG. 31, a MEMs based pressure sensor provides accurate, linear output resulting in a measurement error of less than +/−0.25 in.

Figure 32:
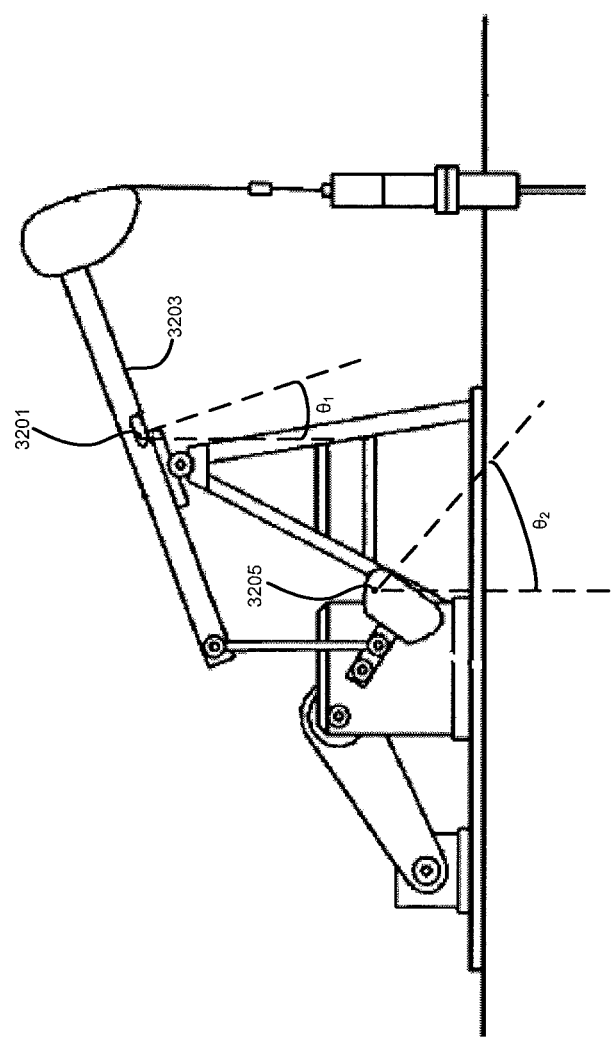
FIG. 32 shows an example of a wireless sensor module deployed as a rod pump monitor in accordance with one or more embodiments of the invention.

FIG. 32 shows an example of a wireless sensor module deployed as a rod pump monitor in accordance with one or more embodiments of the invention. The wireless sensor module is identical to the generally described wireless sensor module of FIGS. 3A-3C described above. Accordingly, the details will not be reproduced here for the sake of brevity. As described in detail above, in reference to FIG. 3, the microcontroller 329 is configured to receive sensor output from sensors 323a-323c. Furthermore, in accordance with one or more embodiments, the sensors 323a-323c include at least one accelerometer. As shown in FIG. 32, a wireless sensor module 3201 is affixed, or mounted, to walking beam 3203 near the mounting point of the walking beam 3203 to Samson post 3205. Accordingly, as the walking beam oscillates, the accelerometer provides a data stream to a microcontroller, where it is stored in memory and processed into a vector of crank angle $\theta$ versus time. This data may be transmitted to a remote server by way of a wireless gateway for further processing. For example, the angular position data stream can be converted to vertical rod position via simple trigonometry.

By providing a detailed vector of elapsed time vs. rod position for multiple points in each pumping cycle, the wireless sensor module 3201 can observe and log changes within a particular pumping cycle in addition to the total cycle time change data.

In accordance with one or more embodiments, a collection of pump signatures, i.e., relative rod position (or sensor angle as measured by the orientation of the sensor) versus time are obtained from the wireless sensor module. In accordance with one or more embodiments, the zero-crossing points on the upstroke portion of each pumping cycle are first determined. Advantageously there are normally no changes in the up-stroke portion of the cycle and zero crossings can be accurately determined by linear interpolation due to the fact the near sine wave behavior of the system approaches a linear function near the zero crossing. For noisy conditions data from several cycles can be averaged to provide a statistically improved analysis. In addition, as the pump off condition begins to occur, the cycle time of the pump also changes and this change in cycle time is logged by a change in the period of the data obtained by the sensor. In accordance with one or more embodiments, to compensate for this effect in the acquired data, the time axis may be rescaled by the measured pump period for each period that is analyzed. Thus, the shape of datasets having differing cycle times may be consistently compared.

Figure 33B:
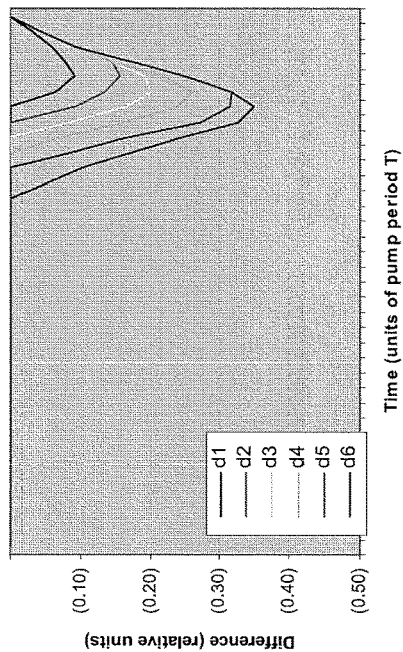
FIGS. 33A-33B show examples of data obtained by a wireless sensor module in accordance with one or more embodiments of the invention.
Figure 33A:
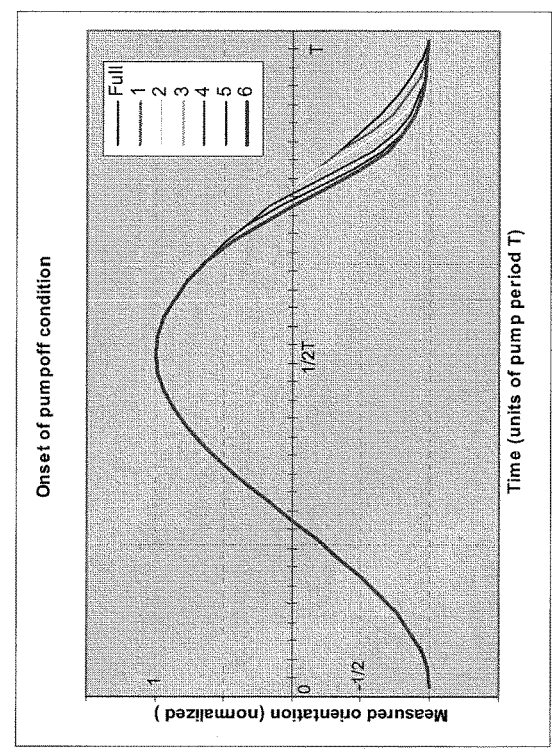

For example, FIGS. 33A-33B show examples of data obtained by the wireless sensor module with the time axis rescaled to be in units of pump period in accordance with one or more embodiments of the invention. The figure shows how progressive so called "pump-off" acts to erode the down stroke of the rod pump. A base signature vector 3301 is acquired at the initiation of a pumping cycle during the so-called "pump-up" period when the casing is full and the pump is moving 100% fluid for a short period of time. The base signature is analogous to a "fully pumping" card signature. Subsequently measured pumping signatures are successively compared with (subtracted from) the subsequent normalized cycle data as pumping progresses, as shown in FIG. 33B. As a result, a semi-quantitative analysis of the progressing pump-off condition can be constructed, as shown in FIG. 33B.

Figure 34:
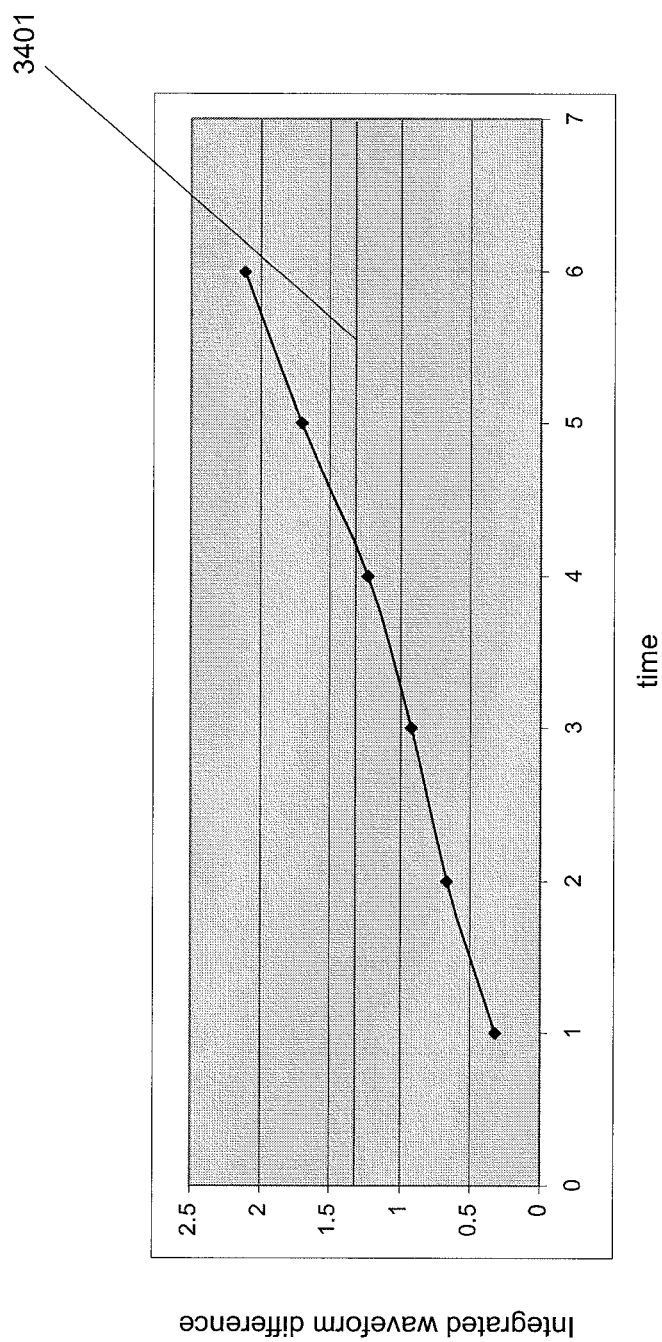
FIG. 34 show examples of data obtained by a wireless sensor module in accordance with one or more embodiments of the invention.

FIG. 34 shows the result of integrating (summing) each individual curve shown in FIG. 33B. As can be seen in the figure, the sum of each individual curve provides for a metric that may be monitored and when passing above a threshold level 3401, a "pump-off" alarm may be triggered. While the sum of the normalized difference waveforms is shown in FIG. 34, any suitable metric or combination of metrics may be used using the difference value waveforms of FIG. 33B, e.g., total RMS deviation, peak value, and or width, may be used without departing from the scope of the present disclosure.

Figure 35:
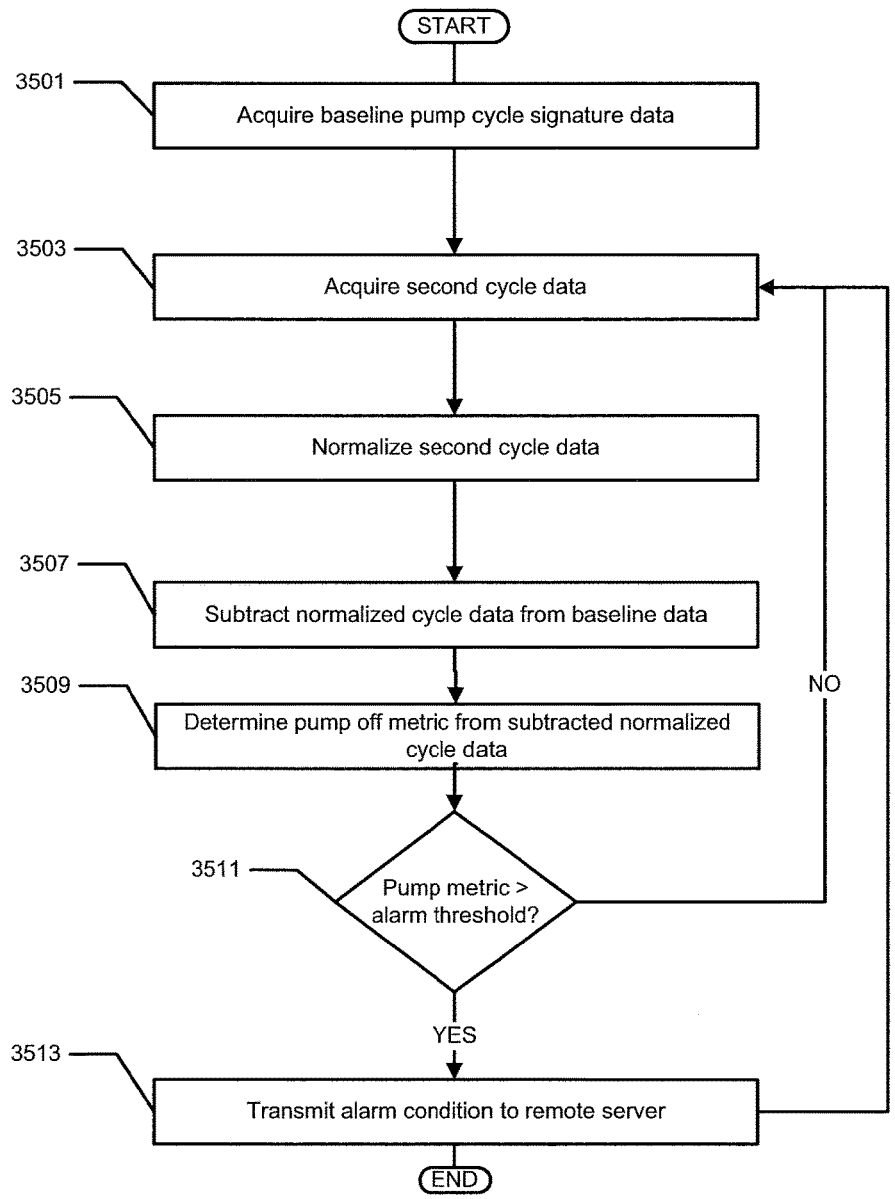
FIG. 35 shows a flowchart describing a method for rod pump monitoring using a wireless sensor module in accordance with one or more embodiments of the invention.

FIG. 35 shows a flowchart describing a method for rod pump monitoring using a wireless sensor module in accordance with one or more embodiments of the invention. In step 3501, baseline pump cycle signature data is acquired from the accelerometer of the wireless sensor module. In step 3503, a second pump cycle signature is acquired from the accelerometer. The baseline and subsequent pump cycle signature data may be stored in the internal memory of the wireless sensor module or, after acquisition; the data may be transmitted to a remote server and stored for further processing. In step 3505, the second or subsequent cycle data are normalized to the baseline signal, e.g., the time data for each cycle are normalized to the pump period for that cycle and the orientation data is normalized to the peak deviation for that cycle. In step 3507, each second or subsequent cycle is subtracted from the baseline signal. In step 3509 a pump off metric is determined from the subtracted normalized waveforms. For example, the metric may be the integrated subtracted normalized waveforms, e.g., as shown in FIG. 34. In step 3511, the "pump off" metric is compared to a threshold value. If the pump metric is above the threshold value an alarm is triggered and then transmitted to a remote server in step 3513. In accordance with one or more embodiments, the immediate alarm conditions can be detected and reported as needed, otherwise the method returns to step 3503. Furthermore the alarm can be set by field experience and is normally activated when a running average of the prior hour or two of data measurements differs by more than a set percentage of the fully pumping data. In other embodiments, the cycle time may be monitored rather than the normalized cycle shape as described above. In the case of cycle time monitoring, the alarm can also be set by field experience and is normally activated when a running average of the prior hour or two of data measurements differs by more than a set percentage of the fully pumping time (called the 'pump up time').

Figure 36A:
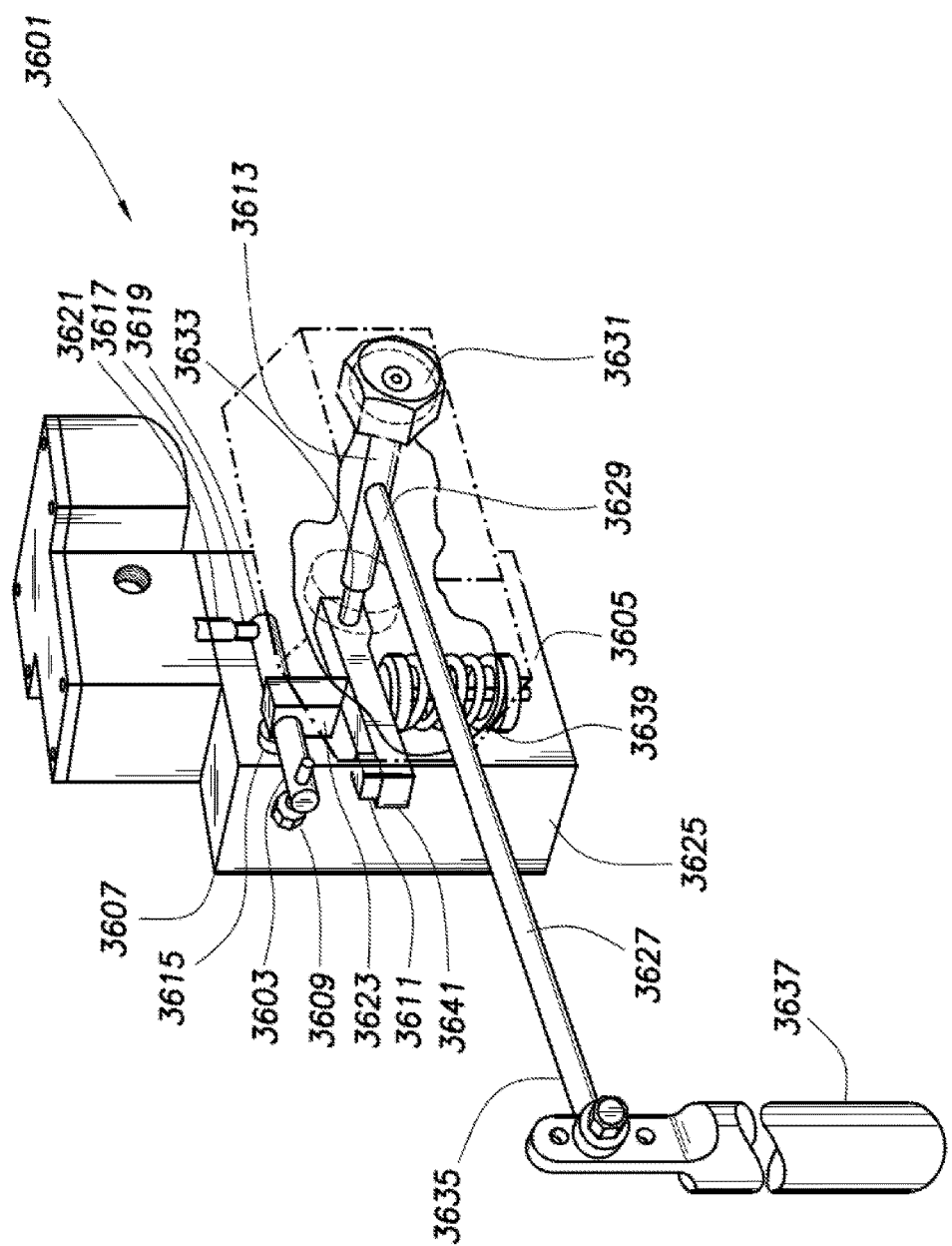
FIGS. 36A-36B show an example of a system for field monitoring of stationary assets in accordance with one or more embodiments of the invention.
Figure 36B:
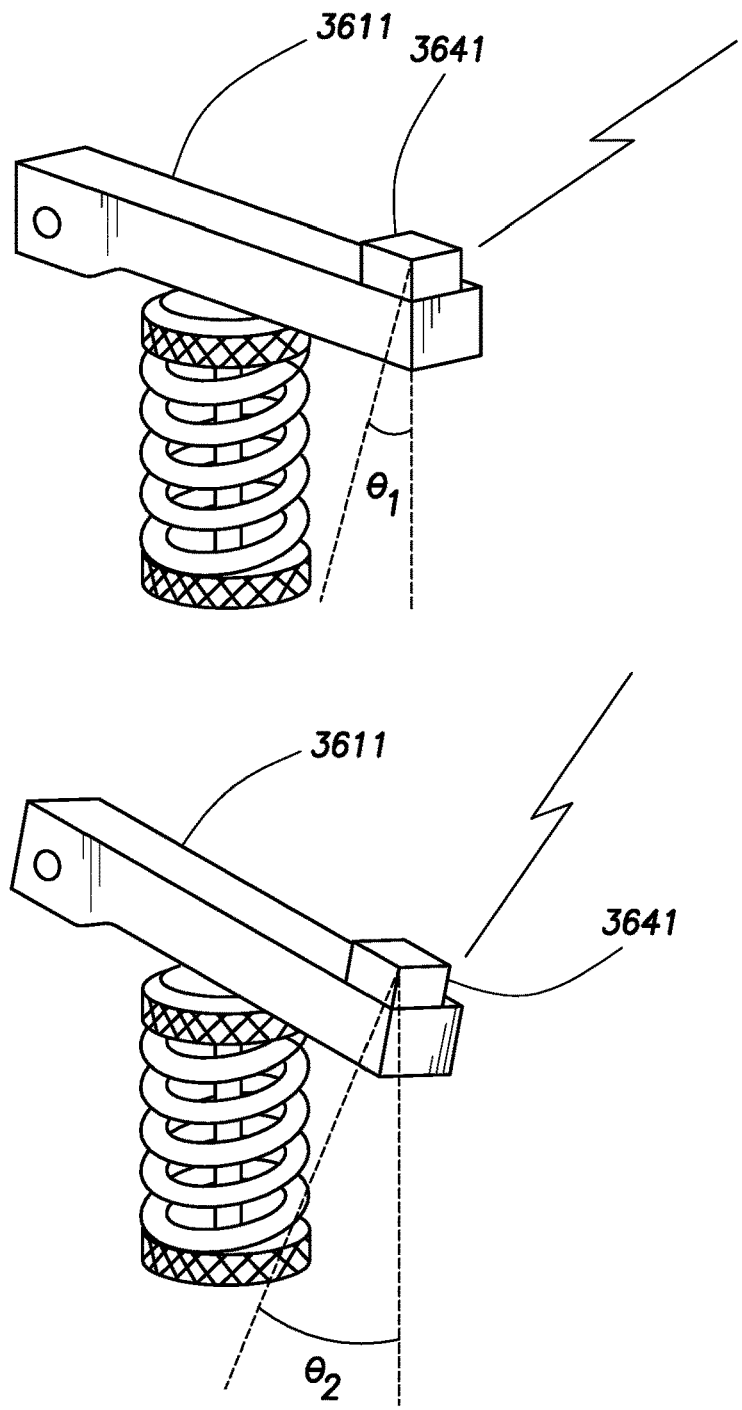

FIGS. 36A-36B show an example of a system for field monitoring of stationary assets in accordance with one or more embodiments of the invention. More specifically, FIGS. 36A-36B show an example of an improved fluid level controller for controlling the fluid level in a vessel. One of ordinary skill will appreciate that many known fluid level controllers are known in the art. For example, U.S. Pat. No. 6,354,323, incorporated herein by reference in its entirety, describes one example of a known fluid level controller that may be monitored by a wireless sensor module in accordance with one or more embodiments of the invention.

FIG. 36A shows a wirelessly monitored fluid level controller 3601 in accordance with one or more embodiments of the invention. The fluid level controller 3601 includes a main housing 3607 formed by a plurality of sidewalls which define a normally closed interior. Fluid level controller 3601 is connectable to a sidewall of a fluid containing vessel (not shown), such as an oil and gas separator tank for controlling the liquid level therein. A displacement shaft 3627 has a first end 3629 connected to the torque shaft 3613 at a point intermediate the inner and outer bearing assemblies 3631, 3633, respectively, and extending perpendicular thereto. The displacement shaft 3627 has a second end 3635 that extends to a liquid displacement member or float 3637 for transmitting vertical forces responsive to changes in liquid level as a force tending to rotate the torque shaft 3613.

A lever 3603 is pivotally mounted to the side wall 3605 of housing 3607 at first end 3609, and in a plane generally parallel to that of the torque bar 3611. A suitable connector is provided for interconnecting the torque bar 3611 and the lever 3603 for transmitting forces exerted on torque shaft 3613 to the lever 3603. In the embodiment illustrated in FIGS. 36A and 36B, an adjustable connector 3615 interconnects the torque bar 3611 and lever 3603 for transmitting force exerted on the torque shaft 3613 to the lever. Slight movement of torque bar 3611 is transmitted through the adjustable connector to pilot pin 3617, whereby movement of lever 3603 actuates pilot pin 3617. The second end 3619 of lever 3603 engages pilot pin 3617 which extends into pilot 3621 to control the valve (not shown) that opens and closes flow of fluid form the vessel whose fluid level is to be controlled, as is known in the art. In some level controllers, the adjustable connector 3615 is a fulcrum member 3623 which is slidably mounted on the lever in engagement with the upper surface of torque bar 3611. The position of the fulcrum member 3623 on the lever 3603 can be changed by loosening the adjustment screw located within adjustable connector 3615.

A biasing element 3639 is located within the main housing interior and contacts the torque bar 3611 to thereby balance force exerted on the torque bar 3611 by the liquid displacement member 3637 acting on the torque shaft 3613. In the embodiment of FIG. 36A-36B, the biasing element 3639 is a coil spring located within the main housing interior and contacting a lower surface of the torque bar. The coil spring 3639 has a characteristic coil tension which is adjustable by means of an adjustment screw, the head of which is accessible from a location exterior of the main housing.

Attached to the torque bar 3611 is a wireless sensor module 3641. In accordance with one or more embodiments of the invention, the wireless sensor module is constructed and designed in a manned that is identical to that described above in reference to FIGS. 3A-3C. Accordingly, the detailed description laid out above will not be reproduced here. Furthermore, in accordance with one or more embodiments, the sensors 323a, 323b, . . . , 323n include at least one accelerometer. The wireless sensor module is affixed, e.g., by way of suitable double sided tape, to the torque bar 3611 as shown in FIGS. 36A-36B. Accordingly, as fluid is drained from the tank, torque bar 3611 of the level controller will displace, thereby causing the accelerometer of the wireless sensor module to register a change in orientation over time from $\theta_1$ to $\theta_2$. As described above in reference to FIGS. 3A-3C and FIG. 34, the accelerometer provides a data stream to microcontroller 329 where it is stored in memory. As with all the sensor modules described above, the acquired data may be transmitted to a remote server for further processing or may be processed locally by the microcontroller of the wireless sensor module itself into a vector of torque bar angle versus time before transmission to the remote server.

Figure 37:
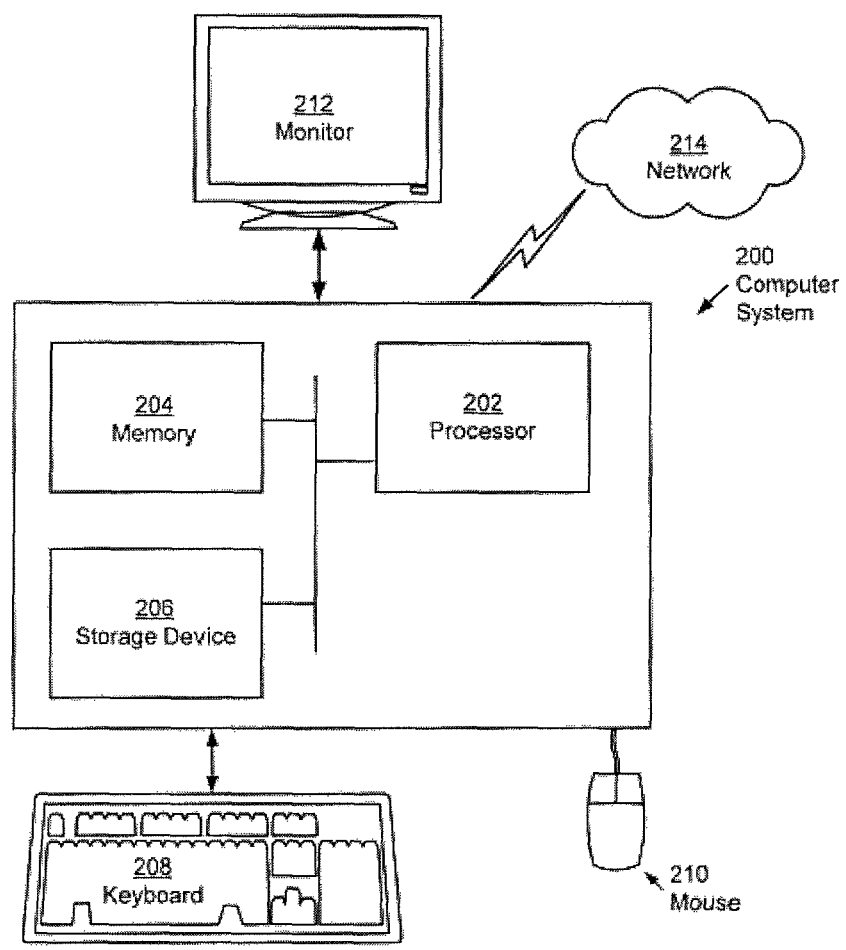
FIG. 37 shows a computer system in accordance with one or more embodiments of the invention.

Embodiments of the methods disclosed herein may be implemented on virtually any type of computer regardless of the platform being used. For example, as shown in FIG. 37, a computer system (200) includes one or more processor(s) (202), associated memory (204) (e.g., random access memory (RAM), cache memory, flash memory, etc.), a storage device (206) (e.g., a hard disk, an optical drive such as a compact disk drive or digital video disk (DVD) drive, a flash memory stick, etc.), and numerous other elements and functionalities typical of today's computers (not shown). The computer (200) may also include input means, such as a touchscreen, keyboard (208), a mouse (210), or a microphone (not shown). Further, the computer (200) may include output means, such as a monitor (212) (e.g., a liquid crystal display (LCD), a plasma display, or cathode ray tube (CRT) monitor). The computer system (200) may be connected to a network (214) (e.g., a local area network (LAN), a wide area network (WAN) such as the Internet, or any other similar type of network) via a network interface connection (not shown). Those skilled in the art will appreciate that many different types of computer systems exist, and the aforementioned input and output means may take other forms. For example, the computer system (200) may be a server system having multiple blades. Generally speaking, the computer system (200) includes at least the minimal processing, input, and/or output means necessary to practice embodiments of the invention. Further, software instructions to perform embodiments of the invention may be stored on a computer readable medium such as a compact disc (CD), a diskette, a tape, or any other computer readable storage device.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for determining a fill level of a container, the method comprising:
   generating an acoustic impulse with an acoustic impulse generator;
   acquiring impulse data with an acoustic impulse receiver spatially separated from the acoustic impulse generator;
   wherein a first portion of the impulse data comprises preflexural wave data and a second portion of the impulse data comprises flexural wave data;
   computing a first impulse arrival time using the preflexural wave data;
   computing a second impulse arrival time using the flexural wave data; and
   computing the fill level of the container based on a difference between the first impulse arrival time and the second impulse arrival time.

2. The method claim 1, wherein at least one of the first portion of the impulse data and the second portion of the impulse data are filtered to remove noise.

3. The method claim 1, wherein at least one of the first impulse arrival time and the second impulse arrival time are corrected for temperature effects.

4. The method of claim 1, wherein computing the first impulse arrival time comprises:
   selecting a first predetermined reference point in the first portion of the impulse data; and
   computing the first impulse arrival time based on the selected first predetermined reference point.

5. The method of claim 4, wherein selecting the first predetermined reference point comprises:
   an acquisition time window of at least one of the first impulse arrival time and second impulse arrival time is determined by use of a physical model.

6. The method of claim 1, wherein computing the second impulse arrival time comprises:
   selecting a second predetermined reference point in the second portion of the impulse data; and
   computing the second impulse arrival time based on the second selected predetermined reference point.

7. The method of claim 6, wherein selecting the second predetermined reference point comprises:
   an acquisition time window of at least one of the first impulse arrival time and second impulse arrival time is determined by use of a physical model.

8. The method of claim 1, wherein computing the flexural wave data further comprises:
   acquiring and storing a reference acoustic impulse wave data set; and
   computing a flexural wave impulse arrival time based on the difference between the flexural wave data and the reference acoustic impulse wave data set.

* * * * *